US008779138B2

(12) United States Patent
Yang

(10) Patent No.: US 8,779,138 B2
(45) Date of Patent: *Jul. 15, 2014

(54) CAMPTOTHECIN DERIVATIVES AS CHEMORADIOSENSITIZING AGENTS

(75) Inventor: Li-Xi Yang, San Francisco, CA (US)

(73) Assignees: Sutter West Bay Hospital, San Francisco, CA (US); Catholic Healthcare West, San Francisco, CA (US)

( * ) Notice: Subject to any disclaimer, the term of this patent is extended or adjusted under 35 U.S.C. 154(b) by 213 days.

This patent is subject to a terminal disclaimer.

(21) Appl. No.: 13/012,772

(22) Filed: Jan. 24, 2011

(65) Prior Publication Data

US 2011/0184009 A1 Jul. 28, 2011

Related U.S. Application Data

(63) Continuation of application No. 11/444,150, filed on May 30, 2006, now Pat. No. 7,875,602.

(60) Provisional application No. 60/728,924, filed on Oct. 21, 2005.

(51) Int. Cl.
*C07D 471/00* (2006.01)
*A61K 31/33* (2006.01)

(52) U.S. Cl.
USPC .......... 546/48; 514/183

(58) Field of Classification Search
USPC .......... 546/48; 514/183
See application file for complete search history.

(56) References Cited

U.S. PATENT DOCUMENTS 4,399,282 A 8/1983 Miyasaka et al.
4,604,463 A 8/1986 Miyasaka et al.
4,663,161 A 5/1987 Mannino et al.
4,727,068 A 2/1988 Abrams et al.
4,797,397 A 1/1989 Suto et al.
4,921,963 A 5/1990 Skov et al.
4,927,941 A 5/1990 Kagiya et al.
4,943,579 A 7/1990 Vishnuvajjala et al.
4,945,102 A 7/1990 Suzuki et al.
4,954,515 A 9/1990 Suto
4,977,273 A 12/1990 Kagiya et al.
5,013,556 A 5/1991 Woodle et al.
5,026,694 A 6/1991 Skov et al.
5,032,617 A 7/1991 Lee et al.
5,036,096 A 7/1991 Suto
5,041,653 A 8/1991 Lee et al.
5,043,165 A 8/1991 Radhakrishnan
5,064,849 A 11/1991 Suzuki et al.
5,077,057 A 12/1991 Szoka, Jr.
5,175,278 A 12/1992 Peik et al.
5,175,287 A 12/1992 Lee et al.
5,196,413 A 3/1993 Teicher et al.
5,294,715 A 3/1994 Papadopoulou-Rosenzweig et al.
5,304,654 A 4/1994 Kagiya et al.
5,342,959 A 8/1994 Beylin et al.
5,549,910 A 8/1996 Szoka, Jr.
5,552,156 A 9/1996 Burke
5,631,237 A 5/1997 Dzau et al.
5,718,914 A 2/1998 Foldvari
5,736,156 A 4/1998 Burke
5,783,211 A 7/1998 Manzo et al.
5,827,533 A 10/1998 Needham
5,874,105 A 2/1999 Watkins et al.
5,882,679 A 3/1999 Needham
5,916,896 A 6/1999 Wall et al.
5,935,949 A 8/1999 White
5,965,566 A 10/1999 Greenwald et al.
5,981,542 A 11/1999 Bigg et al.
6,028,078 A 2/2000 Hausheer et al.
6,040,313 A 3/2000 Wall et al.
6,057,303 A 5/2000 Haridas et al.
6,060,604 A 5/2000 Yang et al.
6,096,336 A 8/2000 Cao et al.
6,113,906 A 9/2000 Greenwald et al.
6,114,529 A 9/2000 Kawaguchi et al.
6,120,793 A 9/2000 Cao et al.
6,127,355 A 10/2000 Greenwald et al.
6,153,655 A 11/2000 Martinez et al.
6,207,832 B1 3/2001 Curran et al.
6,281,223 B1 8/2001 Choy et al.
6,339,091 B1 1/2002 Bigg et al.
6,350,756 B1 2/2002 Yang et al.
6,403,604 B1 6/2002 Yang et al.

(Continued)

FOREIGN PATENT DOCUMENTS

EP 0861842 11/2003
WO WO 95/10304 4/1995

(Continued)

OTHER PUBLICATIONS

Kemp, et al. Combined radiation and 9-nitrocamptothecin (rubitecan) in the treatment of locally advanced pancreatic cancer. Annals New York Academy Sciences, 2000, vol. 922, pp. 922:320-323.

Adams et al. "Electron affinic sensitization I. A Structural Basis for Chemical Radiosensitizers in Bacteria," Int. J. Radiat. Biol. 1969, 15(5):457-471.

Adams et al. "Electron affinic sensitization Part II: Para-Nitroacetophenone: A Radiosensitizer for Anoxic Bacterial and Mammalian Cells." Int. J. Radiat, Biol. 1971, 19(6):575-585.

(Continued)

*Primary Examiner* — Wu-Cheng Winston Shen
*Assistant Examiner* — Christopher R Stone
(74) *Attorney, Agent, or Firm* — Foley & Lardner LLP

(57) ABSTRACT

Camptothecin-based compounds are useful for treating a neoplasm in mammalian subjects by administering such compound to the subjects in combination with radiotherapy, i.e., the treatment of tumors with radioactive substances or radiation from a source external to the subject. Camptothecin-based compounds are modified by positioning at least one electron-affinic group around the camptothecin structure to enhance their value in combination with radiotherapy. New Camptothecin-based compounds are disclosed that are useful for treating cancer by administering the novel compounds alone or in combination with radiotherapy.

30 Claims, 3 Drawing Sheets

(56) References Cited

U.S. PATENT DOCUMENTS

| | | | |
|---|---|---|---|
| 6,423,707 | B1 | 7/2002 | Yang et al. |
| 6,492,335 | B1 | 12/2002 | Lerchen et al. |
| 6,506,734 | B1 | 1/2003 | Lerchen et al. |
| 6,855,720 | B2 | 2/2005 | Yang |
| 6,933,302 | B2 | 8/2005 | Yang |
| 2002/0040155 | A1 | 4/2002 | Holton et al. |
| 2002/0049324 | A1 | 4/2002 | Cao et al. |
| 2003/0138432 | A1 | 7/2003 | Glazier |

FOREIGN PATENT DOCUMENTS

| | | |
|---|---|---|
| WO | WO 96/26950 | 9/1996 |
| WO | WO 97/19085 | 5/1997 |
| WO | WO 97/28165 | 8/1997 |
| WO | WO 98/13059 | 4/1998 |
| WO | WO 98/14190 | 4/1998 |
| WO | WO 98/35940 | 8/1998 |
| WO | WO 99/17805 | 4/1999 |
| WO | WO 00/66127 | 11/2000 |
| WO | WO 00/67801 | 11/2000 |
| WO | WO 03/014069 | 2/2003 |

OTHER PUBLICATIONS

Adams, "The Impact of Tumor Physiology on Camptothecin-Based Drug Development." *Curr. Med. Chem.—Anti-Cancer Agents*, Jan. 2005, 5(1),1-13.

Adams, D. J. et al, "Camptothecin analogs with enhanced activity against human breast cancer cells. II. Impact of the tumor pH gradient." *Cancer Chemother. Pharmacol*. 57:145-54 (2006).

Adams, D.J. et al, "Camptothecin analogs with enhanced activity against human breast cancer cells. I. Correlation of potency with lipophilicity and persistence in the cleavage complex." *Cancer Chemother. Pharmacol*. 57:135-44 2006.

Ando, Y. et al. "Irinotecan in Small-Cell Lung Cancer." *N Engl J Med*, 346(18):1414-5 (2002).

Armstrong DK. "Topotecan dosing guidelines in ovarian cancer: reduction and management of hematologic toxicity", *The Oncologist* 2004; 9(1):33-42.

Balasubramanian, B. N. et al. "Recent Developments in Cancer Cytotoxics." *Annual Reports in Med. Chem*. 33:151-9 (1998).

Bernier-Chastagner V, Grill J, Doz F, Bracard S, Gentet JC, Marie-Cardine A, Luporsi E, Margueritte G, Lejars O, Laithier V, Mechinaud F, Millot F, Kalifa C, Chastagner P. "Topotecan as a radiosensitizer in the treatment of children with malignant diffuse brainstem gliomas: Results of a French Society of Paediatric Oncology Phase II Study". *Cancer*, 2005;104(12):2792-7.

Block, Jr., P. et al. "(+)- and (−)-alpha-(2,4,5,7-Tetranitro-9-Fluorenylideneaminooxy)Propionic Acid." *Organic Syntheses*. 48:120-6 (1968).

Bom, D. et al. "The Novel Silatecan 7-tert-Butyldimethylsilyl-10-hydroxycamptothecin Displays High Lipophilicity, Improved Human Blood Stability, and Potent Anticancer Activity." *J. Med. Chem*. 43(21):3970-80 (2000).

Bomgaars, L. et al. "The Development of Camptothecin Analogs in Childhood Cancers." *Oncolgist* 6:506-16 (2001).

Brodin, A. et al. "In vitro release studies on lidocaine aqueous solutions, micellar solutions, and o/w emulsions," *Acta Pharm Suec*. 19:267-84 (1982).

Brown, J. M. "The Hypoxic Cell:A Target for Selective Cancer Therapy—Eighteenth Bruce F. Cain Memorial Award Lecture." *Cancer Res*. 59:5863-70 (1999).

Caffo, O. "Radiosensitization with chemotherapeutic agents." *Lung Cancer* 34:S81-90 (2001).

Cannon, J.G., Chapter 19 of Burger's Medicinal Chemistry and Drug Discovery, vol. I: Principles and Practice Wiley Interscience, 5 Edition, p. 783-802, 1995.

Cao, Z. et al. "Alkyl Esters of Camptothecin and 9-Nitrocamptothecin:Synthesis, in Vitro Pharmacokinetics, Toxicity, and Antitumor Activity." *J. Med. Chem*. 41(1):31-7 (1998).

Chastagner P, Merlin JL, Marchal C, Hoffstetter S, Barberi-Heyob M, Vassal G, Duprez A. "In vivo potentiation of radiation response by topotecan in human rhabdomyosarcoma xenografted into nude mice" *Clin Cancer Res*. 2000; 6(8):3327-3333.

Chaterjee, A. et al. "Safety, Tolerability, Pharmacokinetics, and Pharmacodynamics of an Orally Active Novel Camptothecin Analog, DRF-1042, in Refractory Cancer Patients in a Phase I Dose Escalation Study." *J. Clin. Pharmacol*. 44:723-36 (2004).

Chen et al. "Enhancement of radiotherapy with DNA topoisomerase I-targeted drugs." Critical Reviews in Oncology/Hematology (2004) 50(2):111-119, XP002591963.

Chen, A. Y. et al. "DNA Topoisomerase I-Targeting Drugs as Radiation Sensitizers." *Oncology* 13(10 Suppl 5):39-46 (1999).

Chen, A. Y. et al. "Mammalian DNA Topoisomerase I Mediates the Enhancement of Radiation Cytotoxicity by Camptothecin Derivatives." *Cancer Res*. 57:1529-36 (1997).

Chen, A. Y., et al. "Induction of Radiosensitization by Indolocarbazole Derivatives:The Role of DNA Topoisomerase I," *Molecular Pharmacol*. 66(3):553-60 (2004).

Cho, J.-Y. et al. "Simple and sensitive determination of the new antitumor drug CKD-602 in human plasma by liquid chromatography." *J. Chromatogr. B* 784:25-31 (2003).

Choy, H. "Taxanes in Combined-Modality Therapy for Solid Tumors." *Oncology* 13(10 Suppl 5):23-38 (1999).

Dallavalle, S. et al, "Novel 7-Substituted Camptothecins with Potent Antitumor Acitvity." *J. Med Chem*. 43(21):3963-9 (2000).

De Cesare, M. et al. "Efficacy of the Novel Camptothecin Gimatecan against Orthotopic and Metastatic Human Tumor Xenograft Models." *Clin. Cancer Res*. 10:7357-64 (2004).

De Groot, F. M. H. et al. "Novel 20-Carbonate Linked Prodrugs of Camptothecin and 9-Aminocamptothecin Designed for Activation by Tumour-Associated Plasmin." *Bioorg. Med. Chem. Lett*. 12:2371-6 (2002).

Del Poeta, M. et al. "Comparison of In Vitro Activities of Camptothecin and Nitidine Derivatives against Fungal and Cancer Cells." *Antimicrob. Agents Chemother*. 43(12):2862-8 (1999).

Di Francesco, A. M. et al. "The novel lipophilic camptothecin analogue gimatecan in very active in vitro in human neuroblastoma:A comparative study with SN38 and topotecan." *Biochem. Pharmacol*. 70:1125-36 (2005).

Driver et al. "Synthesis and Pharmacology of New Camptothecin Drugs." *Mini-Reviews in Medicinal Chemistry*, May 2005, 5(5):425-439.

Driver, R. W. et al. "Synthesis and pharmacology of new camptothecin drugs." *Mini-Reviews in Medicinal Chem*. 5(1):1-13 (2005).

Du, W. et al. "Semisynthesis of DB-67 and other silatecans from camptothecin by thiol-promoted addition of silyl radicals." *Bioorg. Med. Chem*. 11:451-8 (2003).

Forssen, E. A. et al. "Selective in Vivo Localization of Daunorubicin Small Unilamellar Vesicles in Solid Tumors." *Cancer Res*. 52:3255-61 (1992).

Freireich, E. J. et al. "Quantitative comparison of toxicity of anticancer agents in mouse, rat, hamster, dog, monkey, and man." *Cancer Chemother. Rep*. 50(4):219-44 (1966).

Fung, B. M. et al. "Perfluorochemical emulsions with fluorinated surfactants and anticancer drugs." *Biomat., Art, Cells, Art, Org*. 16(1-3):439-40 (1988).

Gao, H. et al. "Synthesis and antitumor activity of 7-ethyl-9-alkyl derivatives of camptothecin." *Bioorg. Med. Chem. Lett*. 15:2003-6 (2005).

Gao, H. et al. "Synthesis and antitumor activity of the hexacyclic camptothecin derivatives." *Bioorg. Med. Chem. Lett*. 15:3233-36 (2005).

Garcia-Carbonero, R. et al, "Current Perspectives on the Clinical Experience, Pharmacology and Continued Development of the Camptothecins." *Clin. Cancer Res*. 8:641-61 (2002).

Grigsby. P. W. et al. "Irradiation with or without misonidazole for patients with stages IIIB and IVA carcinoma of the cervix:final results of RTOG 80-05." *Int J Radiat Oncol Biol Phys* 44(3):513-7 (1999).

(56) References Cited

OTHER PUBLICATIONS

Guitto, A. et al. "Synthesis, Characterization, and Preliminary in Vivo Tests of New Poly (ethylene glycol) Conjugates of the Antitumor Agent 10-Amino-7-ethylcamptothecin." *J. Med. Chem.* 47(5):1280-9 (2004).
Hafian H, Venteo L, Sukhanova A, Nabiev I, Lefevre B, Pluot M. "Immunohistochemical study of DNA topoisomerase I, DNA topoisomerase II alpha, p53, and Ki-67 in oral preneoplastic lesions and oral squamous cell carcinomas" *Hum Pathol.* 2004; 35(6):745-51.
Hartmann JT, Lipp HP. "Camptothecin and podophyllotoxin derivatives: inhibitors of topoisomerase I and II—mechanisms of action, pharmacokinetics and toxicity profile", *Drug Safety*, 2006; 29(3):209-30.
He, X. et al. "Synthesis and biological evaluation of bis and monocarbonate prodrugs of 10-hydroxycmptothecins." *Bioorg. Med. Chem.* 12:4003-8 (2004).
Hecht SM. "Camptothecin: roles of the D and E rings in binding to the topoisomerase I-DNA covalent binary complex", *Curr. Med Chem. Anticancer Agents*; 2005; 5(4):353-362.
Henne et al. "Synthesis and activity of a folate peptide camptothecin prodrug" bioorganic & medicinal, *Chemistry letters* (2006) 16(20):5350-5355, XP0251 07171.
Herscher, L. L. et al. "Principles of Chemoradiation:Theoretical and Practical Consideration." *Oncology* 13(10 Suppl 5):11-22 (1999).
Holm C, Covey J.M., Kerrigan D., Pommier Y., "Differential requirement of DNA replication for the cytotoxicity of DNA topoisomerase I and II inhibitors in Chinese hamster DC3F cells", *Cancer Res.* 1989:49(22):6365-6368.
Horig et al., "From bench to clinic and back: Perspective on the 1st IQPC Translational Research Conference," Journal of Translational Medicine, 2(44), p. 1-8, 2004.
Hsiang Y.H., Lihou M.G., Liu L.F. "Arrest of replication forks by drug-stabilized topoisomerase I-DNA cleavable complexes as a mechanism of cell killing by camptothecin" *Cancer Res.* 1989, 49(18):5077-82.
Husain, I.: Mohler, JL.; Seigler, HF.; Besterman, JM, "Elevation of topoisomerase I messenger RNA, protein, and catalytic activity in human tumors: demonstration of tumor-type specificity and implications for cancer chemotherapy", *Cancer Res.* 1994, 54, 539-546.
Jaklevic et al. "Relative Contribution of Dna Repair, Cell Cycle Checkpoints, and Cell Death to Survival After DNA Damage in *Drosophila* Larvae." *Current Biology*, Jan. 2004, 14(1):23-32.
Keir, S.T. et al. "Therapeutic activity of 7-[(2-trimethylsilyl)ethyl)]-20 (S)-camptothecin against central nervous system tumor-derived xenografts in athymic mice." *Cancer Chemother Pharmacol.* 48(1):83-7 (2001).
Keskin, O. et al. "Characterization of anticancer agents by their growth inhibitory activity and relationships to mechanism of action and structure." *Anti Cancer Drug Design* 15:78-98 (2000).
Khokhar, A. R. et al. "Chemical and Biological Studies on a Series of Lipid-Soluble (*trans*-(*R,R*)- and -(*S,S*)-1,2-Diaminocyclohexane)platinum(II) Complexes Incorporated in Liposomes." *J. Med. Chem.* 34(1):325-9 (1991).
Kingsbury, W. D. et al. "Synthesis of Water-Soluble (Aminoalkyl)camptothecin Analogues:Inhibition of Topoisomerase I and Antitumor Activity," *J. Med. Chem.* 34(1):98-107 (1991).
Kohara, H. et al., "Synergistic Effects of Topoisomerase I Inhibitor, 7-ethyl-10-hydroxycamptothecin, and Irradiation in a Cisplatin-resistant Human Small Cell Lung Cancer Cell Line." *Clin. Cancer Res.* 8:287-92 (2002).
Krontiris, T.G. "Molecular and Cellular Biology of Cancer." *Internal Medicine*. 4th Ed. St. Louis: Mosby-Year Book, Inc., 1994. 699-715.
Lamond JP, Wang M, Kinsella TJ, Boothman DA, "Radiation lethality enhancement with 9-aminocamptothecin: comparison to other topoisomerase I inhibitors". *Int. J Radiat. Oncol. Biol Phys.* 1996;36(2):369-76.
Lanond, JP, Wang, M, Kinsella, TJ, Boothman, DA, "Concentration and timing dependence of lethality enhancement between topotcan, a topoisomerase I inhibitor, and ionizing ratiation", *Int. J. Radiat. Oncol Biol Phys.* 1996; 36(2):361-8.
Lasic, D.D. "Mixed Micelles in drug delivery." *Nature* 335:279-280 (1992).
Lee, D. et al. "A phase I/II study of the hypoxic cell sensitizer misonidazole as an adjunct to high ractional dose radiotherapy in patients with unresectable squamous cell carcinoma of the head and neck:a RTOG randomized study (#70-04)." *Int J Radiat Oncol Biol Phys* 16:465-70 (1989).
Lee, D. et al. "Results of an RTOG phase III trial (RTOG 85-27) comparing radiotherapy plus tanidazole with radiotherapy alone for locally advanced head and neck carcinomas," *Int J Radiat Oncol Biol Phys* 32(3):567-76 (1995).
Legarza, K. et al. "Novel Camptothecin Derivatives." in vivo 18:xxx-xxx (2005).
Lerchen, H.-G. "Milestones in camptothecin research." *Drugs of the Future* 27(9):869-76 (2002).
Li, D.-Z, et al. "Synthesis and antitumor activity of A-ring modified hexacyclic analogues of camptothecin." *Yao Xue Xue Bao* 40(3):241-7 (2005).
Maliepaard, M. et al. "Circumvention of Breast Cancer Resistance Protein (BCRP)-mediated Resistance to Camptothecins in Vitro Using Non-Substrate Drugs or the BCRP Inhibitor GF120918." *Clin. Cancer Res.* 7:935-41 (2001).
Marchesini, R, Colombo, A, Caserini, C, Perego, P, Supino, R, Capranico, G Tronconi, M, Zunino, F., "Interaction of ionizing radiation with topotecan in two human tumor cell lines", *Int. J Cancer*, 1996;66(3):342-346.
Mattern, M. R. et al. "Synergistic Cell Killing by Ionizing Radiation and Topoisomerase I Inhibitor Topotecan (SK&F 104864)." *Cancer Res.* 51:5813-6 (1991).
Miller, T. J. et al. "CI-1010 induced opening of the mitochondrial permeability transition pore precedes oxidative stress and apoptosis in SY5Y neuroblastoma cells." *Brain Res.* 963:43-56 (2003).
Mitsui, I. et al. "A New Water-soluble Camptothecin Derivative, DX-8951f, Exhibits Potent Antitumor Activity against Human Tumors in vitro and in vivo." *Jpn. J. Cancer Res.* 86:776-82 (1995).
Moody, T. W. et al. "Camptothecin-somatostatin conjugates inhibit the growth of small cell lung cancer cells." *Peptides* 26:1560-6 (2005).
Newman, M. S. et al. "2,4,5,7-Tetranitrofluorenone." *Organic Syntheses* Coll. vol. 5:1029-37 (1973).
Newman, M. S. et al. "2,4,5,7-Tetranitrofluorenone." *Organic Synthesis* 42:95-6 (1962).
Nomoto, T. et al. "Characterization of a Human Small-Cell Lung Cancer Cell Line Resistant to a New Water-soluble Camptothecin Derivative, DX-8951f." *Jpn. J. Cancer Res.* 89:1179-86 (1998).
Ohtsu, H. et al. "Antitumor Agents 216. Synthesis and Evaluation of Paclitaxel-Camptothecin Conjugates as Novel Cytotoxic Agents." *Bioorg. Med. Chem.* 11:1851-7 (2003).
O'Leary, J. et al. "Camptohecins:a Review of their Development and Schedules of Administration." *European Journal of Cancer* 34(10):1500-8 (1998).
Omura M, Torigoe S, Kubota N. "SN-38, a metabolite of the camptothecin derivative CPT-11, potentiates the cytotoxic effect of radiation in human colon adenocarcinoma cells grown as spheroids". *Radiother Oncol.* 1997; 43(2)1 97-201.
Ouimet-Oliva, D. et al. "Effect of danazol on the radiographic density of breast parenchyma." *J. Can. Assoc. Radiol.* 32:159-61 (1981).
Overgaard, J. "Sensitization of hypoxic tumour cells—clinical experience." *Int. J. Radiat. Biol.* 56(5):801-11 (1989).
Overgaard, J. et al. "A randomized double-blind phase IIII study of nimorazole as a hypoxic radiosensitizer of primary radiotherapy in supraglottic larynx and pharynx carcinoma. Results of the Danish Head and Neck Cancer Study (DAHANCA) Protocol 5-85." *Radiother. Oncol.* 46:135-46 (1998).
Overgaard, J. et al. "Misonidazole combined with radiotherapy in the treatment of carcinoma of the uterine cervix." *Int. J. Radiat. Oncol. Biol. Phys.* 16(4):1069-72 (1989).
Overgaard, J. et al. "Misonidazole combined with split-course radiotherapy in the treatment of invasive carcinoma of larynx and pharynx:Report from the Dahanca 2 Study." *Int. J. Radiat. Oncol. Biol. Phys.* 16(4):1065-8 (1989).

(56) References Cited

OTHER PUBLICATIONS

Pan, X.-D. et al. "Regioselective Synthesis and Cytotoxicities of Camptothecin Derivatives Modified at the 7-, 10- and 20-Positions." *Biorg. Med. Chem. Lett.* 13:3739-41 (2003).
Paradiso A, Xu J, Mangia A, Chiriatti A, Simone G, Zito A, Montemurro S, Giuliani F, Maiello E, Colucci G.. "Topoisomerase-I, thymidylate synthase primary tumour expression and clinical efficacy of 5-FU/CPT-11 chemotherapy in advanced colorectal cancer patients", *Int. J Cancer*. 2004;111(2):252-258.
Perego, P. et al. "A Novel 7-Modified Camptothecin Analog Overcomes Breast Cancer Resistance Protein-Associated Resistance in a Mitoxantrone-selected Colon Carcinoma Cell Line." *Cancer Res.* 61:6034-7 (2001).
Perex-Soler, R. et al. "Anthracycline Antibiotics with High Liposome Entrapment:Structural Features and Biological Activity." *Cancer Res.* 50:4260-6 (1990).
Perzyna, A. et al, "Indolizino[1,2-b]quinolines Derived from A-D Rings of Camptothecin:Synthesis and DNA Interaction." *J. Enzyme Inhibition and Med. Chem.* 18(2):101-9 (2003).
Pollack, I. F. et al. "Potent Topoisomerase I Inhibition by Novel Silatecans Eliminates Glioma Proliferation in Vitro and in Vivo." *Cancer Res.* 59:4898-905 (1999).
Pratesi, G. et al. "Gimatecan, a novel ca ptothecin with a promising preclinical profile." *Anticancer Drugs* 15(6):545-52 (2004).
Rapisarda, A. et al. "Identification of Small Molecule Inhibitors of Hypoxia-inducible Factor 1 Transcriptional Activation Pathway." *Cancer Res.* 62:4316-24 (2002).
Rave-Fränk, M. et al, "Combined Effect of Topotecan and Irradiation on the Survival and the Induction of Chromosome Aberrations in Vitro." *Strahlenther Onkol.* 178(9):497-503 (2002) (w/English abstract).
Rowinsky, E. K. "Novel Radiation Sensitizers Targeting Tissue Hypoxia." *Oncology* 13(10 Suppl 5):61-70 (1999).
Saltz, L. et al. "CPT-11 (Irinotecan) and 5-Fluorouracil:a Promising Combination for Therapy of Colorectal Cancer." *European Journal of Cancer* 32A(Suppl. 3):524-31 (1996).
Sawada, S. et al. "Chemical Modification of an Antitumor Alkaloid Camptothecin:Synthesis and Antitumor Acitivity of 7-C-Substituted Camptothecins." *Chem. Pharm. Bull.* 39(10):2574-80 (1991).
Sawada, S. et al. "Synthesis and Antitumor Activity of 20(S)-Camptothecin Derivatives:Carbamate-Linked, Water-Soluble Derivatives of 7-Ethyl-10-hydroxycamptothecin." *Chem. Pharm. Bull.* 39(6):1446-54 (1991).
Schafer et al., "Failure is an option: learning from unsuccessful proof-of-concept trials," Drug Discovery Today, 13(21/22), p. 913-916, 2008.
Shabat, D, et al. "Multiple event activation of a generic prodrug trigger by antibody catalysis," *Proc. Nat. Acad. Sci. USA* 96:6925-30 (1999).
Singer, J. W. et al. "Conjugation of Camptothecins to Poly-(L-Glutamic Acid)." *Annals of the New York Academy of Sciences* 922:136-50 (2000).
Song, M.-G. et al. "Nanomolar concentration of NSC606985, a camptothecin analog, induces leukemic-cell apaptosis through protein kinase Cδ-dependent mechanisms." *Blood* 105(9):3714-21 (2005).
Subrahmanyam, D. et al. "Novel C-ring Analogues of 20(S)-Camptothecin—Part-2 :Synthesis and in Vitro Cytotoxicity of 5-C-Substituted 20(S)-Camptothecin Analogues." *Bioorg. Med. Chem. Lett.* 9:1633-8 (1999).
Supersaxo, A. et al. "Mixed Micelles as a Proliposomal, Lymphotropic Drug Carrier." *Pharm Res.* 8(10):1286-91 (1991).
Takayama, H. et al. "Synthesis of a New Class of Camptothecin Derivatives, the Long-Chain Fatty Acid Esters of 10-Hydroxycamptothecin, as a Potent Prodrug Candidate, and their in Vitro Metabolic Conversion by Carboxylesterases." *Bioorg. Med. Chem. Lett.* 8:415-8 (1998).
Tanabe, K. et al. "Propargylic sulfones possessing a 2-nitroimidazole function:novel hypoxic-cell radiosensitizers with intracellular non-protein thiol depletion ability." *Bioorg. Med. Chem. Lett.* 14:2633-5 (2004).
Tobiassen, T. et al. "Danazol treatment of severely symptomatic fibrocystic breast disease and long-term follow-up—the Hjorring project." *Acta. Obstet. Gyn. Scand. Suppl* 123:159-76 (1984).
Upreti, V. V. et al. "Quantitative determination of DRF-1042 in human plasma by HPLC:validation and application in clinical pharmacokinetics." *Biomed. Chromatogr.* 17:385-90 (2003).
Wadkins, R. M. et al. "Hydrophilic Camptothecin Analogs That Form Extremely Stable Cleavable Complexes with DNA and Topoisomerase I." *Cancer Res.* 64:6679-83 (2004).
Wadkins, R. M. et al. "Topoisomerase I-DNA Complex Stability Induced by Camptothecins and Its Role in Drug Activity." *Curr. Med. Chem.—Anticancer Agents*. 4(4):327-34 (2004).
Wall, M. E. et al. "Camptothecin and Taxol:Discovery to Clinic—Thirteenth Bruce F. Cain Memorial Award Lecture." *Cancer Res.* 55:753-60 (1995).
Wall, M. E. et al. "Plant Antitumor Agents. 30. (lab) Synthesis and Structure Activity of Novel Camptothecin Analogs." *J. Med. Chem.* 36(18):2689-700 (1993).
Wang, C.-Y. et al. "Synthesis and antitumor activity of 20-O-linked nitrogen-based camptothecin ester derivatives," *Bioorg. Med. Chem.* 12:3657-62 (2004).
Wang, H.-K. et al. "The Synthesis of 5-Substituted Camptothecins as Potential Inhibitors of DNA Topoisomerase I." *Bioorg. Med. Chem. Lett.* 5(1):77-82 (1995).
Wang, L. et al. "In vitro study of radiation sensitizing effect of hydroxycamptothecin." *Zhonghua Zhong Liu Za Zhi* 22(2): 124-6 (2000) (w/English abstract).
Wani, M. C. et al. "Plant Antitumor Agents. 23. Synthesis and Antileukemic Activity of Camptothecin Analogues." *J. Med. Chem.* 29(11):2358-63 (1986).
Wani, M. C. et al. "Plant Antitumor Agents. 25. Total Synthesis and Antileukemic Activity of Ring A Substituted Camptothecin Analogues. Structure-Activity Correlations." *J. Med. Chem.* 30(10):1774-9 (1987).
Wasserman, T. H. et al. "Clinical trials with etanidazole (SR-2508) by the radiation therapy oncology group (RTOG)." *Radiother.and Oncol Suppl* 20:129-35 (1991).
Workman et al. "Structure/activity relationships for the enhancement by electron-affinic drugs of the anti-tumour effect of CCNU." *Br. J. Cancer*. 1982:46(2);249-259.
Wu, H. G. "Irinotecan in Combination With Radiation Therapy for Small-Cell and Non-Small-Cell Lung Cancer." *Oncology* 16(9 Suppl):13-8 (2002).
XP 002033248, Abstract, WPI, vol. 46, No. 89, (1989).
XP 002033250 Abstract, WPI, vol. 45, No. 89, (1989).
Yang et al. "Novel camptothecin derivatives. Part 1: Oxyalkanoic acid esters of camptothecin and their in vitro and in vivo antitumor activity" Bioorganic & Medicinal Chemistry Letters (2002) 12(9):1241-1244, XP002349537.
Yokoyama, M. et al. "Toxicity and Antitumor Activity against Solid Tumors of Micelle-forming Polymeric Anticancer Drug and Its Extremely Long Circulation in Blood," *Cancer Res.* 51:3229-36 (1991).
Zackrisson, B. et al. "A Systematic Overview of Radiation Therapy Effects in Head and Neck Cancer." *Acta Oncologica* 43(5/6):443-61 (2003).
Zhang et al. "Bioreduction activated prodrugs of camptothecin: molecular design, synthesis, activation mechanism and hypoxia selective cytotoxicity." Organic &Biomolecular Chemistry (2005) 3(10):1905-1910, XP002591961.

(56) References Cited

OTHER PUBLICATIONS

Zhao, R. et al. "Synthesis, topoisomerase I inhibitory activity and in vitro cytotoxicity of camptothecin derivatives bearing five-membered heterocycle containing 10-substituents." *Anti-Cancer Drug Design* 13:145-57 (1998).
Zu, Y.-G. et al. "Synthesis and cytotoxicity of water soluble quarternary salt derivatives of camptothecin." *Bioorg. Med. Chem. Lett*. 14:4023-6 (2004).
Zunino, F. et al. "Camptothecins in clinical development." *Expert Opin. Investig. Drugs* 13(3):269-84 (2004).

CAMPTOTHECIN DERIVATIVES AS CHEMORADIOSENSITIZING AGENTS

CROSS-REFERENCE TO RELATED APPLICATIONS

This application is a continuation patent application of U.S. patent application Ser. No. 11/444,150, now U.S. Pat. No. 7,875,602, filed May 30, 2006, which claims priority to provisional application U.S. Ser. No. 60/728,924, filed Oct. 21, 2005, both of which are incorporated herein by reference in their entirety.

FIELD OF THE INVENTION

The present invention relates generally to using certain camptothecin-based compounds that are useful for treating various cancers, particularly in combination with radiotherapy.

BACKGROUND OF THE INVENTION

Cancer is the second leading cause of death in the U.S. and accounts for the deaths of 1 of every 4 Americans. The American Cancer Society estimates that 556,000 Americans died from cancer in 2003. Cancer therapy is presently based on three different approaches, namely chemotherapy, radiation therapy (i.e. radiotherapy) and surgery. Radiotherapy is often used as adjuvant or secondary treatment following surgical procedures to remove a cancerous tumor or in combination with chemotherapy.

The radiotherapeutic approach to eradicating malignant cells found in cancerous tumors was first introduced during the late 1800s and is currently used with curative intent or for palliation in approximately half of all cancer patients. Radiotherapy remains a component of the standard of care for most locally advanced solid tumors. Local recurrence remains a major obstacle to achieving cure of many locally advanced solid tumors treated with definitive radiation therapy. This local recurrence translates directly into poor likelihood of long-term survival.

The ability of radiation therapy to eradicate malignant cells critically depends upon the intratumoral content of molecular oxygen, a potent radiosensitizer involved in mediating DNA damage. The microenvironment of solid tumors is hypoxic compared with normal tissue, and this hypoxia is associated with decreased radiosensitivity. Recent preclinical data suggest that intratumoral hypoxia, particularly in conjunction with an acid microenvironment, may be directly or indirectly mutagenic. Investigations of the prognostic significance of the pretreatment oxygenation status of tumors in patients with head and neck or cervical cancer have demonstrated that increased hypoxia, typically designated in these studies as $pO_2$ levels below 2.5-10 mm Hg, is associated with decreased local tumor control and higher rates of disease and lower overall survival. Hypoxia-directed therapies in the radiation oncology setting include treatment using hyperbaric oxygen, fluosol infusion, carbogen breathing, and electron-affinic and hypoxic-cell sensitizers.

The most well-studied, hypoxia-directed strategy for cancer treatment is the use of electron-affinic radiosensitizers, which mimic the actions of oxygen but are more slowly metabolized. During the past 2 decades, the nitroimidazole compounds misonidazole, nimorazole, and etanidazole have been extensively evaluated by the Radiation Therapy Oncology Group (RTOG) and the Danish Association of Head and Neck Cancer (DAHANCA) as adjuncts to radiation therapy in carcinomas of the head and neck, cervix, and lung (Grigsby et al. Int J Radiat Oncol Biol Phys 1999; 44:513-517; Lee et al. Int J Radiat Oncol Biol Phys 1989; 16:465-470; Lee et al. Int J Radiat Oncol Biol Phys 1995; 32:567-576; Overgaard et al. Int Radiat Oncol Biol Phys 1989; 16:1069-1072; Overgaard et al. Int J Radiat Oncol Biol Phys 1989; 16:1065-1068; Overgaard Int J Radiat Biol 1989; 56:801-811; Overgaard et al. Radiother Oncol 1998; 46:135-146; Wasserman et al. Radiother Oncol 1991; 20(suppl 1):129-135. Most of these studies reported disappointing local control and survival outcomes, but a few recent studies appear to support the use of nitroimidazole compounds with radiation therapy. Other cancer treatment protocols currently employ radiosensitizers activated by ionizing radiation, e.g., X-rays. Examples of X-ray-activated radiosensitizers include, but are not limited to, the following: metronidazole, desmethylmisonidazole, pimonidazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same.

Some therapeutic compounds, which are known as being cytotoxic per se, hence susceptible of being used in the therapy of cancer, are also endowed with radiosensitization activity as they are capable of inducing DNA radiation damage in response to ionizing radiation. So far, the possibility of combining both cytotoxic agents, e.g. a given radiosensitizer and radiotherapy, with the expectation of getting a supra-additive antitumor effect in comparison to the single cytotoxic alone, is of utmost importance in cancer therapy. Among the several compounds endowed with antitumor activity and also known as possessing radiosensitization activity see, for instance, cisplatin, gemcitabine, navelbine, tomudex, nicotinamide, paclitaxel, docetaxel, simvastatin and topotecan.

We have now discovered that the chemotherapeutic activity of certain camptothecin (CPT) derivatives is enhanced by appending various electronic-affinic groups to provide a single compound for use as a chemoradiosensitizer. The compounds of the invention are considerably less toxic than camptothecin and topotecan. This invention defines a new series of radiosensitizing camptothecin derivatives that are useful for treating various types of cancer. We have also discovered that certain known CPT derivatives are useful in the process of sensitizing a subject's tumor cells to radiation, wherein the process comprises administering a CPT derivative to a subject and then exposing the tumor cells in the subject to radiation.

SUMMARY OF THE INVENTION

One aspect of the invention provides methods of sensitizing tumor cells in a subject to radiation, said method comprising a) administering to the subject in need thereof a camptothecin-based compound comprising one or more radiosensitizing electron-affinic groups; and b) exposing the tumor cells in the subject to a unit dose of radiation.

Another aspect of the invention provides methods of sensitizing tumor cells to radiation, said method comprising: a) administering to a human or animal subject in need thereof a compound or a pharmaceutically acceptable salt thereof having formula (I), below, and b) exposing the subject to a unit dose of ionizing radiation. Preferably, steps a) and b) are applied according to a treatment schedule effective to produce a synergistic anti-neoplastic effect.

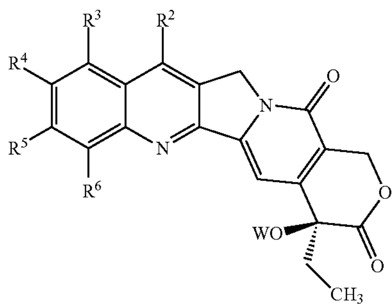

wherein W is alkyl-C(O)—, or $R^1$Y-L-C(O)—, provided that when W is alkyl-C(O)—, at least one of $R^2$, $R^3$, $R^4$, $R^5$, or $R^6$ is nitro;

- L is a bond or linear alkylene (1-8) group, optionally substituted with lower alkyl or substituted lower alkyl, wherein one or two methylene (—$CH_2$—) units of the linear alkylene group is optionally replaced with O, S or NH;
- Y is ═NO—, —N(H)O—, ═N—, —NR—, O, S, or a bond;
- R is H, alkyl, or substituted alkyl;
- $R^1$ is optionally substituted carbocyclic, heterocyclic, or fused 2-, 3- or 4-ring heterocyclic;
- $R^2$ is hydrogen, halo, lower alkyl, lower alkoxy, hydroxy, $R^Q$Y, $R^Q$Y-L-C(O)O—, cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkoxycarbonyloxy, sugar, phosphosugar, O-quinone, substituted lower alkyl aminomethyl, lower alkylcarbonylamino, lower alkylcarbonyloxy methyl, optionally substituted lower alkylcarbonyloxy methyl, substituted vinyl, 1-hydroxy-2-nitroethyl, alkoxycarbonylethyl, aminocarbonyl, alkylcarbonyl, benzoylmethyl, benzylcarbonyloxymethyl, lower alkyliminomethyl or lower alkoxymethyl;
- $R^3$ is hydrogen, halo, lower alkyl, lower alkoxy, hydroxy, $R^Q$Y-L-C(O)O—, cyano, nitro, amino, halogenated lower alkyl, halogenated lower alkoxy, hydroxycarbonyl, formyl, lower alkoxycarbonyl, $CH_2NR^7R^8$ (where each of $R^7$ and $R^8$ is independently H, alkyl of 1-6 carbons, optionally substituted phenyl, hydroxy lower alkyl, amino lower alkyl, or mono- or dialkylamino lower alkyl, or $R^7$ and $R^8$ taken together with —N— represent a cyclic amino-), $CH_2R^9$ (where $R^9$ is lower alkoxy, cyano, amino lower alkoxy, mono- or di-lower alkylamino lower alkoxy, lower alkylthio, amino lower alkylthio, or mono- or di-lower alkylamino lower alkylthio), $NR^{10}R^{11}$ (where each of $R^{10}$ and $R^{11}$ is independently hydrogen, lower alkyl, phenyl, hydroxy lower alkyl, or amino lower alkyl, or $R^{10}$ and $R^{11}$ taken together with —N— represent a cyclic amino), trialkylsilyl, dialkylamino alkyl, lower alkylcarbonyloxy, lower alkoxycarbonyloxy, sugar, phosphosugar, O-quinone, substituted lower alkyl aminomethyl, or lower alkylcarbonylamino or $R^3$ together with $R^4$ is furan, dihydrofuran or 1,4-oxazine-2-one; and
- $R^4$ is hydrogen, halo, lower alkyl, lower alkoxy, hydroxy, $R^Q$Y-L-C(O)O—, cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, lower alkoxycarbonyloxy, sugar, phosphosugar, O-quinone, substituted lower alkyl aminomethyl, or lower alkylcarbonylamino, or $R^4$ together with $R^3$ is furan, dihydrofuran or 1,4-oxazine-2-one, or $R^4$ together with $R^5$ is methylenedioxy;
- $R^5$ is hydrogen, halo, lower alkyl, lower alkoxy, hydroxy, $R^Q$Y-L-C(O)O—, cyano, nitro, amino, trialkylsilyl, halogenated lower alkyl, halogenated lower alkoxy, hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino, or $R^5$ together with $R^4$ is methylenedioxy;
- $R^6$ is hydrogen, halo, lower alkyl, lower alkoxy, hydroxy, $R^Q$Y-L-C(O)O—, cyano, nitro, amino, halogenated lower alkyl, halogenated lower alkoxy, hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino; and
- $R^Q$ is optionally substituted carbocyclic, heterocyclic, or fused 2-, 3- or 4-ring heterocyclic.

Another aspect of the invention provides compounds of formula (II), below:

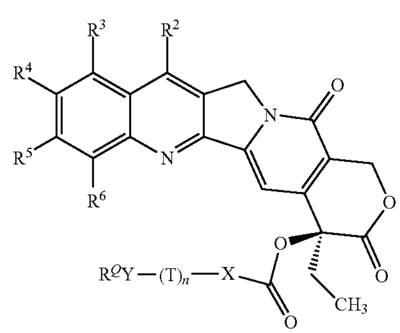

wherein

- X is a O, S, —NR—, or a covalent bond;
- Y is ═NO—, —N(H)O—, ═N—, —NR—, O, S, or a covalent bond;
- T is independently CRR';
- each of R and $R^1$ is independently selected from hydrogen, $alkyl_{1-4}$, and substituted $alkyl_{1-4}$;
- n is an integer from 0 to 8;
- $R^1$ is optionally substituted carbocyclic, heterocyclic, or fused 2-, 3- or 4-ring heterocyclic;
  - provided that when X is a bond, Y is ═NO—, —N(H)O—, ═N— or S;
- $R^2$ is hydrogen, halo, lower alkyl, lower alkoxy, hydroxy, $R^Q$Y-L-C(O)O—, cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkoxycarbonyloxy, sugar, phosphosugar, O-quinone, substituted lower alkyl aminomethyl, lower alkylcarbonylamino, lower alkylcarbonyloxy methyl, optionally substituted lower alkylcarbonyloxy methyl, substituted vinyl, 1-hydroxy-2-nitroethyl, alkoxycarbonylethyl, aminocarbonyl, alkylcarbonyl, alkylcarbonyloxymethyl, benzoylmethyl, benzylcarbonyloxymethyl, lower alkyliminomethyl or lower alkoxymethyl;

$R^3$ is hydrogen, halo, lower alkyl, lower alkoxy, hydroxy, $R^Q$Y-L-C(O)O—, cyano, nitro, amino, halogenated lower alkyl, halogenated lower alkoxy, hydroxycarbonyl, formyl, lower alkoxycarbonyl, $CH_2NR^7$, $R^8$ (where each of $R^7$ and $R^8$ is independently H, alkyl of 1-6 carbons, optionally substituted phenyl, hydroxy lower alkyl, amino lower alkyl, or mono- or dialkylamino lower alkyl, or $R^7$ and $R^8$ taken together with —N— represent a cyclic amino-), $CH_2R^9$ (where $R^9$ is lower alkoxy, CN, amino lower alkoxy, mono- or di-lower alkylamino lower alkoxy, lower alkylthio, amino lower alkylthio, or mono- or di-lower alkylamino lower alkylthio), $NR^{10}R^{11}$ (where each of $R^{10}$ and $R^{11}$ is independently hydrogen, lower alkyl, phenyl, hydroxy lower alkyl, or amino lower alkyl, or $R^{10}$ and $R^{11}$ taken together with —N— represent a cyclic amino), trialkylsilyl, dialkylamino alkyl, lower alkylcarbonyloxy, lower alkoxycarbonyloxy, sugar, phosphosugar, O-quinone, substituted lower alkyl aminomethyl, or lower alkylcarbonylamino or $R^3$ together with $R^4$ is furan, dihydrofuran or 1,4-oxazine-2-one;

$R^4$ is hydrogen, halo, lower alkyl, lower alkoxy, hydroxy, $R^Q$Y-L-C(O)O—, cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, lower alkoxycarbonyloxy, sugar, phosphosugar, O-quinone, substituted lower alkyl aminomethyl, or lower alkylcarbonylamino, or $R^4$ together with $R^3$ is furan, dihydrofuran or 1,4-oxazine-2-one, or $R^4$ together with $R^5$ is methylenedioxy;

$R^5$ is hydrogen, halo, lower alkyl, lower alkoxy, hydroxy, $R^Q$Y-L-C(O)O—, cyano, nitro, amino, halogenated lower alkyl, halogenated lower alkoxy, hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino;

$R^6$ is hydrogen, halo, lower alkyl, lower alkoxy, hydroxy, $R^Q$Y-L-C(O)O—, cyano, nitro, amino, trialkylsilyl, halogenated lower alkyl, halogenated lower alkoxy, hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino;

L is a bond or linear alkylene (1-8) group, optionally substituted with lower alkyl or substituted lower alkyl, wherein one or two methylene (—$CH_2$—) units of the linear alkylene group is optionally replaced with O, S or NH; and $R^Q$ is optionally substituted carbocyclic, heterocyclic, or fused 2-, 3- or 4-ring heterocyclic.

Another aspect of the invention provides pharmaceutical compositions comprising a compound of formula (I) or (II) as defined above, together with a pharmaceutically acceptable excipient. The invention also provides methods for treating a cancer disorder in a subject having a tumor comprising administering to the human or animal subject such a pharmaceutical composition. In a preferred embodiment, this method further comprising exposing the tumor in the subject to a unit dose of radiation.

Another aspect of the invention provides method of treating a neoplasm comprising: a) administering to a human or animal subject in need thereof a compound or a pharmaceutically acceptable salt thereof having formula (I), as defined above, and b) exposing the subject to a unit dose of ionizing radiation.

Other aspects of this invention will be apparent to one of skill in the art by reviewing the ensuing specification.

DETAILED DESCRIPTION

1. Overview

Figure 1:
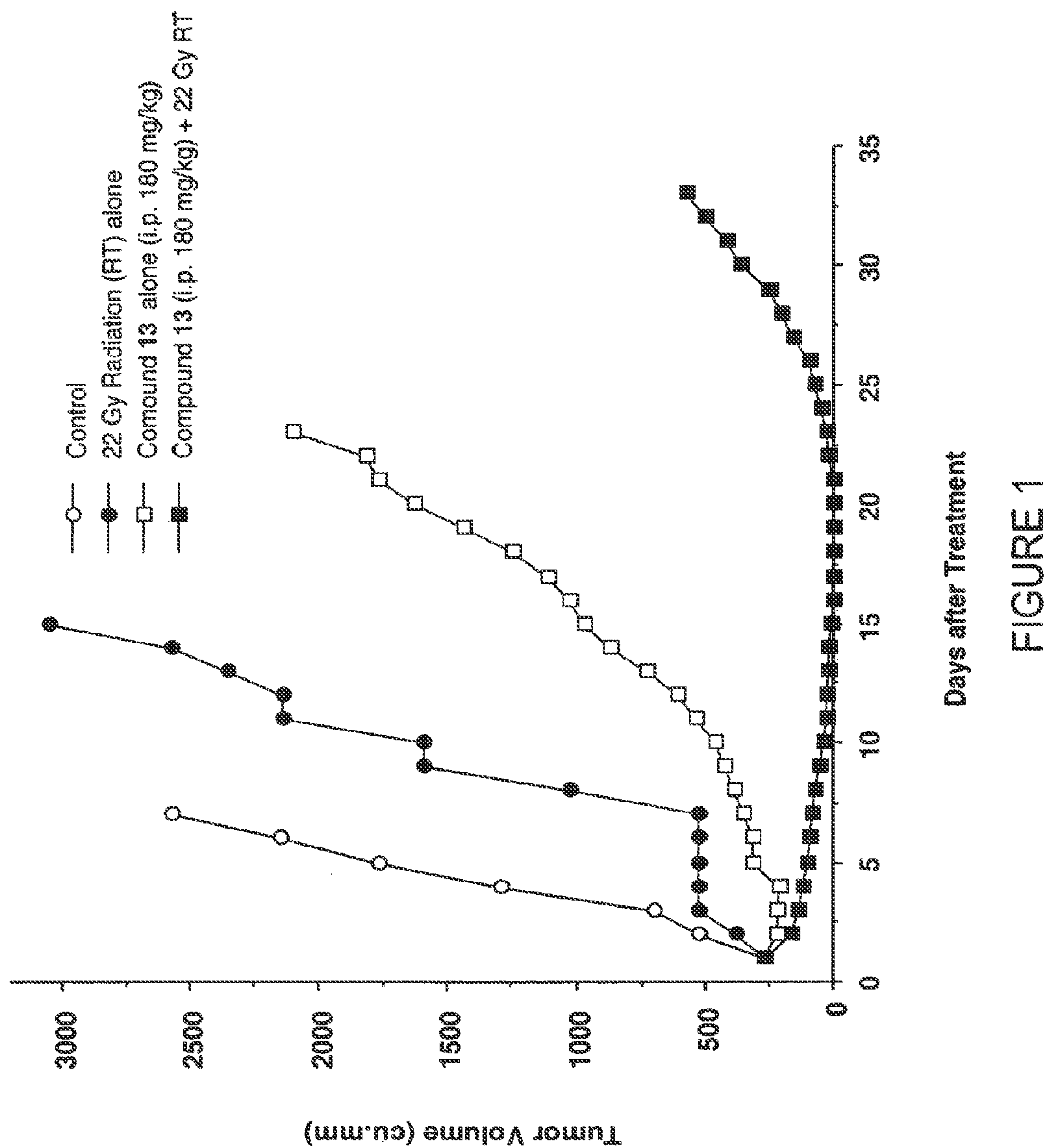
FIG. 1 is a graph depicting in vivo chemoradiosensitizing effect of compound 13 on MTG-B mouse mammary adenocarcinoma tumors, as described in Example 14.

There are several aspects to this invention. One is based on the discovery that certain known camptothecin-based compounds are useful for treating a neoplasm in mammalian subjects by administering such compound to the subjects in combination with radiotherapy, i.e., the treatment of tumors with radioactive substances or radiation from a source external to the subject. Another aspect is based on the discovery that camptothecin-based compounds can be modified by positioning at least one electron-affinic group around the camptothecin structure to enhance their value in combination with radiotherapy. Another aspect of the invention is based on the discovery of certain novel compounds that are useful for treating cancer by administering the novel compounds alone or in combination with radiotherapy. These discoveries lead to other aspects of the invention discussed hereinafter.

2. Definitions

The term "radiosensitizer" refers to a compound or medicament which is capable of increasing the sensitivity of a tumor cell to ionizing radiation, thus improving the likelihood of tumor cell destruction upon exposure to such radiation.

The term "ionizing radiation" is the one conventionally adopted in the therapeutic field of cancer treatment and includes photons having enough energy for chemical bond ionization such as, for instance, α, β and γ rays (also known as alpha, beta, and gamma rays) from radioactive nuclei as well as x-rays. The radiation may be high-LET (linear energy transfer) or low-LET. LET is the energy transferred per unit length of the distance. High LET is said to be densely ionizing radiation and Low LET is said to be sparsely ionizing radiation. Representative examples of high-LET are neutrons and a particles. Representative examples of low-LET are x-ray and γ rays. Low LET radiation including both x-rays and γ rays is most commonly used for radiotherapy of cancer patients. The radiation may be used for external radiation therapy that is usually given on an outpatient basis or for internal radiation therapy that uses radiation that is placed very close to or inside the tumor. In case of internal radiation therapy, the radiation source is usually sealed in a small holder called an implant. Implants may be in the form of thin wires, plastic tubes called cathetres, ribbons, capsules, or seeds. The implant is put directly into the body. Internal radiation therapy may require a hospital stay. The ionizing radiation source is provided as a unit dose of radiation and is preferably an x-ray tube since it provides many advantages, such as convenient adjustable dosing where the source may be easily turned on and off, minimal disposal problems, and the like. A unit dose of radiation is generally measured in gray (Gy). The ionizing radiation source may also comprise a radioisotope, such as a solid radioisotopic source (e.g., wire, strip, pellet, seed, bead, or the like), or a liquid radioisotopic filled balloon. In the latter case, the balloon has been specially configured to prevent leakage of the radioisotopic material from the balloon into the body lumen or blood stream. Still further, the ionizing radiation source may comprise a receptacle in the catheter body for receiving radioisotopic materials like pellets or liquids. The radioisotopic material may be selected to emit α, β and γ radiation. Usually, α and β radiation are preferred since they may be quickly absorbed by surrounding tissue and will not penetrate substantially beyond the wall of the body lumen being treated. Accordingly, incidental irradiation of the heart and other organs adjacent to the treatment region can be substantially eliminated. The total number of units provided will be an amount determined to be therapeutically effective by one skilled in treatment using ionizing radiation. This amount will vary with the subject and the maliganant cells or neoplasm being treated. The amount may vary but a patient may receive a dosage of about 30-75 Gy over several weeks.

The term "anti-neoplastic effect" refers to inhibiting or retarding the growth of a malignant cell, or in the case of a subject having a malignant tumor, the rate of tumor growth is decreased, the volume of such tumor is reduced, or the tumor is eliminated entirely.

The term "electron-affinic" refers to an attraction a moiety has for electrons that causes the affinic moiety to enter into and remain in chemical combination with one or more electrons. Typically an electron-affinic moiety is chemically reducible (i.e. an oxidizing group). Representative electron affinic moieties are presented herein.

"Synergistic," as used herein, means that the therapeutic results from treatment of a neoplasm in a subject with (i) a radiosensitizer in combination with (ii) ionizing radiation are improved over what would be obtained by summing the results of (i) alone with (ii) alone. The improvement may be better anti-neoplastic effect or other beneficial results.

The term "CPT" is an abbreviation for camptothecin, also known as (S)-4-ethyl-4-hydroxy-1-pyrano-[3',4':6,7]indolizino[1,2-b]quinoline-3,14(4H,12H)-dione. The compound is readily available from numerous sources, e.g., Sigma Chemical Co., St. Louis, Mo. The chemical formula of camptothecin and its numbering system are as follows:

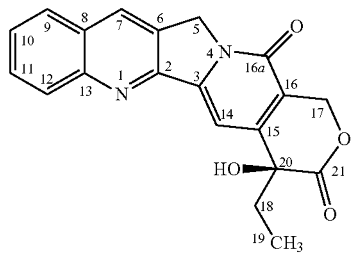 [SMILES: CC[C@@]1(O)C(=O)OCc2c1cc1n(c2=O)Cc2cc3ccccc3nc2-1]

In the structure above and in the rest of the application the wedged bond (for example, the bond showing attachment of hydroxyl group at C20) indicates its attachment to a chiral carbon and is coming out of the plane. Analogously, a dotted bond indicates its attachment to a chiral carbon and it is going into the plane. The compound has a hydroxy at the 20-position that is esterified to make the compounds of this invention.

The term "alkyl" refers to a monovalent, saturated aliphatic hydrocarbon radical having the indicated number of carbon atoms. For example, a "C1-6 alkyl" or an "alkyl of 1-6 carbons" or "Alk 1-6" would refer to any alkyl group containing one to six carbons in the structure. "C1-20 alkyl" refers to any alkyl group having one to twenty carbons. Alkyl may be a straight chain (i.e. linear) or a branched chain. Lower alkyl refers to an alkyl of 1-6 carbons. Representative examples of lower alkyl radicals include methyl, ethyl, n-propyl, n-butyl, n-pentyl, n-hexyl, isopropyl, isobutyl, isopentyl, amyl, sec-butyl, tert-butyl, tert-pentyl and the like. Higher alkyl refers to alkyls of seven carbons and above. These include n-heptyl, n-octyl, n-nonyl, n-decyl, n-dodecyl, n-tetradecyl, n-hexadecyl, n-octadecyl, n-eicosyl, and the like, along with branched variations thereof. The radical may be optionally substituted with substituents at positions that do not significantly interfere with the preparation of compounds falling within the scope of this invention and that do not significantly reduce the efficacy of the compounds. The alkyl is optionally substituted with one to five substituents independently selected from the group consisting of halo, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, and lower alkylcarbonylamino.

The term "Alkylene" refers to divalent saturated aliphatic hydrocarbyl groups preferably having from 1 to 8 carbon atoms that are either straight-chained (linear) or branched. This term is exemplified by linear groups such as methylene ($—CH_2—$), ethylene ($—CH_2CH_2—$), n-propylene ($—CH_2CH_2CH_2—$) and branched groups such as iso-propylene ($—CH_2CH(CH_3)—$) or ($—CH(CH_3)CH_2—$) and the like.

The term "alkoxy" refers to a monovalent radical of the formula RO—, where R is an alkyl as defined herein. Lower alkoxy refers to an alkoxy of 1-6 carbon atoms, with higher alkoxy is an alkoxy of seven or more carbon atoms. Representative lower alkoxy radicals include methoxy, ethoxy, n-propoxy, n-butoxy, n-pentyloxy, n-hexyloxy, isopropoxy, isobutoxy, isopentyloxy, amyloxy, sec-butoxy, tert-butoxy, tert-pentyloxy, and the like. Higher alkoxy radicals include those corresponding to the higher alkyl radicals set forth herein. The radical may be optionally substituted with substituents at positions that do not significantly interfere with the preparation of compounds falling within the scope of this invention and that do not significantly reduce the efficacy of the compounds. The alkoxy is optionally substituted with one to five substituents independently selected from the group consisting of halo, lower alkyl, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, and lower alkylcarbonylamino.

The term "cycloalkyl" refers to a monovalent, alicyclic, saturated hydrocarbon radical having three or more carbons forming the ring. While known cycloalkyl compounds may have up to 30 or more carbon atoms, generally there will be three to seven carbons in the ring. The latter include, for example, cyclopropyl, cyclobutyl, cyclopentyl, cyclohexyl, and cycloheptyl. The radical may be optionally substituted with substituents at positions that do not significantly interfere with the preparation of compounds falling within the scope of this invention and that do not significantly reduce the efficacy of the compounds. The cycloalkyl is optionally substituted with one to five substituents independently selected from the group consisting of halo, lower alkyl, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, and lower alkylcarbonylamino.

The term "hydroxycarbonyl" is a monovalent radical having the formula —C(O)OH.

The term "lower alkoxycarbonyl" is a monovalent radical having the formula —C(O)OAlk, where Alk is lower alkyl.

The term "lower alkoxycarbonyloxy" is a monovalent radical having the formula —OC(O)OAlk, where Alk is lower alkyl.

The term "sugar" refers to a monovalent radical formed by removal of a hydrogen from any hydroxy group of a monsaccharide, disaccharide, oligosaccharide or polysaccharide. The monosaccharide unit that is a part of a disaccharide, oligosaccharide or polysaccharide may be a D or L isomer existing as a five-membered cyclic form (furanose) or a 6-membered cyclic form (pyranose). Representative examples of monosaccharides include glucose, fructose, mannose, and galactose. Representative examples of disaccharides include lactose, maltose, and sucrose. Oligosaccharides may contain 3-20 monosaccharide units linked together, more preferably 3-15 monosaccharide units linked together. Representative examples of oligosaccharides include maltotetraose and cyclodextrin. Representative examples of polysaccharides include amylose. starch and cellulose.

The term "phosphosugar" refers to a monovalent radical formed by removal of a hydrogen from any hydroxy group of either a monsaccharide or a phosphoric acid wherein the monosaccharide is linked to the phosphoric acid via an ether linkage The monosaccharide may be a D or L isomer existing as a five-membered cyclic form (furanose) or a 6-membered cyclic form (pyranose). Representative examples of monosaccharides are set forth above.

The term "lower alkylcarboxyloxy" is a monovalent radical having the formula —OC(O)Alk, where Alk is lower alkyl.

The term "lower alkylcarbonylamino" is a monovalent radical having the formula —NHC(O)Alk, where Alk is lower alkyl.

The term "substituted lower alkyl aminomethyl" is a monovalent radical having the formula —$CH_2$NHAlk, where Alk is a substituted lower alkyl. Representative examples of substituted lower alkyl aminomethyl include (tris(hydroxymethyl)methylamino)methyl, (bis(hydroxymethyl)methylamino)methyl, and (2-hydroxyethylamino)methyl.

A "halo" substitutent is a monovalent halogen radical chosen from chloro, bromo, iodo, and fluoro. A "halogenated" compound is one substituted with one or more halo substituents. Chloro is generally preferred.

A "1-naphthyl" or "2-naphthyl" is a radical formed by removal of a hydrogen from the 1- or 2-position of a naphthalene structure, respectively. It is optionally substituted with from one to four substituents independently selected from the group consisting of halo, lower alkyl, lower alkoxy, hydroxy, cyano, nitro, phenyl, amino, halogenated lower alkyl, formyl, halogenated lower alkoxy, hydroxycarbonyl, lower alkoxycarbonyl, lower alkylcarbonyloxy, and lower alkylcarbonylamino.

A "phenyl" is a radical formed by removal of a hydrogen from a benzene ring. The phenyl is optionally substituted with from one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino.

A "cyclic amino" is a monovalent radical of a saturated 5-, 6-, or 7-membered cyclic amine ring having no more than one additional hetero atom such as nitrogen, oxygen, or sulfur. Representative examples include, e.g., 1-pyrrolidino, 1-piperidino, morpholino, piperazino, and the like. These may be substituted or unsubstituted. If substituted, generally they will have no more than 2 substituents chosen from lower alkyl, lower cycloalkyl, hydroxy lower alkyl, phenyl (substituted or unsubstituted), benzyl (substituted or unsubstituted), aminocarbonylmethyl, lower alkylaminocarbonylmethyl, amino, mono- or di-lower alkylamino, or cyclic amino.

"Monovalent radical" refers to attachment of the radical via a single bond.

"Divalent radical" refers to attachment of the radical via a double bond.

"Heteroatom" refers to nitrogen, oxygen, sulfur, or any oxidized form of nitrogen or sulfur.

"Cyano" refers to a monovalent —CN radical.

"Nitro" refers to a monovalent —$NO_2$ radical.

"Amino" refers to a monovalent —$NH_2$ radical.

"Formyl" refers to a monovalent —CHO radical.

"Tri loweralkylsilyl" refers to a monovalent silyl radical substituted with three loweralkyl groups, where the lower alkyl groups may be the same or different.

"Loweralkylcarbonyloxy methyl" refers to a monovalent —$CH_2$C(O)(loweralkyl) radical.

"Substituted vinyl" refers to a substituted —CH═$CH_2$ group were one or more the CH groups are replaced with one to three substituents independently selected from the group consisting of alkyl, halo, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, and lower alkylcarbonylamino.

"Hydroxy" refers to a monovalent OH radical.

"Carbocyclic" refers to a 3-18 membered ring monovalent or divalent radical where all the ring atoms are carbon and may be fully saturated, partially saturated, or unsaturated (i.e. aromatic in nature). The carbocyclic radical is bonded through a saturated, partially saturated, or unsaturated ring via a single or double bond. Carbocyclic groups may be fused, containing 2, 3, or 4 rings where the fused rings are independently saturated, partially saturated, or unsaturated. Examples of carbocyclic groups include phenyl, naphthyl, fluorenyl, and tetracenyl. The radical may be optionally substituted with substituents at positions that do not significantly interfere with the preparation of compounds falling within the scope of this invention and that do not significantly reduce the efficacy of the compounds. The radical is optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, lower alkylcarbonylamino, sugar and phosphosugar.

A "carbamoyloxy" is a monovalent radical of the formula $R_{13}R_{14}$NC(O)O— (i.e. an aminocarbonyloxy) where $R_{13}$ and $R_{14}$ together form a cyclic amino with the nitrogen atom, or each of $R_{13}$ and $R_{14}$ is independently hydrogen, lower alkyl, hydroxy lower alkyl, amino lower alkyl, lower cycloalkyl, phenyl (substituted or unsubstituted), or benzyl (substituted or unsubstituted). Examples include aminocarbonyloxy, methylaminocarbonyloxy, dimethyl aminocarbonyloxy, [4-(1-piperidino)-1-piperidino]carbonyloxy, 1-morpholinocarbonyloxy, 1-pyrrolidinyl, 1-piperazinecarbonyloxy, and others recognized by one skilled in the art or delineated herein.

"Heterocyclic" is a monovalent or divalent radical of a 3-10 membered ring group containing at least one heteroatom in the ring and may be fully saturated, partially saturated, or unsaturated (i.e. aromatic in nature). The heterocycle is bonded through a carbon atom or heteroatom via a single or double bond. The heteroatom in the heterocycle such as N can optionally exist as an N-oxide or S can optionally exist as a sulfoxide or a sulfone.

A "5-membered heterocyclic ring" is a monovalent or a divalent radical of a 5-membered ring containing at least one heteroatom in the ring and may be fully saturated, partially saturated, or unsaturated (i.e. aromatic in nature). Generally the heterocycle will contain no more than two hetero atoms. The heterocycle is bonded through a carbon atom or heteroatom via a single or double bond. Representative examples of unsaturated 5-membered heterocycles with only one hetero atom include 2- or 3-pyrrolyl, 2- or 3-furanyl, and 2- or 3-thiophenyl. Corresponding partially saturated or fully saturated radicals include 3-pyrrolin-2-yl, 2- or 3-pyrrolidinyl, 2- or 3-tetrahydrofuranyl, and 2- or 3-tetrahydrothiophenyl. Representative unsaturated 5-membered heterocyclic radicals having two hetero atoms include imidazolyl, oxazolyl, thiazolyl, pyrazolyl, and the like. The corresponding fully saturated and partially saturated radicals are also included. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, lower alkylcarbonylamino, sugar and phosphosugar.

A "6-membered heterocyclic ring" is a monovalent or a divalent radical of a 6-membered ring containing at least one heteroatom and may be fully saturated, partially saturated, or unsaturated (i.e. aromatic in nature). Generally the heterocycle will contain no more than two hetero atoms. The heterocycle is bonded through a carbon atom or heteroatom via a single or double bond. Representative examples of unsaturated 6-membered heterocycles with only one hetero atom include 2-, 3-, or 4-pyridinyl, 2H-pyranyl, and 4H-pyranyl. Corresponding partially saturated or fully saturated radicals include 2-, 3-, or 4-piperidinyl, 2-, 3-, or 4-tetrahydropyranyl and the like. Representative unsaturated 6-membered heterocyclic radicals having two hetero atoms include 3- or 4-pyridazinyl, 2-, 4-, or 5-pyrimidinyl, 2-pyrazinyl, and the like. The corresponding fully saturated and partially saturated radicals are also included, e.g. 2-piperazine. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, lower alkylearbonylamino, sugar and phosphosugar.

A "fused 2-, 3-, or 4-ring heterocyclic" is a monovalent or a divalent radical that is polynuclear in that the adjacent rings share a pair of atoms, generally carbon atoms. At least one of the rings will be heterocyclic in that it will have a noncarbon atom such as nitrogen, oxygen, or sulfur. The ring system may contain from 9 to 18 atoms. The heterocycle is bonded through a carbon atom or heteroatom of one of the rings via a single or double bond. A 2-ring heterocyclic system will generally have 9 or 10 atoms included in the ring. Examples of such a 2-ring system include quinoline, isoquinoline, purine, indolizine, 4H-quinolizine, 3H-pyrrolizine, coumaran, coumarin, isocoumarin, 4-methylcoumarin, 3-chloro-H-methylcoumarin, chromone, benzofuran, benzothiophene, benzothiazole, indole, and the like. A 3-ring system will generally have 12 to 14 atoms included in the ring. Examples of such a 3-ring system include carbazole, acridine, and the like. A 4-ring fused system will generally have 16 to 18 atoms included in the chain. Examples of such a 4-ring system include isothebaine and the like. The radical may be optionally substituted with substituents at positions that do not significantly interfere with the preparation of compounds falling within the scope of this invention and that do not significantly reduce the efficacy of the compounds. The radical is optionally substituted with one to five substituents independently selected from the group consisting of halo, lower alkyl, lower alkoxy, hydroxy, cyano, nitro, phenyl, amino, halogenated lower alkyl, halogenated lower alkoxy, hydroxycarbonyl, lower alkoxycarbonyl, lower alkylcarbonyloxy, lower alkylcarbonylamino, sugar and phosphosugar.

Other chemical terms are given their standard meaning as understood by one of skill in the art with guidance from standard texts and dictionaries. Under standard nomenclature used throughout this disclosure, the terminal portion of the substituent is described first, followed by adjacent functionality toward the point of attachment. Thus, for example, a "aminocarbonyl" group refers to a —C(O)$NH_2$ group, a "loweralkoxymethyl" group refers to a —$CH_2$(loweralkoxy) group, a "amino lower alkoxy" group refers to a-(loweralkoxy)amino group, etc.

3. Method of Treatment of the Invention a. Types of Cancer Treated

This invention relates to the treatment of cancer. More specifically, the invention is directed to the treatment of a subject, particularly a mammal such as a human, having a neoplasm by administering a therapeutically effective amount of a novel compound of formula (II) to the subject for a period of time sufficient to produce an anti-neoplastic result. The treatment may optionally include the step of directing ionizing radiation to the neoplasm. The neoplasm may also be treated by administering a CPT-based compound as described herein, and exposing the neoplasm to an effective amount of ionizing radiation, i.e. at least a unit dose.

The term cancer is to be considered in the broadest general definition as a malignant neoplasm, an abnormal mass of tissue, the growth of which exceeds and is uncoordinated with that of normal tissues and persists in the same excessive manner after cessation of the stimuli that evoked the change. It might be added that the abnormal mass is purposeless, preys on the host, and is virtually autonomous. A cancer can also be considered as a malignant tumor. A further discussion of neoplasia is found at "Robbins Pathologic Basis of Disease," Sixth Edition, by R. S. Cotran, V. Kumar, and T. Collins, Chapter 8 (W. B. Saunders Company). This information from Chapter 8 is incorporated herein by reference. The following Table 1 provides examples of the types of cancers, i.e., malignant tumors or neoplasia that may be treated by administering a compound of this invention.

TABLE 1

| Tissue of Origin | Malignant |
|---|---|
| Composed of One Parenchymal Cell Type | |
| Mesenchymal tumors | |
| Connective tissue and derivatives | Fibrosarcoma<br>Liposarcoma<br>Chondrosarcoma<br>Osteogenic sarcoma |
| Endothelial and related tissues | |
| Blood vessels | Angiosarcoma |
| Lymph vessels | Lymphangiosarcoma |
| Synovium | Synovial sarcoma |

TABLE 1-continued

| Tissue of Origin | Malignant |
|---|---|
| Mesothelium | Mesothelioma |
| Brain coverings | Invasive meningioma |
| Blood cells and related cells | |
| Hematopoietic cells | Leukemias |
| Lymphoid tissue | Malignant lymphomas |
| Muscle | |
| Smooth | Leiomyosarcoma |
| Striated | Rhabdomyosarcoma |
| Epithelial tumors | |
| Stratified squamous | Squamous cell or epidermoid carcinoma |
| Basal cells of skin or adnexa | Basal cell carcinoma |
| Epithelial lining | |
| Glands or ducts | Adenocarcinoma |
| | Papillary carcinoma |
| | Cystadenocarcinoma |
| Respiratory passages | Bronchogenic carcinoma |
| | Bronchial adenoma (carcinoid) |
| Neuroectoderm | Malignant melanoma |
| Renal epithelium | Renal cell carcinoma |
| Liver cells | Hepatocellular carcinoma |
| Urinary tract epithelium (transitional) | Transitional cell carcinoma |
| Placental epithelium (trophoblast) | Choriocarcinoma |
| Testicular epithelium (germ cells) | Seminoma |
| | Embryonal carcinoma |
| More Than One Neoplastic Cell-Mixed Tumors, Usually Derived From One Germ Layer | |
| Salivary glands | Malignant mixed tumor of salivary gland origin |
| Breast | Malignant cystosarcoma phyllodes |
| Renal anlage | Wilms tumor |
| More Than One Neoplastic Cell Type Derived From More Than One Germ Layer-Teratogenous | |
| Totipotential cells in gonads or in embryonic rests | Immature teratoma, teratocarcinoma |

b. Treatment with Drug Alone

The novel compounds of the invention are thus useful in the treatment of a neoplasm, e.g. leukemia and solid tumors, such as colon, colo-rectal, ovarian, mammary, prostate, lung, kidney and also melanoma tumors. The dosage range adopted will depend on the route of administration and on the age, weight and condition of the patient being treated. The compounds may be administered, for example, by the parenteral route, for example, intramuscularly, intravenously or by bolus infusion.

As used herein, a patient or subject is a vertebrate having cancer or other diseases. Preferably, the subject is a warm-blooded animal, particularly a mammal which includes both human and non-human mammals. Examples of non-human mammals include but are not limited to farm animals, such as cows, sheep, pigs, goats, horses, and llama, and pets, such as dogs and cats. More preferably, the subject is a human. The compounds are shown herein as Formula II and are described in more detail hereinafter. For this aspect of the invention, a therapeutically effective amount of the compound is administered to a subject in need thereof for a period of time sufficient to obtain an antineoplastic effect.

With mammals, including humans, the effective amounts can be administered on the basis of body surface area. The interrelationship of dosages varies for animals of various sizes and species, and for humans (based on mg/m$^2$ of body surface) is described by E. J. Freireichet al., Cancer Chemother. Rep., 50(4):219 (1966). Body surface area may be approximately determined from the height and weight of an individual (see, e.g., Scientific Tables, Geigy Pharmaceuticals, Ardsley, N.Y. pp. 537-538 (1970)). A suitable dose range is from 1 to 1000 mg of equivalent per m$^2$ body surface area of a compound of the invention, for instance from 50 to 500 mg/m$^2$.

c. Treatment with Drug and Radiotherapy

Another aspect of this invention is a method of treating a neoplasm in a subject, which method comprises a) administering to the subject a compound of formula (I) as described herein, and b) exposing the subject's neoplasm to ionizing radiation. The compound is generally administered in combination with pharmaceutically acceptable excipient in accordance with a treatment schedule.

As used herein, the term "treatment schedule" refers to the amount, order and timing in which the subject is administered a camptothecin-based compound and exposed to a unit dose of ionizing radiation. The drug administration and radiation exposure may not necessarily be carried out sequentially. Radiation exposure can be carried out after a single dose or after multiple doses of a camptothecin-based compound in order to get the optimum results. For all of the administering routes, the exact timing of administration of the dosages as well as exposure to radiation can be varied to achieve optimal results. Generally, if using Intralipid 20 as the carrier for the CPT derivative, the actual dosage of CPT derivative reaching the patient will be less. This is due to some loss of the CPT derivative on the walls of the syringes, needles and preparation vessels, which is prevalent with the Intralipid 20 suspension. When a carrier, such as cottonseed oil is used, this above described loss is not so prevalent because the CPT derivative does not adhere as much to the surface of syringes, etc. One of skill in the art would routinely alter the amounts in view of such loss of drug to syringe walls, etc.

Another important feature of the method provided by the present invention relates to the relatively low apparent overall toxicity of the CPT derivatives administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

Another aspect of this invention is a method for treating cancer in a warm-blooded animal, which method comprises administering a therapeutically effective amount of a compound of the invention as defined herein. A compound useful in this invention is administered to an appropriate subject in need of these compounds in a therapeutically effective dose by a medically acceptable route of administration such as orally, parentally (e.g., intramuscularly, intravenously, subcutaneously, interperitoneally), transdermally, rectally, by inhalation and the like.

Another aspect of this invention is the use of a camptothecin-based compound, as identified herein, for the preparation of a pharmaceutical for the treatment of a neoplasm in a subject in combination with radiotherapy.

d. Sensitizing Cells

One aspect of the invention is a method of sensitizing tumor cells to radiation, said method comprising: a) administering to a human or animal subject in need thereof a compound comprising a camptothecin derivative comprising one or more radiosensitizing electron-affinic groups; and b) exposing said subject to a unit dose of radiation. In some embodiments, steps a) and b) are applied according to a treatment schedule effective to produce a synergistic antineoplastic effect. Preferably at least one of the radiosensitizing electron-affinic groups is a nitro-substituted carbocyclic or a nitro-substituted heterocyclic aromatic moiety that is attached to the C5, C7, C9, C10, C11, C12 or C20 position of the CPT. The radio sensitizing compounds of the present invention are prepared by linking the "electron-affinic group" to the C5, C7, C9, C10, C11, C12 or C20 carbons of the core of the camptothecin derivative. The length and nature of the linker between the camptothecin and the "electron-affinic group" may be altered. In some embodiments, the carbocyclic or heterocyclic moiety is aromatic and is preferably at the C7, C9, C10, C11, C12 or C20 position. In some preferred embodiments, the carbocyclic or heterocyclic moiety is (+) or (+2-(2,4,5,7-tetranitro-9-fluorenylideneaminooxy)-propionic acid (TAPA) or 2-(2,4,5,7-tetranitro-9-fluorenylidene-aminooxy)-ethanoic acid.

Radiosensitizers by definition increase the sensitivity of cancerous cells to the toxic effects of ionizing radiation. While not wanting to be limited to any particular theory, several mechanisms for the mode of action of radiosensitizers have been suggested. Hypoxic cell radiosensitizers (e.g., 2-nitroimidazole compounds, and benzotriazine dioxide compounds) promote reoxygenation of hypoxic tissue and/or catalyze generation of damaging oxygen radicals. Nonhypoxic cell radiosensitizers (e.g., halogenated pyrimidines) can be analogs of DNA bases and preferentially incorporate into the DNA of cancer cells and thereby promote the radiation ion-induced breaking of DNA molecules and/or prevent the normal DNA repair mechanisms. Various other potential mechanisms of action have been hypothesized for radiosensitizers in the treatment of disease. A discussion of radiosensitizer agents is provided in Rowinsky-EK, Oncology-Huntingt., October 1999; 13(10 Suppl 5): 61-70; Chen-A Y et al., Oncology-Huntingt. October 1999; 13 (10 Suppl 5): 39-46; Choy-H, Oncology-Huntingt. October 1999; 13 (10 Suppl 5): 23-38; and Herscher-L L et al, Oncology-Huntingt. October 1999; 13 (10 Suppl 5): 11-22.

A method is also provided for killing tumor cells in a warm-blooded animal which includes the steps of administering to the warm-blooded animal a pharmaceutical composition as described above in an amount effective to radiosensitize the tumor cells, followed by, after a time interval sufficient to enhance radiosensitization of the tumor cells, irradiating the tumor cells with a dose of radiation effective to kill the tumor cells.

After administration of the radiosensitizing composition to the tumor cells and the passage of a time interval sufficient to enhance radiosensitization of the tumor cells, the tumor cells are irradiated with a dose of radiation effective to destroy the tumor cells. Generally, the patient will receive a total radiation dosage of about 60 to 76 Gy over seven to eight weeks, each individual radiation dose to be given within approximately 1 to 4 hours after administration of the radiosensitizer. Such sequences of radiosensitization treatments and irradiation are repeated as needed to abate and, optimally, reduce or eliminate, the spread of the malignancy.

Another aspect of the invention provides methods of sensitizing tumor cells to radiation, said method comprising: a) administering to a human or animal subject in need thereof a compound or a pharmaceutically acceptable salt thereof having formula (I), below, and b) exposing the subject to a unit dose of ionizing radiation. In other aspect, this invention provides a method where steps a) and b) are applied to a treatment schedule effective to produce a synergistic antineoplastic effect.

(I)

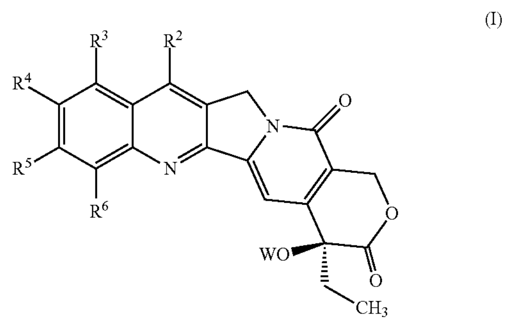

wherein W is alkyl-C(O)—, or $R^1$Y-L-C(O)—, provided that when W is alkyl-C(O)—, at least one of $R^2$, $R^3$, $R^4$, $R^5$, or $R^6$ is nitro;

L is a bond or linear alkylene (1-8) group, optionally substituted with lower alkyl or substituted lower alkyl, wherein one or two methylene (—$CH_2$—) units of the linear alkylene group is optionally replaced with O, S or NH;

Y is ═NO—, —N(H)O—, ═N—, —NR—, O, S, or a bond;

R is H, alkyl, or substituted alkyl;

$R^1$ is optionally substituted carbocyclic, heterocyclic, or fused 2-, 3- or 4-ring heterocyclic;

$R^2$ is hydrogen, halo, lower alkyl, lower alkoxy, hydroxy, $R^{Q}$Y, $R^{Q}$Y-L-C(O)O—, cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkoxycarbonyloxy, sugar, phosphosugar, O-quinone, substituted lower alkyl aminomethyl, lower alkylcarbonylamino, lower alkylcarbonyloxy methyl, optionally substituted lower alkylcarbonyloxy methyl, substituted vinyl, 1-hydroxy-2-nitroethyl, alkoxycarbonylethyl, aminocarbonyl, alkylcarbonyl, benzoylmethyl, benzylcarbonyloxymethyl, lower alkyliminomethyl or lower alkoxymethyl;

$R^3$ is hydrogen, halo, lower alkyl, lower alkoxy, hydroxy, $R^{Q}$Y-L-C(O)O—, cyano, nitro, amino, halogenated lower alkyl, halogenated lower alkoxy, hydroxycarbonyl, formyl, lower alkoxycarbonyl, $CH_2NR^7$, $R^8$ (where each of $R^7$ and $R^8$ is independently H, alkyl of 1-6 carbons, optionally substituted phenyl, hydroxy lower alkyl, amino lower alkyl, or mono- or dialkylamino lower alkyl, or $R^7$ and $R^8$ taken together with —N— represent a cyclic amino-), $CH_2R^9$ (where $R^9$ is lower alkoxy, cyano, amino lower alkoxy, mono- or di-lower alkylamino lower alkoxy, lower alkylthio, amino lower alkylthio, or mono- or di-lower alkylamino lower alkylthio), $NR^{10}R^{11}$ (where each of $R^{10}$ and $R^{11}$ is independently hydrogen, lower alkyl, phenyl, hydroxy lower alkyl, or amino lower alkyl, or $R^{10}$ and $R^{11}$ taken together with —N— represent a cyclic amino), trialkylsilyl, dialkylamino alkyl, lower alkylcarbonyloxy, lower alkoxycarbonyloxy, sugar, phosphosugar, O-quinone, substituted lower alkyl aminomethyl, or lower alkylcarbonylamino or $R^3$ together with $R^4$ is furan, dihydrofuran or 1,4-oxazine-2-one; and $R^4$ is hydrogen, halo, lower alkyl, lower alkoxy, hydroxy, $R^{Q}$Y-L-C(O)O—, cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, lower alkoxycarbonyloxy, sugar, phosphosugar, O-quinone, substituted lower alkyl aminomethyl, or lower alkylcarbonylamino, or $R^4$ together with $R^3$ is furan, dihydrofuran or 1,4-oxazine-2-one, or $R^4$ together with $R^5$ is methylenedioxy;

$R^5$ is hydrogen, halo, lower alkyl, lower alkoxy, hydroxy, $R^Q$Y-L-C(O)O—, cyano, nitro, amino, trialkylsilyl, halogenated lower alkyl, halogenated lower alkoxy, hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino, or $R^5$ together with $R^4$ is methylenedioxy;

$R^6$ is hydrogen, halo, lower alkyl, lower alkoxy, hydroxy, $R^Q$Y-L-C(O)O—, cyano, nitro, amino, halogenated lower alkyl, halogenated lower alkoxy, hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino; and $R^Q$ is optionally substituted carbocyclic, heterocyclic, or fused 2-, 3- or 4-ring heterocyclic.

In some embodiments, W is $R^1$Y-L-C(O)—.

$R^1$ groups that may be incorporated into the active camptothecin derivative as described by Formula (I) include phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperazino, lower alkoxycarbonyl, and lower alkylcarbonylamino; a fused, 2-, 3-, or 4-ring heterocyclic system optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino; 1- or 2-naphthyl optionally substituted with from one to four substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino; or a 5 or 6 membered heterocyclic ring containing one or two nitrogen atoms, which ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino. In a preferred embodiment, $R^1$ is substituted with at least one carbonyl, amido, trifluoromethyl, halogen, nitro, nitroso, sulfonyl, sulfinyl, phosphoryl, or oxo group. In other embodiments, $R^1$ is selected from the group consisting of O-quinone, semiquinone, fluorene, imidazole, triazole, pyridine, benzamide, nicotinamide, benzotriazine oxide, furan, thiophene, oxazole, or thiazole, where each of the aforementioned groups may be substituted or unsubstituted. In other embodiments, $R^1$ is aromatic.

Preferably at least one of $R^1$, $R^2$, $R^3$, $R^4$, $R^5$, or $R^6$ comprises an electron-affinic moiety, wherein the electron-affinic moiety is a (i) nitro; (ii) carbocyclic or heterocyclic aromatic moiety possessing one or more carbonyl, trifluoromethyl, halogen, nitro, sulfonyl, sulfinyl, phosphoryl, oxide or cyano groups; (iii) heterocyclic aromatic moiety containing two or more heteroatoms; (iv) metal complex; or (v) organo-metallic group in which the metal is covalently bonded to carbon.

Carbocyclic or heterocyclic aromatic electron-affinic moieties contain one to three rings with a total of 5 to 15 ring atoms. The heteroatoms are selected from the group consisting of N, S, O and P. Preferably, the carbocyclic or heterocyclic aromatic electron-affinic moieties contain one to two rings with one ring being presently most preferred. Representative carbocyclic aromatic electron-affinic moieties include phenyl and naphthyl groups containing one or more nitro, halogen, carbonyl or sulfonyl substituents, with nitro-substituted phenyl being a preferred carbocyclic aromatic electron-affinic moiety. Representative heterocyclic aromatic electron-affinic moieties include imidazoles, triazoles, pyridines, benzamides, nicotinamides, benzotriazine oxides, furans, thiophenes, oxazoles and thiozoles possessing one or more carbonyl, trifluoromethyl, halogen, nitro, sulfonyl, sulfinyl, phosphoryl, oxide or cyano groups, and preferably at least one nitro group.

Metal complex electron-affinic moieties preferably comprise $Pt^{2+}$, $Co^{3+}$, $Fe^{2+}$, $Fe^{3+}$, $Pd^{2+}$, $Cu^{2+}$, $Ti^{4+}$, or $Zr^{4+}$ as the metal and generally fall into two subgroups: (a) metal complexes of the carbocyclic and heterocyclic aromatic electron-affinic moieties discussed above, and (b) metal complexes of bidentate ligands comprising nitrogen, carbon or sulfur. In general, metal complexes of bidentate ligands correspond to the formula $—BM^LX_K$ wherein B is a bidentate ligand containing nitrogen, carbon or sulfur, $M^L$ is a metal, X is an anionic ligand such as $Cl^-$ or $^-$OAc, and k is 1-4.

Organometallic electron-affinic moieties are aliphatic or aromatic mercury radicals. The preparation and use of radiosensitizing agents incorporating mercury containing entities is described in Shenoy et al., Cancer Investigation, 10(6):533-551 (1992) and Bruce et al., Radiation Res., 24:473-481 (1965).

Electron-affinic moieties that are particularly suitable for inclusion in the compound of Formula (I) include O-quinone, semiquinone, fluorene, imidazole, triazole, pyridine, benzamide, nicotinamide, benzotriazine oxide, furan, thiophene, oxazole, and thiazole, where each of the aforementioned groups may be substituted or unsubstituted. In a preferred embodiment, $R^1$ is selected from this group.

In a particularly preferred embodiment, the method of sensitizing tumor cells to radiation is using a camptothecin-based compound selected from the group consisting of:

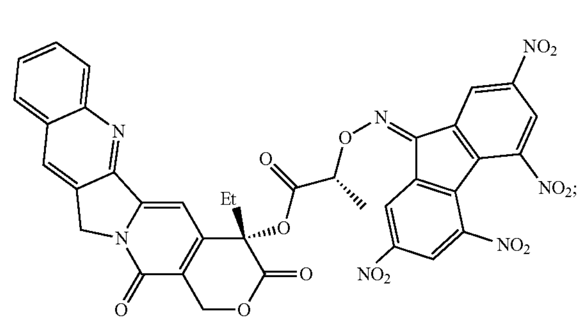

-continued
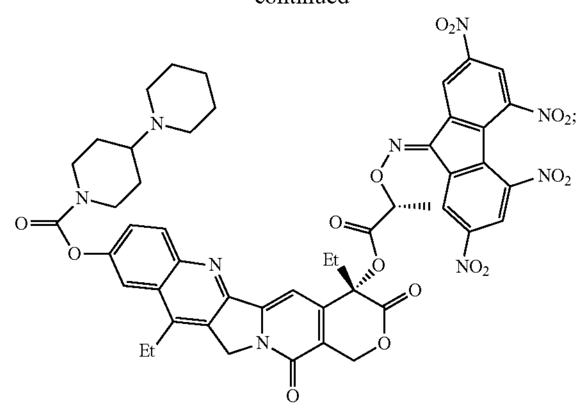
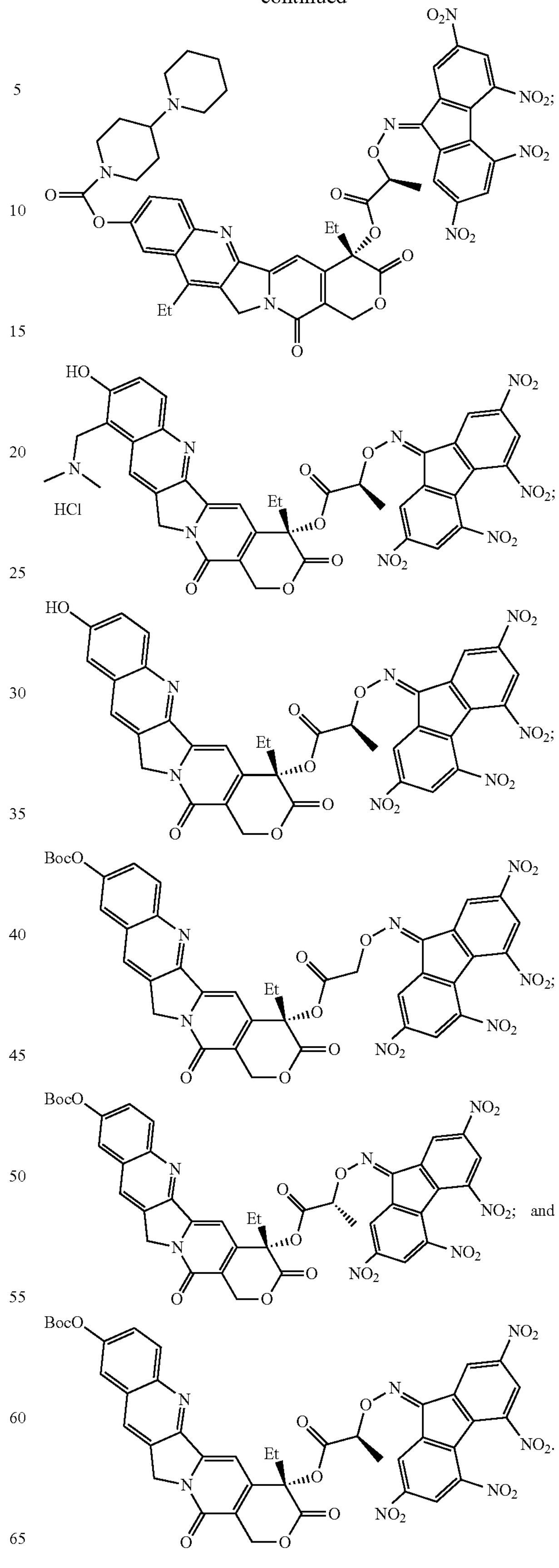

In other embodiments, the electron-affinic moiety includes an $R^1$ that is a 2-nitroimidazol-1-yl or 3-nitro-1,2,4-triazol-1-yl group having the following structure

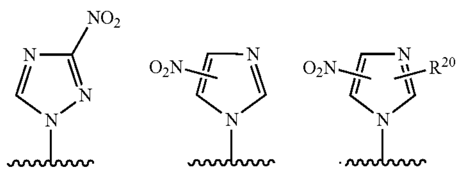

wherein $R^{20}$ is halo, alkyl, or substituted alkyl.

The electron-affinic moieties may be directly attached to one of the carbons at the C5, C7, C9, C10, C11, C12 or C20 position of camptothecin or indirectly attached via a linker. While the linker, L, may be any alkylene group of 1 to 8 carbons, optionally interrupted by one or more oxygen, sulfur or nitrogen atoms, a preferred linker is $(CH_2)_m$ or $-(T)_n$-X—, wherein X is O, S, —NR—, or a bond; T is independently CRR'; m is an integer from 0 to 3; n is an integer from 1 to 3, and each of R and $R^1$ is independently selected from hydrogen, lower alkyl, and substituted lower alkyl.

In a particularly preferred embodiment, WO—, comprised in the substitution at the −20 position of the camptothecin derivative, is selected from the group consisting of

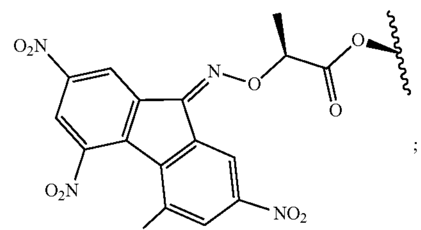

;

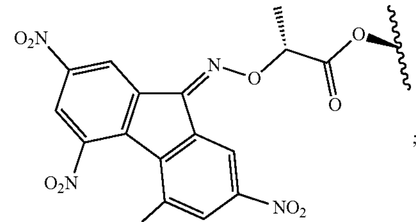

;

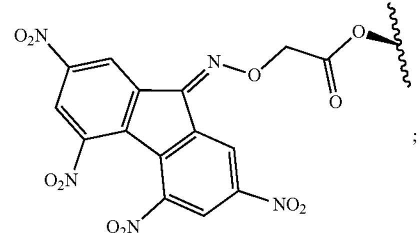

;

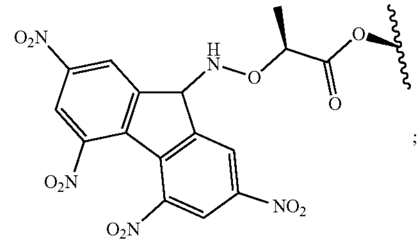

;

-continued

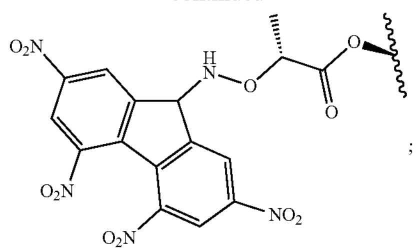

;

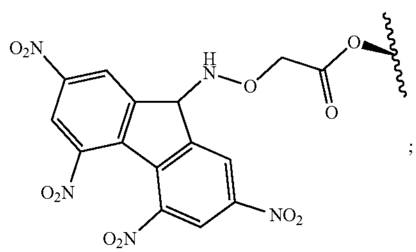

;

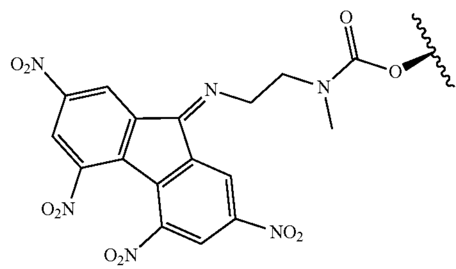

;

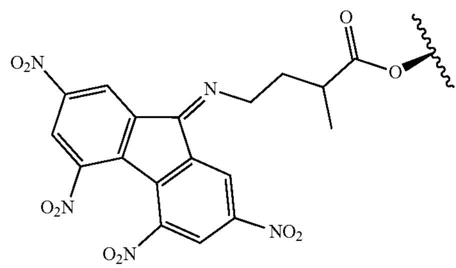

;

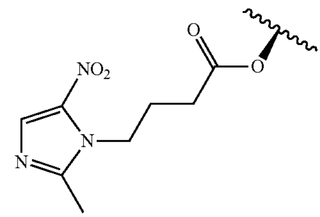

;

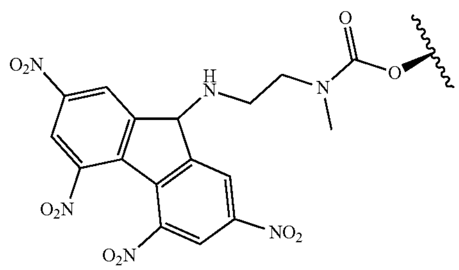

; and

-continued

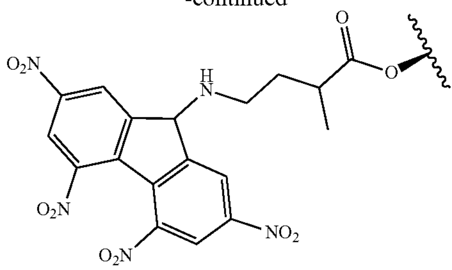

Present invention is further directed to a process for radiosensitizing tumor cells. The process comprises administering a radiosensitizing amount of the pharmaceutical composition described above to the tumor cells. Related thereto, a method is also provided for killing tumor cells in a warm-blooded animal which includes the steps of administering to the warm-blooded animal a pharmaceutical composition as described above in an amount effective to radiosensitize the tumor cells, followed by, after a time interval sufficient to enhance radiosensitization of the tumor cells, irradiating the tumor cells with a dose of radiation effective to kill the tumor cells.

As used herein, a "therapeutically effective amount" of CPT derivatives of the present invention is intended to mean that amount of the compound for inhibiting or retarding the growth of a malignant cell, or in the case of a subject having a malignant tumor, the rate of tumor growth is decreased, the volume of such tumor is reduced, or the tumor is eliminated entirely.

One aspect of this invention is a method for treating a mammal suffering from a neoplasm by administering a camptothecin-based compound to the mammal and directing ionizing radiation to the neoplasm. The compounds useful in this aspect of the invention are set forth in U.S. Pat. Nos. 6,350,756 and 6,403,603, including any reissues thereof, both of which are incorporated herein by reference in their entirety. The preferences expressed in the specification and claims of those patents are the preferences of this aspect of the invention.

In general, the compounds of U.S. Pat. No. 6,350,756 are set forth as follows:

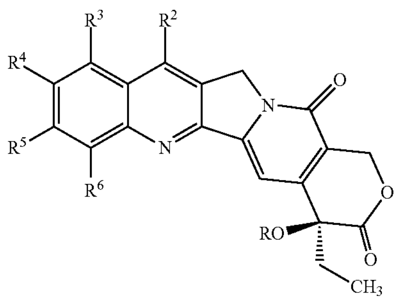

wherein R is $R^1$—O—$(CH_2)_m$—, m is an integer of 1-10 and $R^1$ is phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperazino, lower alkoxycarbonyl, and lower alkylcarbonylamino;

a fused, 2-, 3-, or 4-ring heterocyclic system optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

1- or 2-naphthyl optionally substituted with from one to four substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

a 5 or 6 membered heterocyclic ring containing one or two nitrogen atoms, which ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

$R^2$ is hydrogen, halo, lower alkyl, lower alkoxy, hydroxy, RC(O)O (R is defined hereinbefore), cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkylcarbonylamino, lower alkylcarbonyloxy methyl, substituted vinyl, 1-hydroxy-2-nitroethyl, alkoxycarbonylethyl, aminocarbonyl, alkylcarbonyl, alkylcarbonyloxymethyl, benzoylmethyl, benzylcarbonyloxymethyl, or lower alkoxymethyl;

$R^3$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, $CH_2NR^7R^8$ (where each of $R^7$ and $R^8$ is independently H—, alkyl of 1-6 carbons, optionally substituted phenyl, hydroxy lower alkyl, amino lower alkyl, or mono- or dialkylamino lower alkyl, or $R^7$ and $R^8$ taken together with —N— represent a cyclic amino-), $CH_2R^9$ (where $R^8$ is lower alkoxy, CN, amino lower alkoxy, mono- or di-lower alkylamino lower alkoxy, lower alkylthio, amino lower alkylthio, or mono- or di-lower alkylamino lower alkylthio), or $NR^{10}R^{11}$ (where each of $R^{10}$ and is independently hydrogen, lower alkyl, phenyl, hydroxy lower alkyl, or amino lower alkyl, or $R^{10}$ and $R^{11}$ taken together with —N— represent a cyclic amino), dialkylamino alkyl, lower alkylcarbonyloxy lower alkylcarbonylamino; and $R^4$ is hydrogen, halo, lower alkyl, lower alkoxy, hydroxy, RC(O)O (R is defined hereinbefore) cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, or lower alkylcarbonylamino, or $R^4$ together with $R^5$ is methylenedioxy;

$R^5$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, lower alkylcarbonyloxy, or lower alkylcarbonylamino; and $R^6$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, lower alkylcarbonyloxy, or lower alkylcarbonylamino.

The compounds of U.S. Pat. No. 6,403,604 are set forth as follows:

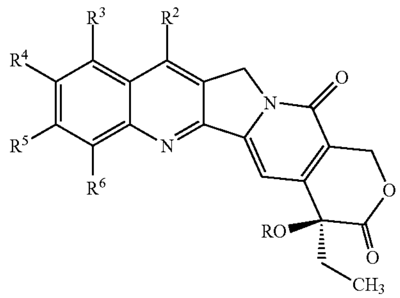

wherein R is $R^aR^bN—(CH_2)_m$, m is 2, $R^aR^b$ together with N form (a) a 5-, 6-, or 7-membered cyclic amine having no more than one additional nitrogen, oxygen, or sulfur atom in the ring, which ring is fused to another, carbocyclic ring or rings which resulting fused ring system is optionally substituted with up to two substituents chosen from lower alkyl, lower cycloalkyl, hydroxy lower alkyl, phenyl, substituted phenyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), benzyl, substituted benzyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), aminocarbonylmethyl, lower alkylaminocarbonylmethyl, amino, mono- or di-lower alkyl amino, cyclic amino, or a 5- or 6-membered heterocyclic ring optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino or (b) a 5- or 6-membered cyclic imide ring; $R^2$ is hydrogen, halo, lower alkyl, lower alkoxy, hydroxy, RC(O)O (R is defined hereinbefore), cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, alkylcarbonyl, alkylcarbonyloxymethyl, benzoylmethyl, benzyl carbonyloxymethyl, or lower alkoxymethyl, $R^3$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, $CH_2NR^7R^8$ (where each of $R^7$ and $R^8$ is independently H—, alkyl of 1-6 carbons, optionally substituted phenyl, hydroxy lower alkyl, amino lower alkyl, or mono- or dialkylamino lower alkyl, or $R^7$ and $R^8$ taken together with —N— represent a saturated 5-, 6-, or 7 membered cyclic amine ring having no more than one additional nitrogen, oxygen or sulfur atom that is optionally fused to another carbocyclic ring or rings), $CH_2R^9$ (where $R^9$ is lower alkoxy, CN, amino lower alkoxy, mono- or di-lower alkylamino lower alkoxy, lower alkylthio, amino lower alkylthio, or mono- or di-lower alkylamino lower alkylthio), or $NR^{10}R^{11}$ (where each of $R^{10}$ and $R^{11}$ is independently hydrogen, lower alkyl, phenyl, hydroxy lower alkyl, or amino lower alkyl, or $R^{10}$ and $R^{11}$ taken together with —N— represent a saturated 5-, 6, or 7 membered cyclic amine ring having no more than one additional nitrogen, oxygen or sulfur atom that is optionally fused to another carbocyclic ring or rings), dialkylamino alkyl, lower alkylcarbonyloxy, or lower alkylcarbonylamino; and $R^4$ is hydrogen, halo, lower alkyl, lower alkoxy, hydroxy, RC(O)O (R is defined hereinbefore) cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, or lower alkylcarbonylamino, or $R^4$ together with $R^5$ is methylenedioxy;

$R^5$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, lower alkylcarbonyloxy, or lower alkylcarbonylamino; and $R^6$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, lower alkylcarbonyloxy, or lower alkylcarbonylamino.

Another aspect of the invention is a method of enhancing the chemoradiosensitization efficacy of a camptothecin-based compound by chemically positioning an electron-affinic moiety at the C5, C7, C9, C10, C11, C12 or C20 position of the camptothecin molecule. The chemoradiosensitization characteristic is the capability of a compound, when administered to a subject having a neoplasm, to be absorbed by the subject and directed to the neoplasm to make the neoplasm more susceptible to radiation therapy than it would be without the administration of the compound to the subject. These enhanced compounds then are useful for treating a subject suffering from a neoplasm by administering such a compound to the subject and directing radiation to the subject's neoplasm. Preferably, the electron-affinic group is a nitro-substituted carbocyclic or heterocyclic aromatic group.

4. Compounds of the Invention

Novel compounds that are particularly valuable in all aspects of the invention are those represented by formula (II) as follows:

(II)

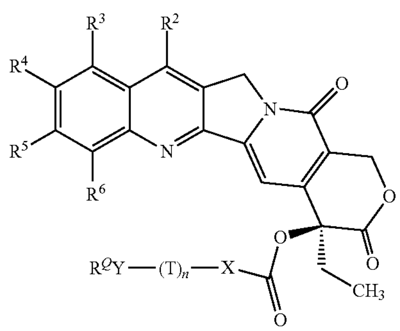

wherein

X is a O, S, —NR—, or a bond;

Y is =NO—, —N(H)O—, =N—, —NR—, O, S, or a covalent bond;

T is independently CRR';

each of R and $R^1$ is independently selected from hydrogen, $alkyl_{1-4}$, and substituted $alkyl_{1-4}$;

n is an integer from 0 to 8;

$R^1$ is optionally substituted heterocyclic, aryl, or heteroaryl;

provided that when X is a bond or $CH_2$ and n is 1, 2, or 3, then Y, when bound to $R^1$, is not oxygen; and provided that when X is a bond or $CH_2$, n is 1, 2, or 3; and $R^1$ is heterocyclic containing at least one nitrogen atom, then Y is not bound directly to said nitrogen atom;

$R^2$ is hydrogen, halo, lower alkyl, lower alkoxy, hydroxy, $R^{\mathcal{Q}}$Y-L-C(O)O—, cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkoxycarbonyloxy, sugar, phosphosugar, O-quinone, substituted lower alkyl aminomethyl, lower alkylcarbonylamino, lower alkylcarbonyloxy methyl, optionally substituted lower alkylcarbonyloxy methyl, substituted vinyl, 1-hydroxy-2-nitroethyl, alkoxycarbonylethyl, aminocarbonyl, alkylcarbonyl, alkylcarbonyloxymethyl, benzoylmethyl, benzylcarbonyloxymethyl, lower alkyliminomethyl or lower alkoxymethyl;

$R^3$ is hydrogen, halo, lower alkyl, lower alkoxy, hydroxy, $R^{\mathcal{Q}}$Y-L-C(O)O—, cyano, nitro, amino, halogenated lower alkyl, halogenated lower alkoxy, hydroxycarbonyl, formyl, lower alkoxycarbonyl, $CH_2NR^7$, $R^8$ (where each of $R^7$ and $R^8$ is independently H, alkyl of 1-6 carbons, optionally substituted phenyl, hydroxy lower alkyl, amino lower alkyl, or mono- or dialkylamino lower alkyl, or $R^7$ and $R^8$ taken together with —N— represent a cyclic amino-), $CH_2R^9$ (where $R^9$ is lower alkoxy, CN, amino lower alkoxy, mono- or di-lower alkylamino lower alkoxy, lower alkylthio, amino lower alkylthio, or mono- or di-lower alkylamino lower alkylthio), $NR^{10}R^{11}$ (where each of $R^{10}$ and $R^{11}$ is independently hydrogen, lower alkyl, phenyl, hydroxy lower alkyl, or amino lower alkyl, or $R^{10}$ and $R^{11}$ taken together with —N— represent a cyclic amino), trialkylsilyl, dialkylamino alkyl, lower alkylcarbonyloxy, lower alkoxycarbonyloxy, sugar, phosphosugar, O-quinone, substituted lower alkyl aminomethyl, or lower alkylcarbonylamino or $R^3$ together with $R^4$ is furan, dihydrofuran or 1,4-oxazine-2-one;

$R^4$ is hydrogen, halo, lower alkyl, lower alkoxy, hydroxy, $R^{\mathcal{Q}}$Y-L-C(O)O—, cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, lower alkoxycarbonyloxy, sugar, phosphosugar, O-quinone, substituted lower alkyl aminomethyl, or lower alkylcarbonylamino, or $R^4$ together with $R^3$ is furan, dihydrofuran or 1,4-oxazine-2-one, or $R^4$ together with $R^5$ is methylenedioxy;

$R^5$ is hydrogen, halo, lower alkyl, lower alkoxy, hydroxy, $R^{\mathcal{Q}}$Y-L-C(O)O—, cyano, nitro, amino, halogenated lower alkyl, halogenated lower alkoxy, hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino;

$R^6$ is hydrogen, halo, lower alkyl, lower alkoxy, hydroxy, $R^{\mathcal{Q}}$Y-L-C(O)O—, cyano, nitro, amino, trialkylsilyl, halogenated lower alkyl, halogenated lower alkoxy, hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino;

L is a linker containing a linker chain having 1 to 10 atoms independently selected from the group consisting of N, C, or O; and $R^{\mathcal{Q}}$ is an optionally substituted heterocyclic, aryl, or heteroaryl group, or $R^1$Y together form a $NR^aR^b$ group, where $R^a$, $R^b$, and the nitrogen to which they are attached form a cyclic amine or imide ring.

In one embodiment, one of the $R^2$, $R^4$, or $R^5$ is selected from the group consisting of (tris(hydroxymethyl)methylamino)methyl, (bis(hydroxymethyl)methylamino)methyl, and (2-hydroxyethylamino)methyl. In a preferred embodiment, $R^2$ is selected from the group consisting of (tris(hydroxymethyl)methylamino)methyl, (bis(hydroxymethyl)methylamino)methyl, and (2-hydroxyethylamino)methyl.

In another embodiment, $R^2$ is selected from the group consisting of (tris(hydroxymethyl)methylamino)methyl, (bis(hydroxymethyl)methylamino)methyl, and (2-hydroxyethylamino)methyl; $R^3$ is hydrogen, dimethylamino, amino, or nitro; $R^4$ is hydrogen, hydroxy, or 4-(1-piperidino)-1-piperidinocarbonyloxy; or $R^4$ together with $R^5$ is methylenedioxy; $R^5$ is hydrogen; or $R^5$ together with $R^4$ is methylenedioxy; and $R^6$ is hydrogen.

In another embodiment, $R^2$ is selected from the group consisting of (tris(hydroxymethyl)methylamino)methyl, (bis(hydroxymethyl)methylamino)methyl, and (2-hydroxyethylamino)methyl; $R^3$ is hydrogen; $R^4$ together with $R^5$ is methylenedioxy and $R^6$ is hydrogen.

In yet another embodiment, $R^2$ is selected from the group consisting of (tris(hydroxymethyl)methylamino)methyl, (bis(hydroxymethyl)methylamino)methyl, and (2-hydroxyethylamino)methyl and each of $R^3$, $R^4$, $R^5$, and $R^6$ is hydrogen.

In a preferred embodiment $R^1$ is aromatic. In a preferred embodiment X is a covalent bond. Additionally it is preferred that Y is =NO— or —N(H)O— and even more preferably that n is 1 and each of R and $R^1$ is independently methyl or hydrogen. In a further preferred embodiment, $R^1$ is a substituted or unsubstituted carbocyclic, preferably having 1 to 4 aromatic rings. The substituted or unsubstituted carbocyclic may be 9-fluorenyl, preferably substituted with at least one nitro group. In one embodiment of the compound, $R^1$ is

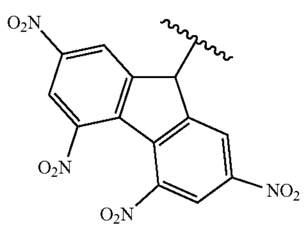 [SMILES: *C1c2cc([N+](=O)[O-])cc([N+](=O)[O-])c2-c2c1cc([N+](=O)[O-])cc2[N+](=O)[O-]]
In a preferred embodiment, the camptothecin-based compound is selected from the group consisting of
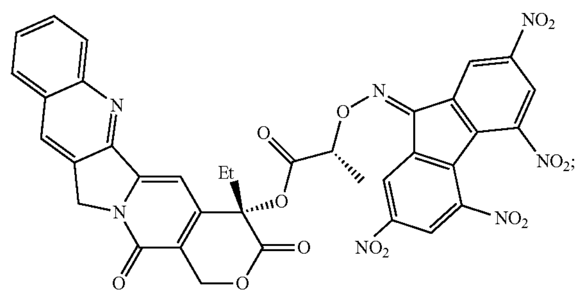
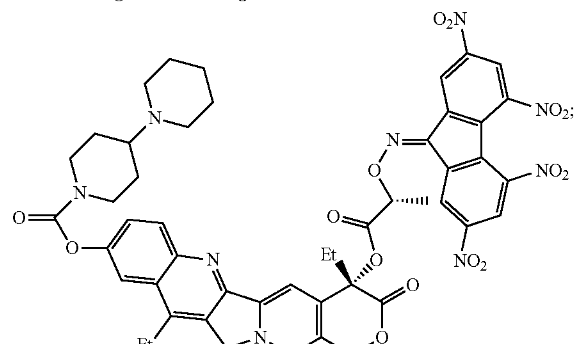
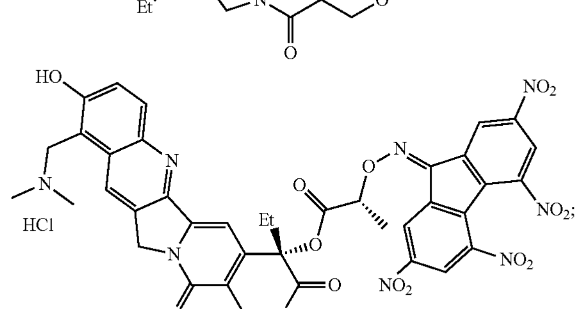
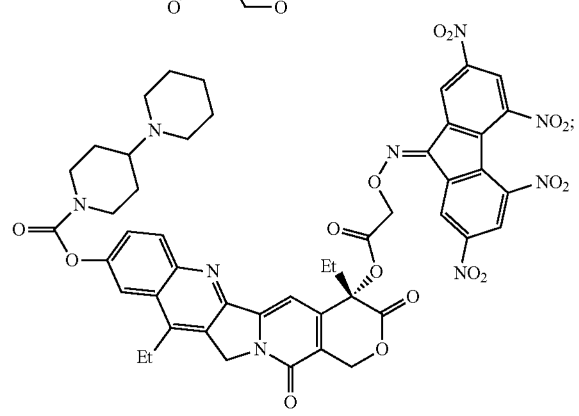
-continued
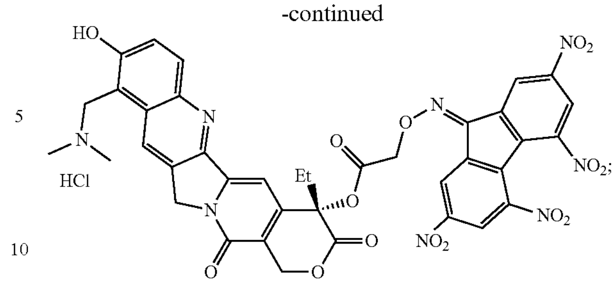

-continued
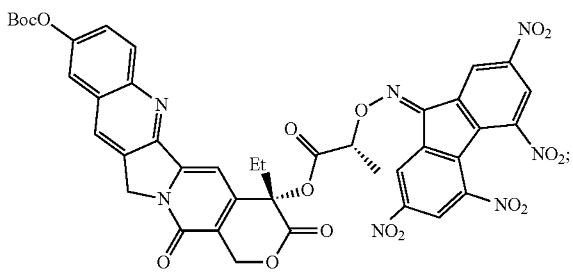
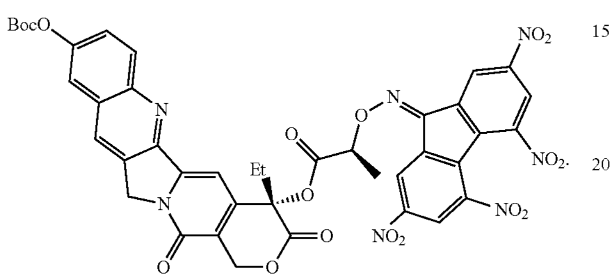
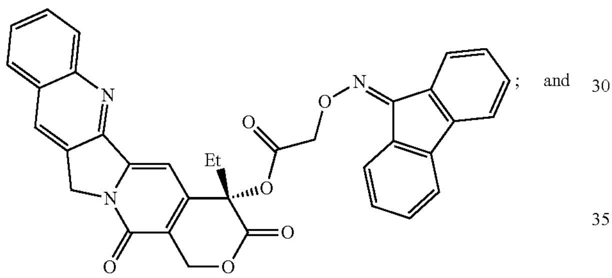
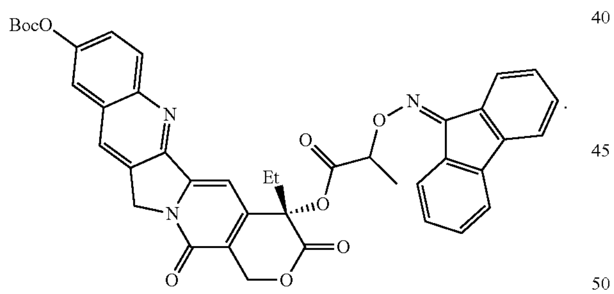
In another preferred embodiment, the compound of Formula (II) includes an $R^1$ or $R^Q$ that is
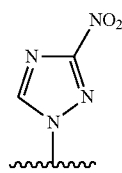
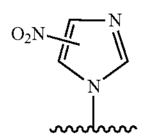
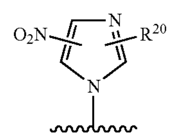
wherein $R^{20}$ is halo, alkyl, or substituted alkyl.
In yet another preferred embodiment of Formula (II), $R^1Y$-$(T)_n$-X—C(O)O— is
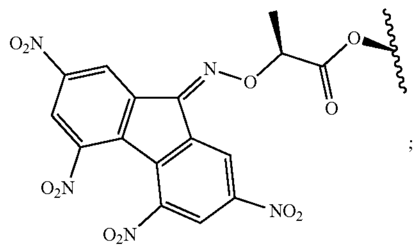
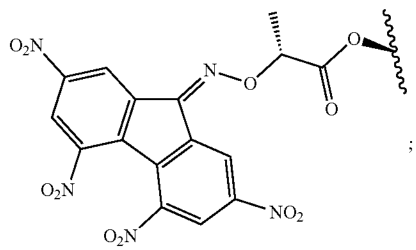
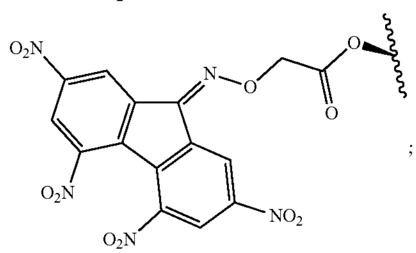
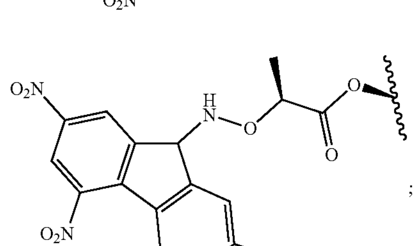
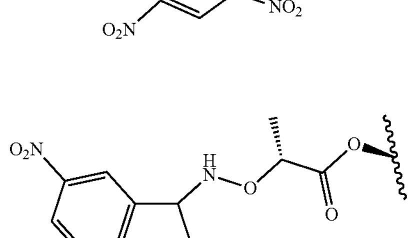
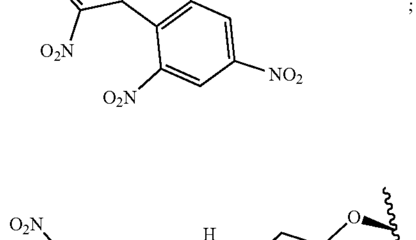
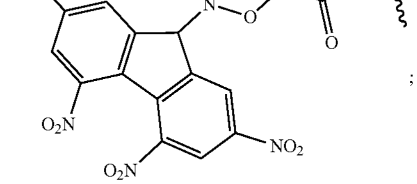

-continued

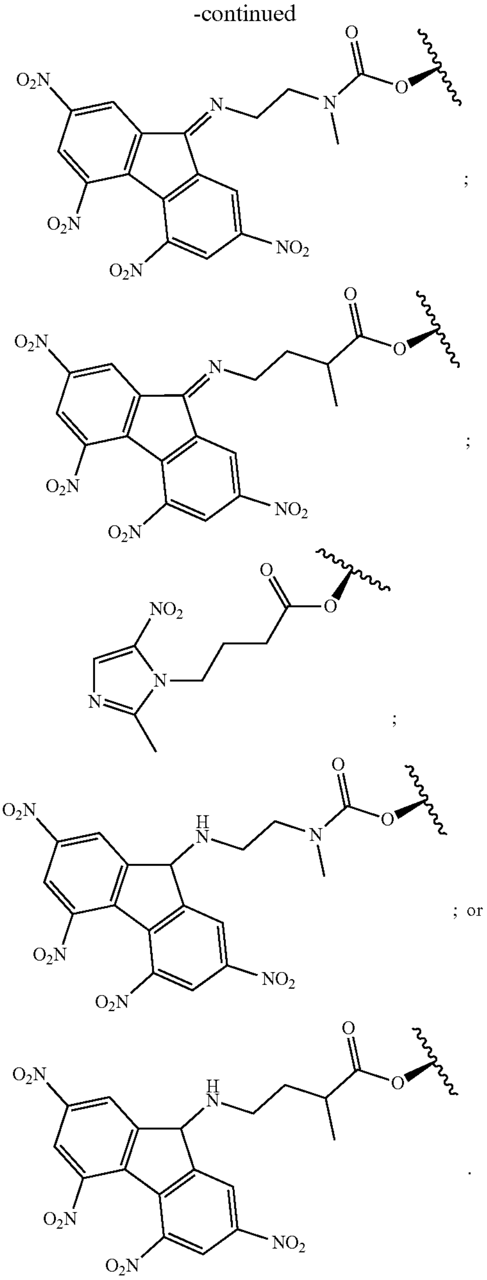

Certain camptothecin derivatives are particularly desirable, for example, a compound of the formula (II), wherein $R^2$ is hydrogen;

$R^3$ is $CH_2NR^7$, $R^8$ (where each of $R^7$ and $R^8$ is independently H, alkyl of 1-6 carbons, optionally substituted phenyl, hydroxy lower alkyl, amino lower alkyl, or mono- or dialkylamino lower alkyl, or $R^7$ and $R^8$ taken together with —N— represent a cyclic amino-), $NR^{10}R^{11}$ (where each of $R^{10}$ and $R^{11}$ is independently hydrogen, lower alkyl, phenyl, hydroxy lower alkyl, or amino lower alkyl, or $R^{10}$ and $R^{11}$ taken together with —N— represent a cyclic amino), or dialkylamino alkyl;

$R^4$ is lower alkoxy, hydroxy, halogenated lower alkyl, halogenated lower alkoxy, hydroxycarbonyl, formyl, lower alkoxycarbonyl, carbamoyloxy, lower alkylcarbonyloxy, lower alkoxycarbonyloxy, sugar, phosphosugar, or $R^4$ together with $R^5$ is methylenedioxy;

$R^5$ is hydrogen or together with $R^4$ is methylenedioxy; and $R^6$ is hydrogen.

More preferably, $R^3$ is $CH_2NR^7$, $R^8$ (where each of $R^7$ and $R^8$ is lower alkyl), $R^4$ is hydroxy, alkoxy, or alkylcarbonyloxy, and $R^5$ is hydrogen. In a particularly preferred embodiment of this compound, $R^3$ is $CH_2N(CH_3)_2$ and/or $R^4$ is hydroxy.

Similarly, a preferred compound of Formula (II) has the following features:

$R^2$ is hydrogen, lower alkyl or halogenated lower alkyl;

$R^3$ is hydrogen or lower alkyl;

$R^4$ is lower alkoxy, hydroxy, halogenated lower alkoxy, hydroxycarbonyl, carbamoyloxy, lower alkylcarbonyloxy, lower alkoxycarbonyloxy, sugar, phosphosugar, or $R^4$ together with $R^5$ is methylenedioxy;

$R^5$ is hydrogen or together with $R^4$ is methylenedioxy; and $R^6$ is hydrogen.

Preferably, $R^3$ is hydrogen, $R^4$ is carbamoyloxy, and $R^5$ is hydrogen. Even more preferably, $R^2$ is lower alkyl, especially ethyl, and $R^4$ is 4-(1-piperidino)-1-piperidinocarbonyloxy.

In other embodiments of invention, $R^2$ is hydrogen and $R^4$ is 4-(1-piperidino)-1-piperidinocarbonyloxy.

In other embodiments of invention, $R^2$ is hydrogen, $R^3$ is hydrogen and $R^4$ is tert-butoxycarbonyloxy.

Yet another preferred compound of the invention is of Formula (II), wherein $R^2$ is lower alkyl;

$R^3$ is hydrogen;

$R^4$ is hydroxy, lower alkoxy, halogenated lower alkoxy, hydroxycarbonyl, formyl, lower alkoxycarbonyl, lower alkoxycarbonyloxy, sugar, phosphosugar, or lower alkylcarbonyloxy;

$R^5$ is hydrogen; and $R^6$ is hydrogen.

Preferably, $R^2$ is ethyl and $R^4$ is hydroxy.

Yet another preferred compound of the invention is of Formula (II) where $R^2$, $R^4$, $R^5$ and $R^6$ are hydrogen and $R^3$ is amino or nitro. An alternative compound of Formula (II) has the following substituents:

$R^2$ is tri-lower alkylsilyl;

$R^3$ is hydrogen;

$R^4$ is hydroxy, lower alkoxy, halogenated lower alkoxy, hydroxycarbonyl, formyl, lower alkoxycarbonyl, lower alkoxycarbonyloxy, sugar, phosphosugar, carbamoyloxy or lower alkylcarbonyloxy;

$R^5$ is hydrogen; and $R^6$ is hydrogen.

Preferably, $R^2$ is t-butyldimethylsilyl and $R^4$ is hydroxy.

While the linker, L, may be any alkylene group of 1 to 8 carbons, optionally interrupted by one or more oxygen, sulfur or nitrogen atoms, a preferred linker is $(CH_2)_m$ or $-(T)_n$-X—, wherein X is O, S, —NR—, or a bond; T is independently CRR'; m is an integer from 0 to 3; n is an integer from 1 to 3, and each of R and R' is independently selected from hydrogen, alkyl, and substituted alkyl.

In some embodiments, this invention also provides a composition comprising a compound of this invention together with a pharmaceutically acceptable excipient.

In some embodiments, this invention also provides a method for treating a cancer disorder in a subject having a tumor which method comprises administering to the subject a composition a composition comprising a compound of this invention together with a pharmaceutically acceptable excipient. The method further comprises exposing the tumor in the subject to a unit dose of radiation.

In some embodiments, this invention also provides a method of treating a neoplasm comprising:

a) administering to the subject a compound or a pharmaceutically acceptable salt thereof having formula (I) and b) exposing said subject to a unit dose of radiation.

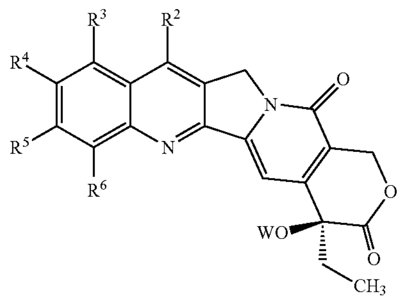

wherein W is alkylC(O)—, or $R^1$Y-L-C(O)—, provided that when W is alkylC(O)—, at least one of $R^2$, $R^3$, $R^4$, $R^5$, or $R^6$ is nitro;

L is a bond or linear alkylene (1-8) group, optionally substituted with lower alkyl or substituted lower alkyl, wherein one or two methylene (—$CH_2$—) units of the linear alkylene group is optionally replaced with O, S or NH;

Y is ═NO—, —N(H)O—, ═N—, —NR—, O, S, or a bond;

R is H, alkyl, or substituted alkyl;

$R^1$ is optionally substituted carbocyclic, heterocyclic, or fused 2-, 3- or 4-ring heterocyclic;

$R^2$ is hydrogen, halo, lower alkyl, lower alkoxy, hydroxy, $R^{Q}$Y, $R^{Q}$Y-L-C(O)O—, cyano, nitro, amino, halogenated lower alkyl, halogenated lower alkoxy, hydroxycarbonyl, formyl, lower alkoxycarbonyl, lower alkoxycarbonyloxy, sugar, phosphosugar, O-quinone, substituted lower alkyl aminomethyl, tri lower alkylsilyl, lower alkylcarbonyloxy, lower alkylcarbonylamino, lower alkylcarbonyloxy methyl, substituted vinyl, 1-hydroxy-2-nitroethyl, alkoxycarbonylethyl, aminocarbonyl, alkylcarbonyl, alkylcarbonyloxymethyl, benzoylmethyl, benzylcarbonyloxymethyl, or lower alkoxymethyl;

$R^3$ is hydrogen, halo, lower alkyl, lower alkoxy, hydroxy, $R^{Q}$Y-L-C(O)O—, cyano, nitro, amino, halogenated lower alkyl, halogenated lower alkoxy, hydroxycarbonyl, formyl, lower alkoxycarbonyl, lower alkoxycarbonyloxy, sugar, phosphosugar, O-quinone, substituted lower alkyl aminomethyl, $CH_2NR^7$, $R^8$ (where each of $R^7$ and $R^8$ is independently H, alkyl of 1-6 carbons, optionally substituted phenyl, hydroxy lower alkyl, amino lower alkyl, or mono- or dialkylamino lower alkyl, or $R^7$ and $R^8$ taken together with —N— represent a cyclic amino-), $CH_2R^9$ (where $R^9$ is lower alkoxy, CN, amino lower alkoxy, mono- or di-lower alkylamino lower alkoxy, lower alkylthio, amino lower alkylthio, or mono- or di-lower alkylamino lower alkylthio), $NR^{10}R^{11}$ (where each of $R^{10}$ and $R^{11}$ is independently hydrogen, lower alkyl, phenyl, hydroxy lower alkyl, or amino lower alkyl, or $R^{10}$ and $R^{11}$ taken together with —N— represent a cyclic amino), dialkylamino alkyl, lower alkylcarbonyloxy, or lower alkylcarbonylamino; and $R^4$ is hydrogen, halo, lower alkyl, lower alkoxy, hydroxy, $R^{Q}$Y-L-C(O)O—, cyano, nitro, amino, amino lower alkyl, halogenated lower alkyl, halogenated lower alkoxy, hydroxycarbonyl, formyl, lower alkoxycarbonyl, lower alkoxycarbonyloxy, sugar, phosphosugar, O-quinone, substituted lower alkyl aminomethyl, carbamoyloxy, lower alkylcarbonyloxy, or lower alkylcarbonylamino, or $R^4$ together with $R^5$ is methylenedioxy;

$R^5$ is hydrogen, halo, lower alkyl, lower alkoxy, hydroxy, $R^{Q}$Y-L-C(O)O—, cyano, nitro, amino, halogenated lower alkyl, halogenated lower alkoxy, hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino;

$R^6$ is hydrogen, halo, lower alkyl, lower alkoxy, hydroxy, $R^{Q}$Y-L-C(O)O—, cyano, nitro, amino, halogenated lower alkyl, halogenated lower alkoxy, hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino; and $R^{Q}$ is optionally substituted carbocyclic, heterocyclic, or fused 2-, 3- or 4-ring heterocyclic; and 5. Synthesis of Compounds of the Invention The compounds of the invention are prepared by reacting a known camptothecin-based compound having a free hydroxyl or an amine group with an appropriate electron-affinic moiety. Many camptothecin-based compounds are generally available in the art and would be known to one of ordinary skill in the art.

As Camptothecin (CPT) exhibits antineoplastic activity, several synthetic and semisynthetic analogs of CPT have been reported in the literature. A number of attempts have been made not only to reduce its toxicity while maintaining antitumor activity by converting CPT into its derivatives but also to make it more water soluble by chemical modifications. Scientists continue to develop analogs in order to improve the pharmacokinetics, drug resistance, clinical efficacy, and toxicity profile of CPT. Based on the knowledge about total synthesis and semi-synthesis of CPT analogs, there are numerous possible ways of attaching electron-affinic groups at various positions on the CPT molecule. The radiosensitizing compounds of this invention can be prepared by linking the electron-affinic group to any of the C5, C7, C9, C10, C11, C12 or C20 carbons of CPT using a variety of methods. The following Schemes 1 to 7 demonstrate a few representative examples of the same.

C20 Analogs

Compounds having electron-affinic groups at C20 may be prepared by reacting CPT or a CPT analog with a carboxylic acid of the formula $R^1Y\text{-}(T)_n\text{-}X$—COOH wherein $R^1$, Y, $(T)_n$, and X are as defined herein.

For example, an electron-affinic group, such as tetranitrofluorene, can be attached to the 20 position via an ester linkage by treating a CPT analog with 1,3-dicyclohexylcarbodiimide (DCC) and (+)-2-(2,4,5,7-tetranitro-9-fluorenylideneaminooxy)-propionic acid (TAPA) (commercially available from Wiley) in dry methylene chloride at room temperature to provide the ester 1.1 as shown below (Scheme 1). Optionally the imine double bond in ester 1.1 can be reacted with a reducing agent such as sodium borohydride ($NaBH_4$) to give the amine 1.2.

Scheme 1

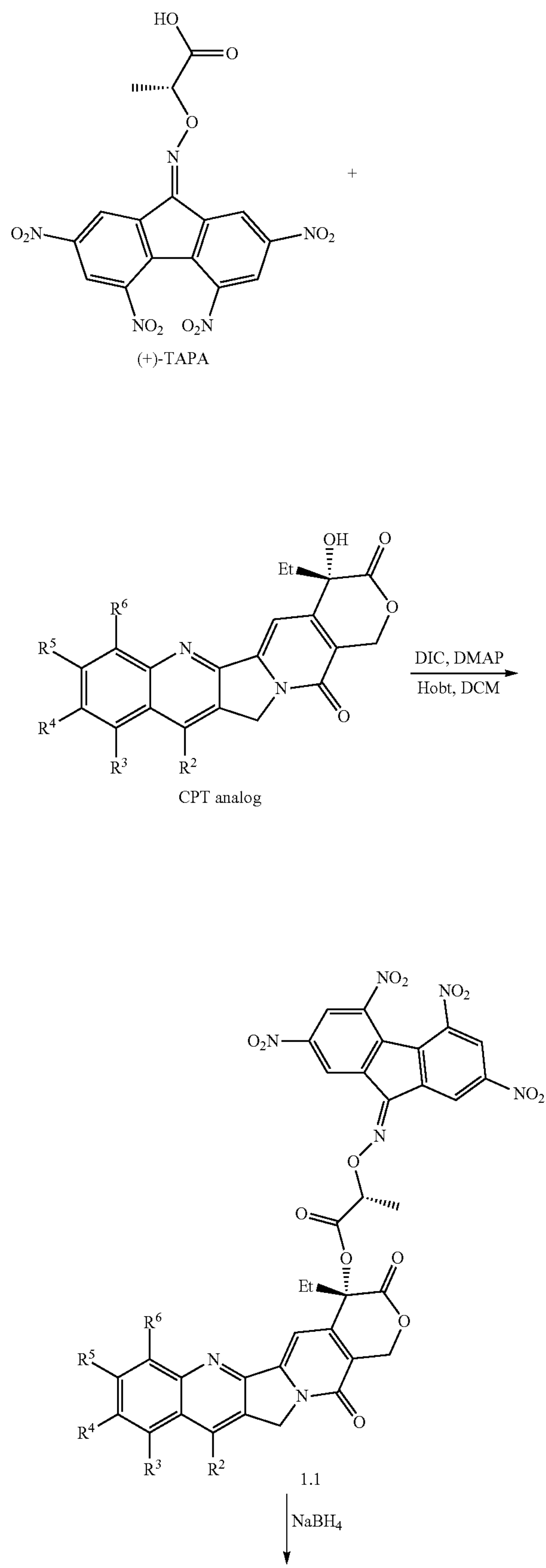

-continued

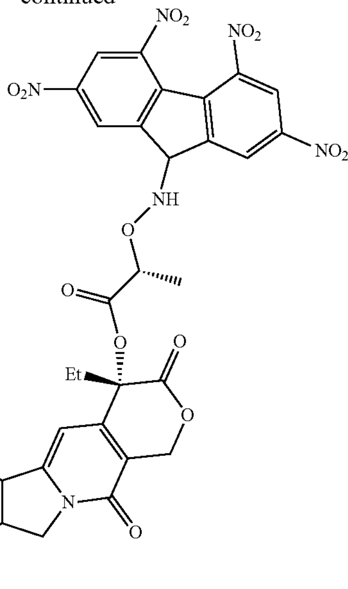

1.2

The above reaction can be carried out with a suitable CPT analog that is substituted at any of the 5, 7, 9, 10, 11 or 12 positions. The CPT analog may be substituted with substituents known in the art or that can be prepared by one of skill in the art. Representative articles that teach how to make such analogs or where such analogs may be procured are found in the following journals.

1. J. Med. Chem. 1998, 41, 31-37
2. J. Med. Chem. 2000, 43, 3970-3980
3. J. Med. Chem. 1993, 36, 2689-2700
4. J. Med. Chem. 1991, 34, 98-107
5. J. Med. Chem. 2000, 43, 3963-3969
6. Chem. Pharm. Bull. 1991, 39(10), 2574-2580
7. Chem. Pharm. Bull. 1991, 39(6), 1446-1454
8. Antimicrobial Agents and Chemotherapy, December 1999, 2862-2868
9. European Journal of Cancer 1998, 34(10), 1500-1503
10. Cancer Research, Feb. 15, 1995, 55, 753-760
11. Anti-Cancer Drug Design 1998, 13, 145-157
12. Bioorg. Med. Chem. Lett. 1998, 8, 415-418
13. Bioorg. Med. Chem. Lett. 2003, 11, 451.
14. Biochem. Pharmacol. 2005, 70(8), 1125-1136
15. Cancer Chemother. Pharmacol., Aug. 20, 2005, 1-10
16. Bioorg. Med. Chem., Feb. 6, 2003, 11(3), 451-458.
17. Cancer Chemother. Pharmacol., 2001, 48(1), 83-87
18. Bioorg. Med. Chem. Lett. 2003, 13, 3739-3741
19. Jpn. J. Cancer Res. 1995, 86, 776-782
20. J. Chromatogr. B Analyt. Technol. Biomed. Life Sci. 2003, 784, 25-31
21. Biomed Chromatogr. 2003, 17(6), 385-90
22. Yao. Xue. Xue. Bao. 2005, 40(3), 241-247
23. Bioorg. Med. Chem. Lett. 2005, 15(13), 3233-3236
24. Bioorg. Med. Chem. 2004, 12(15), 4003-4008
25. Expert Opin. Investig. Drugs 2004, 13(3), 269-284
26. J. Med. Chem., Feb. 26, 2004, 47(5), 1280-1289
27. Blood 2005, 105(9), 3714-3721
28. J. Enzy. Inhib. Med. Chem. 2003, 18(2), 101-109
29. Bioorg. Med. Chem. Lett. 2005, 15, 2003-2006
30. Anticancer Drugs 2004, 15, 545-552
31. Bioorg. Med. Chem. 2003, 11, 1851-1857

32. Peptides 2005, 26, 1560-1566

33. Bioorg. Med. Chem. Lett. 2004, 14, 4023-4026

34. Bioorg. Med. Chem. 2004, 12, 3657-3662

35. Cancer Research 2004, 64, 6679-6683

Suitable CPT analogs include the following, where the number in parenthesis following the name refers to the journal article listed above:

(20S)-7-ethyl-10-[4-(1-piperidino)-1-piperidino]carbonyloxy)-CPT (AKA-irinotecan);
(20S)-9-nitro CPT (1);
(20S)-7-chloro-n-propyldimethylsilyl CPT (2);
(20S)-10-hydroxy-7-chloro-n-propyldimethylsilyl CPT (2);
(20S)-10-acetoxy-7-chloro-n-propyldimethylsilyl CPT (2);
(20S)-7-tert-butyldimethylsilyl CPT (2);
(20S)-10-hydroxy-7-tert-butyldimethylsilyl CPT (2);
(20S)-10-acetoxy-7-tert-butyldimethylsilyl CPT (2);
(20S)-9-hydroxy CPT (3);
(20S)-9-amino CPT (3);
(20S)-10-amino CPT (3);
(20S)-9-amino-10-hydroxy CPT (3);
(20S)-9-methylamino CPT;
(20S)-9-chloro CPT (3);
(20S)-9-fluoro CPT (3);
(20S)-9-piperidino CPT;
(20S)-9-dimethylaminomethyl-10-hydroxy CPT (3)-AKA topotecan);
(20S)-9-morpholinomethyl CPT (4);
(20S)-10-hydroxy CPT (3);
(20S)-9,10-dichloro CPT (3);
(20S)-10-bromo CPT (3);
(20S)-10-chloro CPT (3);
(20S)-10-methyl CPT (3);
(20S)-10-fluoro CPT (3);
(20S)-10-nitro CPT (3);
(20S)-10,11-methylenedioxy CPT (3);
(20S)-10-formyl CPT (3);
(20S)-10-nonylcarbonyloxy CPT (12);
(20S)-10-undecylcarbonyloxy CPT (12);
(20S)-10-heptadecylcarbonyloxy CPT (12);
(20S)-10-nonadecylcarbonyloxy CPT (12);
(20S)-9-nitro-10,11-methylenedioxy CPT (3);
(20S)-9-(4-methylpiperazinylmethyl)-10-hydroxy (CPT) (4);
(20S)-9-[4-(1-piperidino)-1-piperidinomethyl]-10-hydroxy CPT (4);
(20S)-9-methyl-10,11-methylenedioxy CPT;
(20S)-9-chloro-10,11-methylenedioxy CPT (3);
(20S)-9-cyano-10,11-methylenedioxy CPT;
(20S)-9-acetoxy-10,11-methylenedioxy CPT;
(20S)-9-acetylamino-10,11-methylenedioxy CPT;
(20S)-9-aminomethyl-10-hydroxy CPT;
(20S)-9-ethoxymethyl-10-hydroxy CPT (4);
(20S)-9-methylaminomethyl-10-hydroxy CPT;
(20S)-9-n-propylaminomethyl-10-hydroxy CPT (4);
(20S)-9-dimethylaminomethyl-10-hydroxy CPT (4);
(20S)-9-cyclohexylaminomethyl-10-hydroxy CPT (4);
(20S)-9-(2-hydroxyethyl)aminomethyl-10-hydroxy CPT (4);
(20S)-9-(trimethylammonio)methyl-10-hydroxy CPT, methanesulfonate (4);
(20S)-9-morpholinomethyl-10-hydroxy CPT (4);
(20S)-5-(2-hydroxyethoxy) CPT (20S)-9-cyanomethyl-10-hydroxy CPT (4);
(20S)-CPT-7-aldehyde (5);
(20S)-10-methoxy CPT-7-aldehyde (5);
(20S)-7-acetoxymethyl CPT (5);
(20S)-7-acetoxymethyl-10-methyl CPT (5);
(20S)-7-cyano-10-methoxy CPT (5);
(20S)-7-cyano CPT (5);
(20S)-7-formylethenyl CPT (5);
(20S)-7-ethoxycarbonylethenyl CPT (5);
(20S)-7-cyanoethenyl CPT (5);
(20S)-7-(2,2-dicyanoethenyl) CPT (5);
(20S)-7-(2-cyano-2-ethoxycarbonyl)ethenyl CPT (5);
(20S)-7-ethoxycarbonyl ethyl CPT (5);
(20S)-7-ethyl CPT (6);
(20S)-7-n-propyl CPT (6);
(20S)-7-acetoxymethyl CPT (6);
(20S)-7-n-propylcarbonyloxymethyl CPT (6);
(20S)-7-ethoxycarbonyl CPT (6);
(20S)-7-ethyl-10-hydroxy CPT;
(20S)-7-ethyl-10-acetyloxy CPT;
(20S)-7-methyl-10-aminocarbonyloxy CPT;
(20S)-7-n-propyl-10-piperidinocazbonyloxy CPT;
(20S)-7-ethyl-10-(2-dimethylamino)ethyl CPT; and
(20S)-7-ethyl-10-carbamoyloxy derivatives of CPT such as
(20S)-7-ethyl-10-[4(1-piperidino)-piperidino]carbonyloxy CPT (7);
(20S)-7-ethyl-10-(1-piperazine)carbonyloxy CPT (7);
(20S)-7-ethyl-10-(4-i-propylaminocarbonylmethylpiperazine)carbonyloxy CPT (7);
(20S)-7-ethyl-10-[4(1-pyrrolidinyl)piperazine]carbonyloxy CPT (7);
(20S)-7-ethyl-10-[(4-(dimethylamino)-1-piperidino]carbonyloxy CPT (7);
(20S)-7-ethyl-10-[4-(di-n-propylamino)-1-piperidinol]carbonyloxy CPT (7);
(20S)-7-ethyl-10-[(4-(di-n-butylamino)-1-piperidino]carbonyloxy CPT (7);
(20S)-7-ethyl-10-[4-(1-pyrrolidino)-1-piperidino)]carbonyloxy CPT (7);
(20S)-7-ethyl-10-[4-(1-piperidino)-1-piperidino]carbonyloxy CPT (7);
(20S)-7-ethyl-10-[N-methyl-N-2-(dimethylamino)ethylamino]carbonyloxy CPT (7)
(20S)-7-(tert-butyldimethylsilyl)CPT (13)
(20S)-7-(tert-butoxyiminomethyl) CPT (Gimatecan) (14)
(20S)-7-butyl-10,11-methylenedioxy CPT (15)
(20S)-7-bromomethyl-10-hydroxy CPT (15)
(20S)-7-butyl-10-amino CPT (15)
(20S)-7-(tert-butyldimethylsilyl)-10-hydroxy CPT (16)
(20S)-7-[(2-trimethylsilyl)ethyl)] CPT (Karentican) (17)
(20S)-7-[(4-fluorophenoxy)acetyloxymethyl] CPT (18)
(20S)-7-[(4-methoxyphenoxy)acetyloxymethyl] CPT (18)
(20S)-7-[(4-cyano-3-fluorophenoxy)acetyloxymethyl] CPT (18)
(20S)-7-[(3,4,5-trimethoxyphenyl)acetyloxymethyl] CPT (18)
(20S)-10-[(4-cyano-3-fluorophenoxy)acetyloxy] CPT (18)
(20S)-10-[(3,4,5-trimethoxyphenyl)acetyloxy] CPT (18)
(20S)-7-(4-methylpiperazinomethylene)-10,11-ethylenedioxy CPT (Exatecan) (19)
(20S)-7-[2-(N-isopropylamino)ethyl] CPT (Belotecan) (20)
(20S)-[5(RS)-(2-hydroxyethoxy)] CPT (21)
(20S)-7-ethyl-9-allyl-10-hydroxy CPT (29)
(20S)-7-ethyl-9-allyl-10-methoxy CPT (29)
(20S)-7-ethyl-9-propyl-10-hydroxy CPT (29) (20S)-7-ethyl-9-propyl-10-methoxy CPT (29) (20S)-7,9-diethyl-10-hydroxy CPT (29)
(20S)-7,9-diethyl-10-methoxy CPT (29)
(20S)-10-(substituted quaternary ammonium salts) CPT (33)
(20S)-7-(tris(hydroxymethyl)methylamino)methyl CPT (35)
(20S)-7-(bis(hydroxymethyl)methylamino)methyl CPT (35)
(20S)-7-(2-hydroxyethylamino)methyl CPT (35)

(20S)-7-(tris(hydroxymethyl)methylamino)methyl-10,11-methylenedioxy CPT (35)

(20S)-7-(bis(hydroxymethyl)methylamino)methyl-10,11-methylenedioxy CPT (35)

(20S)-7-(2-hydroxyethylamino)methyl-10,11-methylenedioxy CPT (35)

(20S)-7-(tris(hydroxymethyl)methylamino)methyl-10-[4-(1-piperidino)-1-piperidino]carbonyloxy) CPT (20S)-7-(bis(hydroxymethyl)methylamino)methyl-10-[4-(1-piperidino)-1-piperidino]carbonyloxy) CPT (20S)-7-(2-hydroxyethylamino)methyl-10-[4-(1-piperidino)-1-piperidino]carbonyloxy) CPT (20S)-7-(tris(hydroxymethyl)methylamino)methyl-9-dimethylaminomethyl-10-hydroxy CPT (20S)-7-(bis(hydroxymethyl)methylamino)methyl-9-dimethylaminomethyl-10-hydroxy CPT (20S)-7-(2-hydroxyethylamino)methyl-9-dimethylaminomethyl-10-hydroxy CPT (20S)-7-(tris(hydroxymethyl)methylamino)methyl-9-amino CPT (20S)-7-(bis(hydroxymethyl)methylamino)methyl-9-amino CPT (20S)-7-(2-hydroxyethylamino)methyl-9-amino CPT (20S)-7-(tris(hydroxymethyl)methylamino)methyl-9-nitro CPT (20S)-7-(bis(hydroxymethyl)methylamino)methyl-9-nitro CPT (20S)-7-(2-hydroxyethylamino)methyl-9-nitro CPT (20S)-7-(tris(hydroxymethyl)methylamino)methyl-10-hydroxy CPT (20S)-7-(bis(hydroxymethyl)methylamino)methyl-10-hydroxy CPT (20S)-7-(2-hydroxyethylamino)methyl-10-hydroxy CPT; and the like.

It will be recognized by one of skill in the art that other similar compounds may be prepared by following the teachings set forth in the above articles and modifying with appropriate art-recognized steps.

Several other derivatives of tetranitrofluorene similarly can be attached at the 20 position of CPT or a CPT analog. These tetranitrofluorenes can be synthesized in one step via condensation of tetranitrofluoren-9-one (commercially available from Aldrich) and an amine of the formula $NH_2$—O-$(T)_n$-X—COOH, wherein $(T)_n$ and X are as defined herein. The imine 2.1 then reacts with CPT or a CPT analog to give the C20 esters 2.2, wherein $R_2$, $R_3$, $R_4$, $R_5$, and $R_6$ are as defined herein (Scheme 2). Optionally, the imine double bond in ester 2.2 can be reacted with a reducing agent such as sodium borohydride ($NaBH_4$) to give the amine 2.3.

Scheme 2

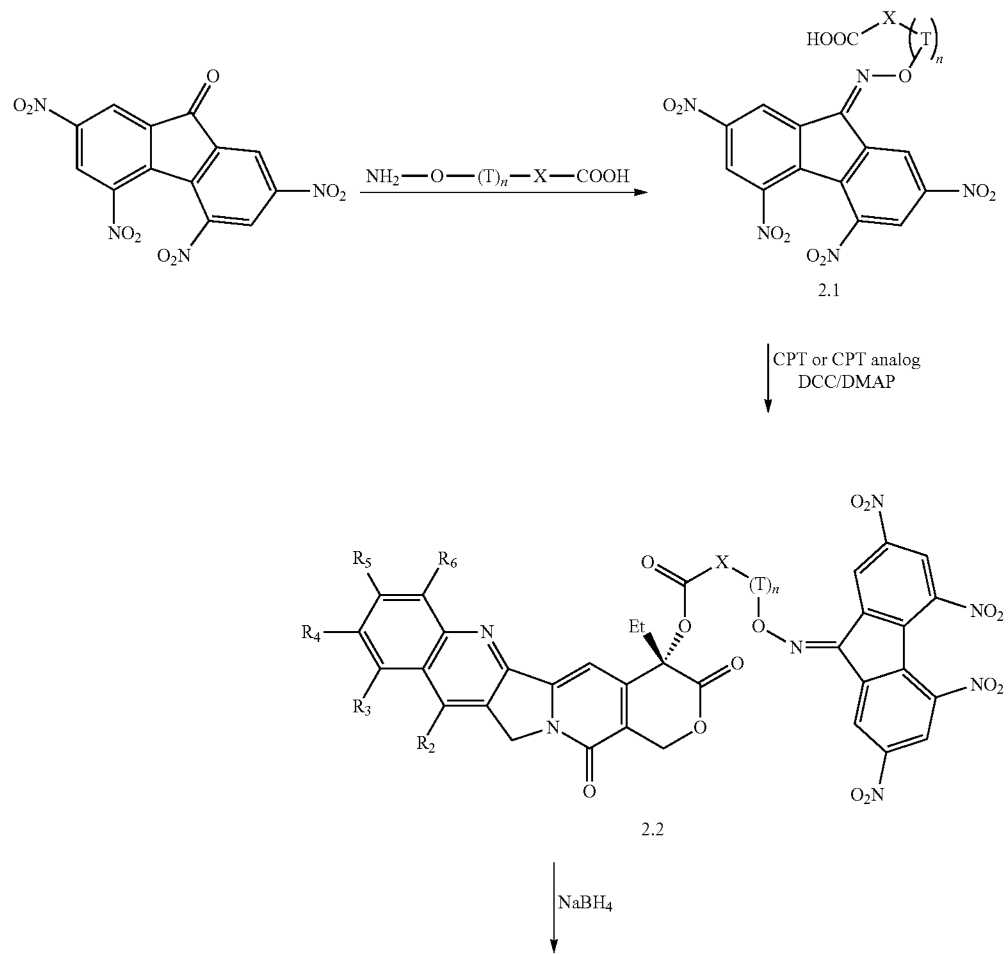

-continued

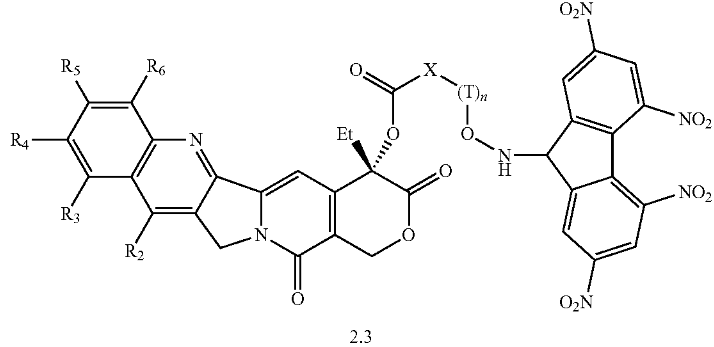

2.3

Similarly, other electron-affinic groups such as nitroimidazole, nitrotriazole, nitrothiazole, etc. can be linked at the 20 position of CPT or CPT analogs. Thus, coupling of CPT or a CPT analog with CDI (1,1'-carbonyldiimidazole) followed by reaction of the intermediate 20-carbonylimidazolide with alcohols gives analogs where the radiosensitizing group is attached via a carbonate linkage (X═O). The length and nature of the linker between CPT and the electron-affinic group may be altered. It is possible to prepare analogs in which electron-affinic group is either closer or further away from the CPT molecule. For example, reaction with 4-nitrobenzoic acid gives the corresponding 4-nitrobenzoate 3.1 where the electron-affinic group is very close to the CPT molecule. While reaction with CDI (for conditions, see US Pub. No. US 2002/0040155 A1) followed by 2-(2-nitro-imidazol-1-yl)ethanol gives the corresponding carbonate 3.2 where the electron-affinic group is away from the CPT molecule. It is also possible to prepare analogs with multiple radiosensitizing groups attached to a single linker. For example, reaction of 2-nitroimidazole with glycidyl chloride provides alcohol A (US Pub. No. US 2002/0040155 A1) which then reacts with CPT to give a carbonate 3.3 containing 2 radiosensitizing groups linked at C20 (Scheme 3).

The structure of CPT is shown in the following schemes as:

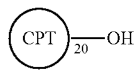

For analogs of CPT, the structure is shown as above and the additional substituent is shown with its position on the CPT molecule.

Scheme 3

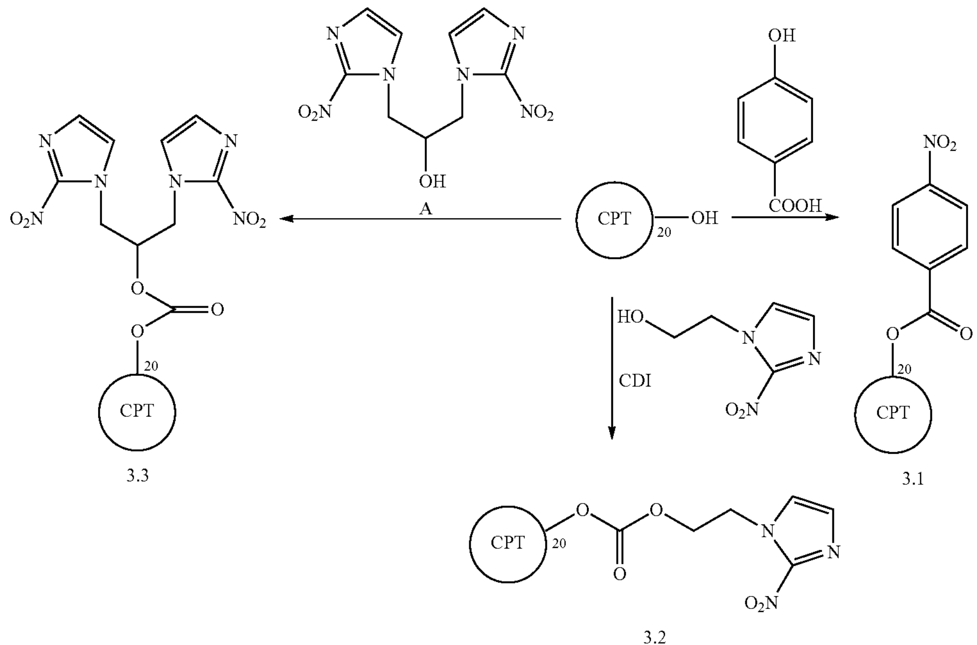

C9 and C10 Analogs

Electron-affinic groups also can be linked at 9 or 10 positions. Condensation of 9- or 10-amino CPT (J. Med. Chem. 1993, 36, 2689-2700) with nitro-substituted ketones gives the corresponding imines. For example, 2,4,5,7-tetranitrofluoren-9-one (commercially available from Aldrich) gives the corresponding imine 4.1 with radiosensitizing tetranitrofluorenyl group at 9 or 10 position (Scheme 4). Reduction of the double bond in imine 4.1 with reducing agents such as $NaBH_4$ followed by acylation of 20-hydroxy group with acyl halide gives the amine 4.2. Several other nitroaldehydes or nitroketones also react similarly.

Scheme 4

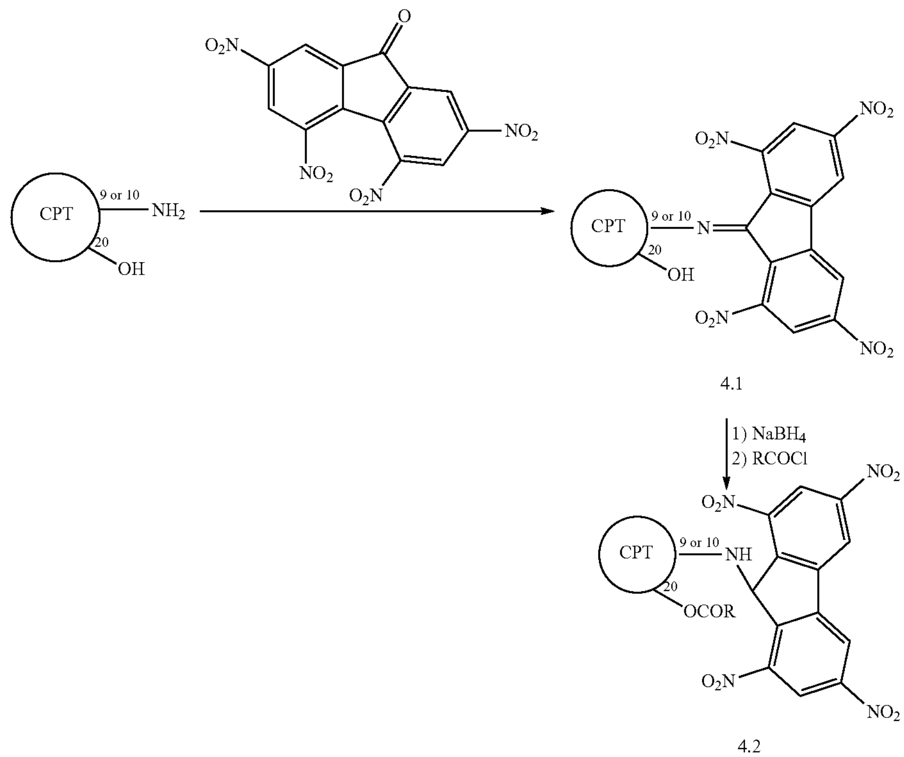

Alternatively, 9- or 10-hydroxy CPT (J. Med. Chem. 1993, 36, 2689-2700) can be converted to the corresponding phenolic esters containing electron-affinic groups. Depending on the polarity of solvent used (Bioorg. Med. Chem. Lett. 2003, 13, 3739-3741), either mono- or di-ester is formed (Scheme 5). The carboxylic acids 2.1 used in Scheme 2 react with either 9- or 10-hydroxy CPT in presence of 1-(3-dimethylaminopropyl)-3-ethyl-carbodiimide (EDCI) in a polar solvent such as dimethylformamide (DMF) to give the corresponding mono-esters 5.1. Alternatively, if the reaction is carried out in a nonpolar solvent such as methylene chloride, the corresponding di-esters 5.2 are formed. The imine bond in mono-ester 5.1 on reduction with reducing agents such as $NaBH_4$ followed by acylation of 20-hydroxy group with acyl halide gives the corresponding amine 5.3. The imine bond in di-ester 5.2 on reduction with reducing agents such as $NaBH_4$ gives the corresponding amine 5.4. Similarly, other carboxylic acids containing electron-affinic groups can be used in this reaction. Also, CPT analogs that contain 9- or 10-hydroxy group and additional substituents in the molecule can also be converted to their di-esters.

Scheme 5

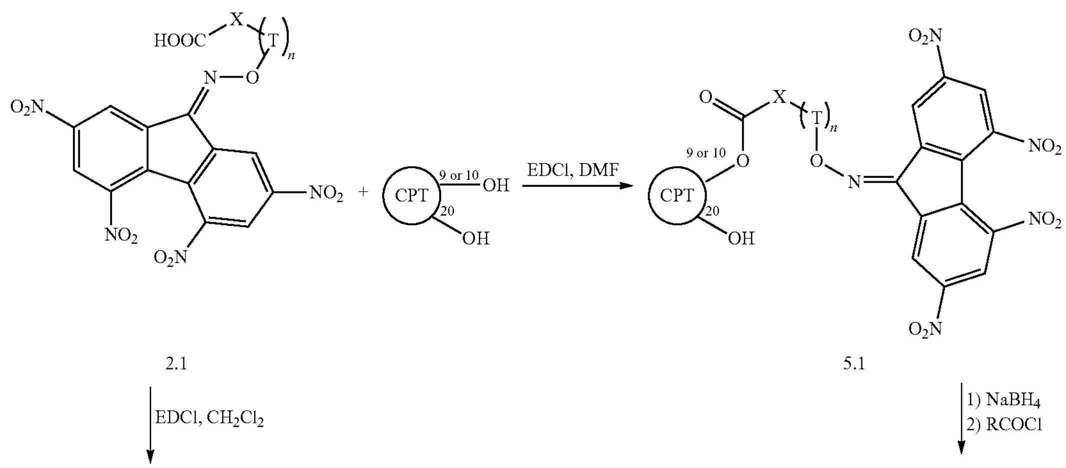

-continued

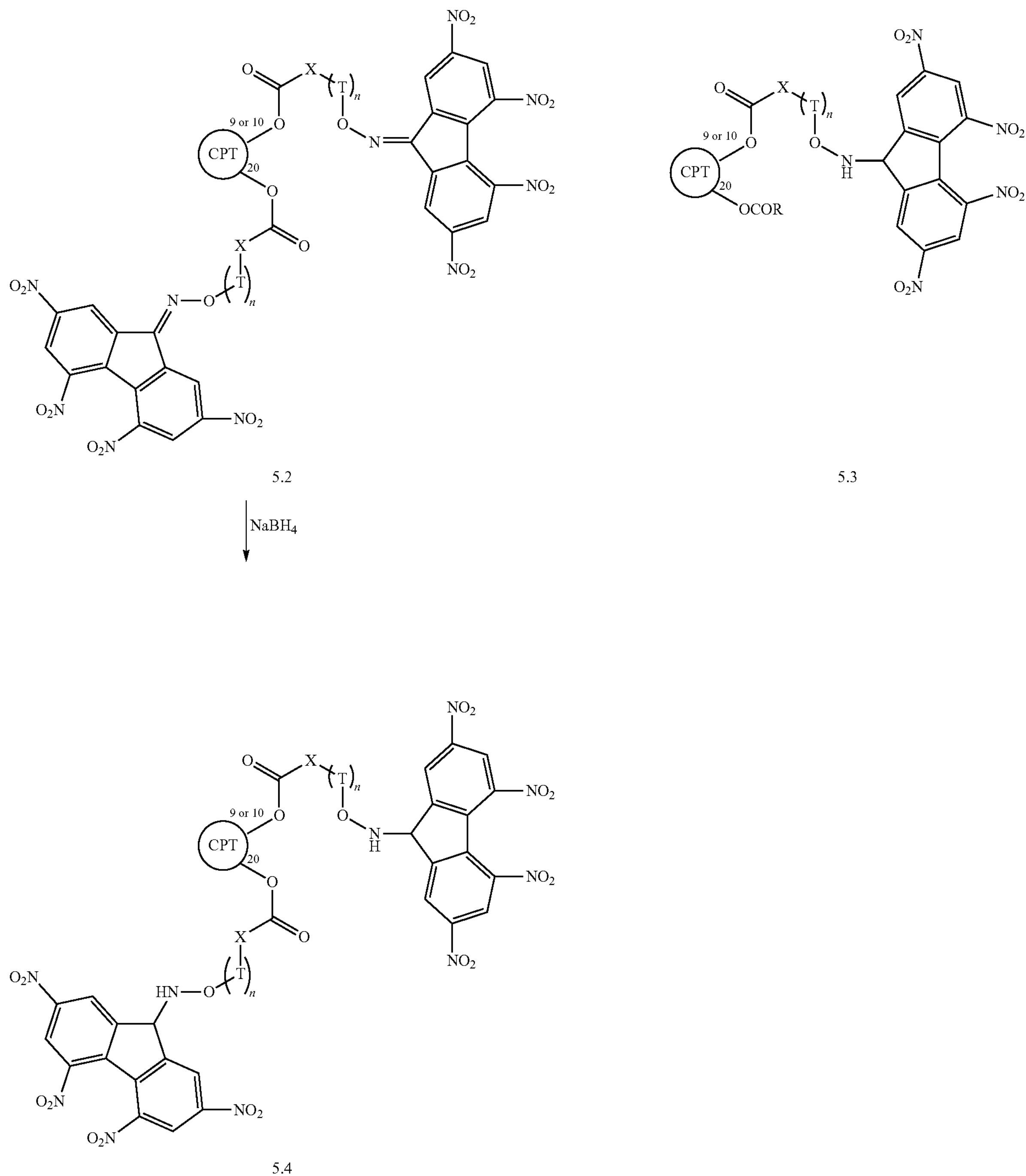

C7 Analogs

The 7-hydroxyalkyl CPT analogs, where R' is alkylene (Chem. Pharm. Bull. 1991, 39(10) 2574-2580) can be similarly acylated as shown above for the 9- or 10-hydroxy analogs, using carboxylic acids 2.1 to give the corresponding mono-esters 6.1 or di-esters 6.2 (Scheme 6). The imine bond in mono-ester 6.1 on reduction with reducing agents such as $NaBH_4$ followed by acylation of 20-hydroxy group with acyl halide gives the corresponding amine 6.3. The imine bond in di-ester 6.2 on reduction with reducing agents such as $NaBH_4$ gives the corresponding amine 6.4. Similarly, other carboxylic acids containing electron-affinic groups can be used in this reaction.

Scheme 6
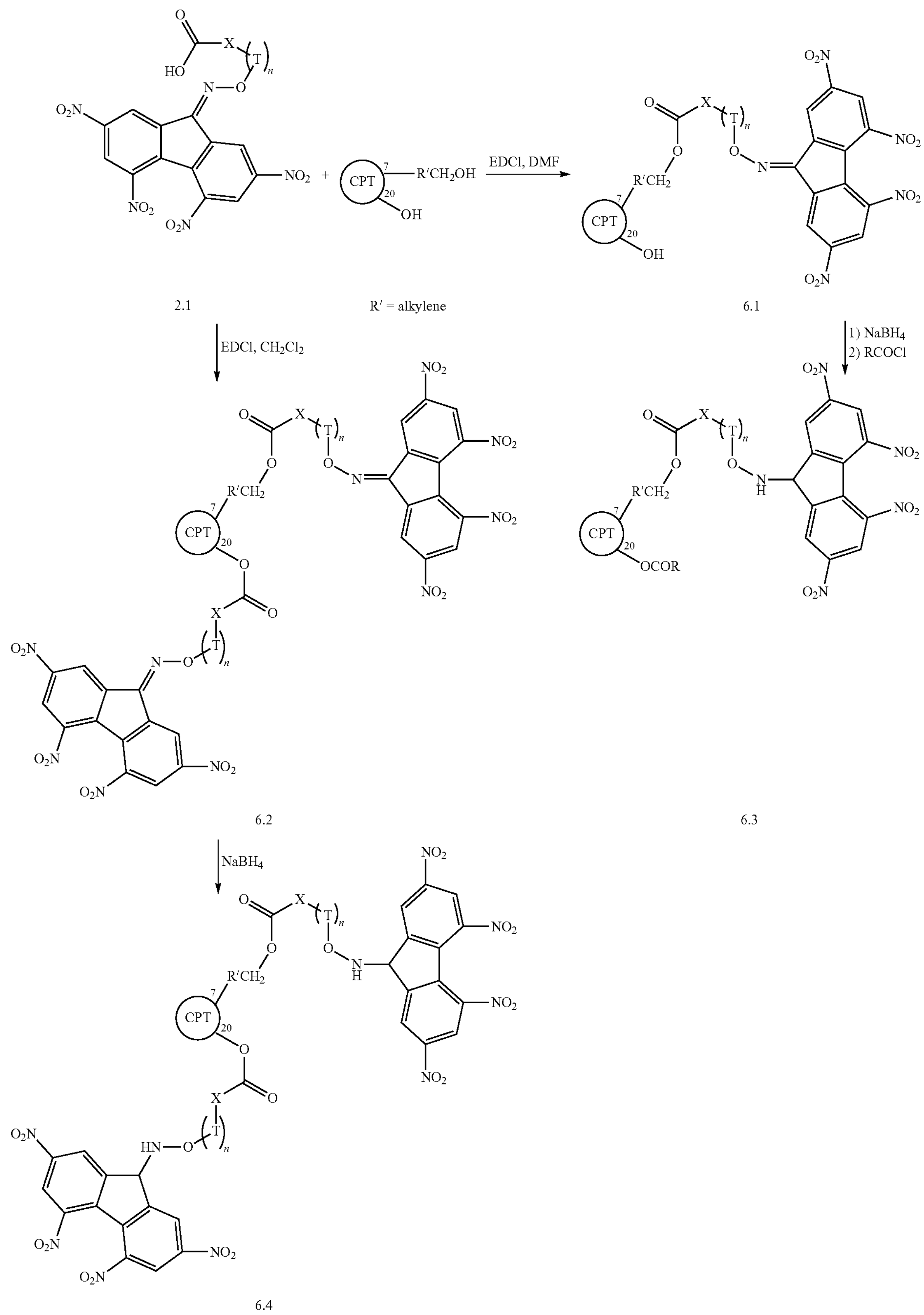

C11 and C12 Analogs 11- or 12-hydroxy CPT can be converted to the corresponding phenolic esters containing the electron-affinic groups at 11 or 12 positions. 11-hydroxy CPT is known in the literature (U.S. Pat. No. 4,604,463). Starting with 12-amino CPT (J. Med. Chem. 1986, 29, 2358 and J. Med. Chem. 1987, 30, 1774), the corresponding 12-hydroxy CPT can be synthesized using the known two-step method (U.S. Pat. No. 4,604,463). The 11- or 12-hydroxy CPT are similarly acylated as shown above for the 7, 9, or 10-hydroxy analogs, using carboxylic acids 2.1 to give the corresponding mono-esters 7.1 or di-esters 7.2 (Scheme 7). The imine bond in mono-ester 7.1 on reduction with reducing agents such as $NaBH_4$ followed by acylation of 20-hydroxy group with acyl halide gives the corresponding amine 7.3. The imine bond in di-ester 7.2 on reduction with reducing agents such as $NaBH_4$ gives the corresponding amine 7.4. Similarly, other carboxylic acids containing electron-affinic groups can be used in this reaction. Also, CPT analogs that contain 11 or 12-hydroxy group and additional substituents in the molecule can also be used in this reaction.

Scheme 7

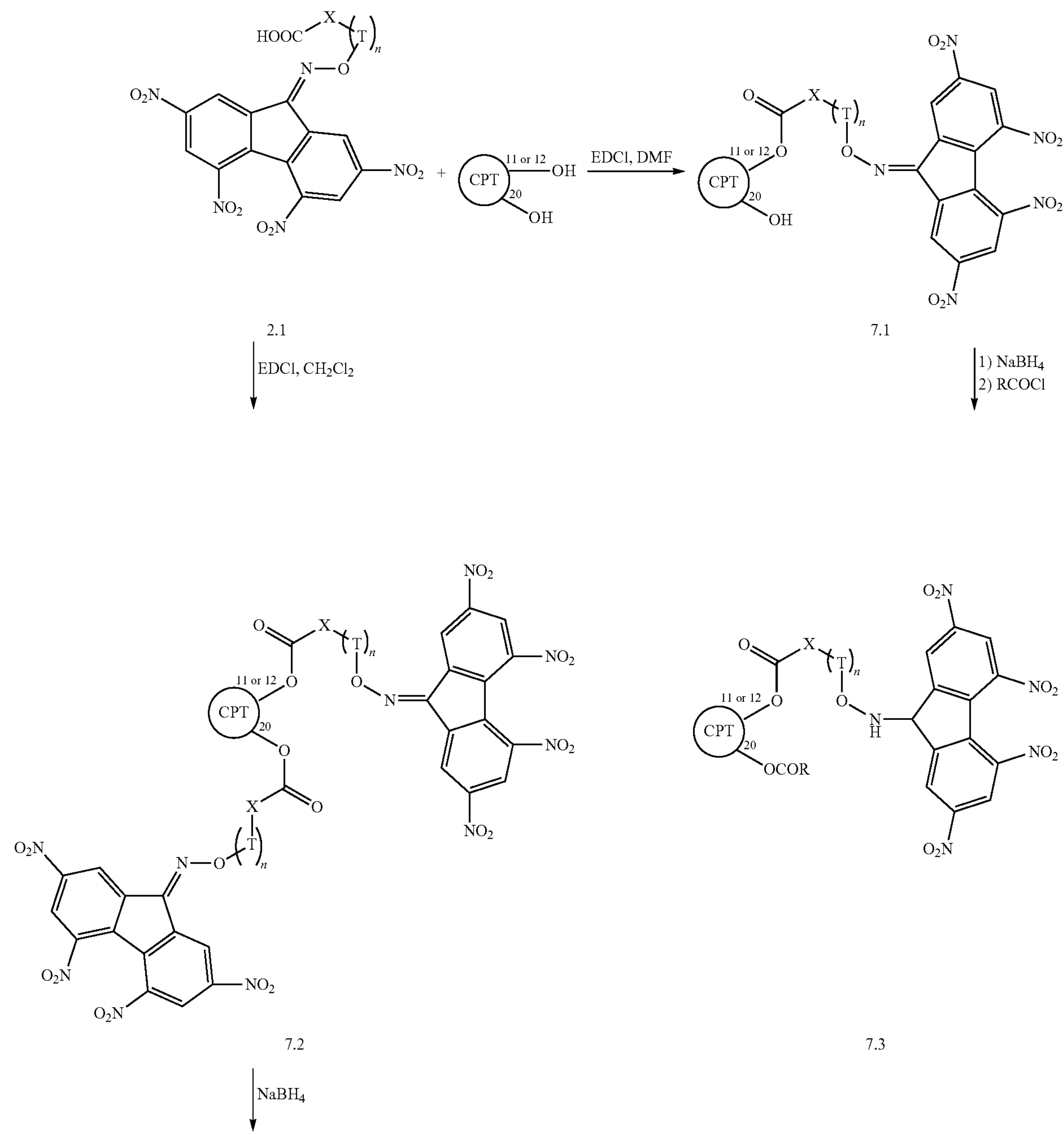

-continued

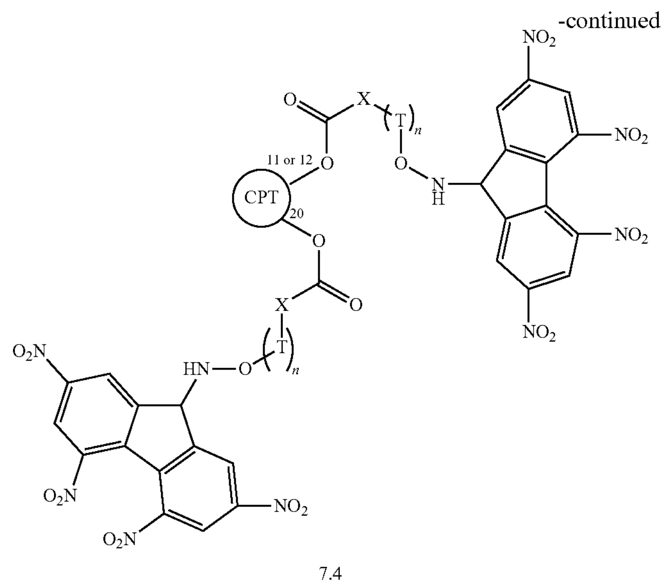

7.4

In addition, the reactions shown in Scheme 3 can also be applied for 7, 9, 10, 11, or 12-hydroxy CPT to give the corresponding CPT analogs containing various other electron-affinic groups.

C5 Analogs

The semi-synthesis of 5-substituted CPT analogs has been reported in the literature (Bioorg Med Chem. Lett. 1995, 5(1), 77-82 and Bioorg Med Chem. Lett. 1999; 9(12), 1633-1638). One 5-substituted CPT analog, 5-(2-hydroxyethoxy) CPT (The Journal of Clinical Pharmacology 2004, 44, 723-736), is already in clinical trials. Using the synthetic strategy reported in the above-mentioned references, electron affinic groups can be linked to the 5 position of a CPT molecule or analog.

Several other CPT analogs containing sugar, phosphosugar, or O-quinone moiety at C5, C7, C9, C10, C11, C12, or C20 position can also be prepared by attaching those moieties via an ether linkage. These analogs can be obtained via one step coupling reaction of the corresponding hydroxy CPT analog, with a sugar, a phosphosugar, or a quinone respectively. Representative examples of sugar and phosphosugar are given in the definition section above. Representative examples of quinone include, but are not limited to, unsubstituted and optionally substituted benzoquinones, unsubstituted and optionally substituted naphthoquinones, etc. For example, an unsubstituted benzoquinone can be attached at C9 of CPT via an ether linkage by coupling of 9-hydroxy CPT with 2-chlorobenzoquinone (commercially available at Sigma-Aldrich). Other examples of commercially available quinones at Sigma-Aldrich include, but are not limited to, 2,3-Dichloro-5,6-dicyano-1,4-benzoquinone, 2,5-Dibromo-6-isopropyl-3-methyl-1,4-benzoquinone, and 2,3-Dichloro-1,4-naphthoquinone, etc.

6. Pharmaceutical Composition of the Invention

This aspect of the invention is a pharmaceutical composition useful for treating cancer in a warm-blooded animal, which composition comprises a compound of the invention, as defined by formula II herein, in combination with a pharmaceutically acceptable excipient. The composition is prepared in accordance with known formulation techniques to provide a composition suitable for oral, topical, transdermal, rectal, inhalation, or parenteral (intravenous, intramuscular, or intraperitoneal) administration, and the like. Detailed guidance for preparing compositions of the invention are found by reference to the $18^{th}$ or $19^{th}$ Edition of Remington's Pharmaceutical Sciences, Published by the Mack Publishing Co., Easton, Pa. 18040. The pertinent portions are incorporated herein by reference.

Unit doses or multiple dose forms are contemplated, each offering advantages in certain clinical settings. The unit dose would contain a predetermined quantity of active compound calculated to produce the desired effect(s) in the setting of treating cancer. The multiple dose form may be particularly useful when multiples of single doses, or fractional doses, are required to achieve the desired ends. Either of these dosing forms may have specifications that are dictated by or directly dependent upon the unique characteristic of the particular compound, the particular therapeutic effect to be achieved, and any limitations inherent in the art of preparing the particular compound for treatment of cancer.

A unit dose will contain a therapeutically effective amount sufficient to treat cancer in a subject and may contain from about 1.0 to 1000 mg of compound, for example about 50 to 500 mg.

The compound will preferably be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will contain about 50 to about 500 mg of a compound of Formula (I).

The form may deliver a compound rapidly or may be a sustained-release preparation. The compound may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained. Preferred compositions according to the current invention are prepared so that an oral dosage unit form contains between about 5 to about 50% by weight (% w) in dosage units weighing between 50 and 1000 mg.

The suitable formulation of an oral dosage unit may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like. Various other material may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91-93 for a fuller discussion.

A compound may be administered parenterally, e.g., intravenously, intramuscularly, intravenously, subcutaneously, or interperitonically. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of the compound may be prepared in suitable diluents such as water, ethanol, glycerol, liquid polyethylene glycol(s), various oils, and/or mixtures thereof, and others known to those skilled in the art.

The pharmaceutical forms suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

In some cases, e.g., where a compound of the invention is quite water insoluble, it may be useful to provide liposomal delivery. The system restrains the compound of the invention by incorporating, encapsulating, surrounding, or entrapping the compound of the invention in, on, or by lipid vesicles or liposomes, or by micelles.

Usefully, the compound of the invention is solubilized in liposomes. The liposomes may include, for example, lipids such as cholesterol, phospholipids, or micelles comprised of surfactant such as, for example, sodium dodecylsulfate, octylphenolpolyoxyethylene glycol, or sorbitan mono-oleate. Typically, the compound of the invention binds to the lipid bilayer membrane of the liposome with high affinity. The liposome bound prodrug can preferably intercalate between the acyl chains of the lipid. The lactone ring of the camptothecin-derivative, membrane-bound compound of the invention is thereby removed from the aqueous environment inside and outside of the liposome and further protected from hydrolysis. Since the liposome-bound drug is protected from hydrolysis, the antitumor activity of the drug is preserved. For a compound of the invention which has a lower affinity for the liposome membrane and thus disassociates from the liposome membrane to reside in the interior of liposome, the pH of the interior of the liposomes may be reduced thereby preventing hydrolysis of such compound of the invention.

A useful group of liposomal delivery systems which may be used in accordance with the present invention include those described in U.S. Pat. Nos. 5,552,156 and 5,736,156, which are herein incorporated in their entireties by reference. Other liposomal delivery systems which may be employed in accordance with the present invention include liposomes containing active agents aggregated with lipids or surfactants as described in U.S. Pat. Nos. 5,827,533 and 5,882,679; lipid vesicles formed with alkyl ammonium fatty acid salts as described in U.S. Pat. No. 5,874,105; liposomes for encapsulating active agent dry powder compositions as described in U.S. Pat. No. 5,783,211; liposomal drug delivery systems for topical patches as described in U.S. Pat. No. 5,718,914; the liposomes described in U.S. Pat. No. 5,631,237; the liposome and lipid complex compositions described in U.S. Pat. Nos. 5,549,910 and 5,077,057; the liposomes used for sustained release of steroidal drugs as described in U.S. Pat. No. 5,043,165; the liposomes described in U.S. Pat. No. 5,013,556; and the liposomes described in U.S. Pat. No. 4,663,161; all of which are herein incorporated in their entireties by reference.

Unilamellar liposomes, also referred to as single lamellar vesicles, are spherical vesicles comprised of one lipid bilayer membrane which defines a closed compartment. The bilayer membrane is composed of two layers of lipids; an inner layer and an outer layer. The outer layer of lipid molecules are oriented with their hydrophilic head portions toward the external aqueous environment and their hydrophobic tails pointed downward toward interior of the liposome. The inner layer of lipid lays directly beneath the outer layer; the lipids are oriented with their heads facing the aqueous interior of the liposome and their tails toward the tails of outer layer of lipid.

Multilamellar liposomes, also referred to as multilamellar vesicles, are composed of more than one lipid bilayer membrane, which membranes define more than one closed compartment. The membranes are concentrically arranged so that the different membranes are separated by compartments much like an onion skin.

Thus, some or all of the compound of the invention is located in one or more of the compartments of a liposome or micelle, or the compound of the invention is bound to the membrane of the liposome. Where a compound is bound to a lipid membrane, at least the lactone ring of some or all of the compound of the invention binds to the lipid membrane of the liposome, and where the liposome contains more than one bilayer membrane the compound of the invention is bound to at least 1 membrane. Those compounds of the invention that have a high affinity for such membrane tend to remain bound to the membrane. Those compounds of the invention with a low affinity for liposome membrane, will at least partially disassociate from the liposome membrane and reside in the liposome compartment.

Micelles as defined herein are spherical receptacles comprised of a single, monolayer membrane which defines a closed compartment and the membrane is comprised of surfactant molecules oriented so that the hydrocarbon tails are oriented toward the compartment and the polar head portions are oriented toward the external aqueous environment. The compounds of the invention, when associated with micelles, are either in the compartment, bound to the micelle membrane, or bound to the outside surface of the micelle.

Liposomes have been used successfully to administer medications to cancer patients, and have been shown to be useful clinically in the delivery of anticancer drugs such as doxorubicin, daunorubicin, and cisplatinum complexes. Forssen, et al., Cancer Res. 1992, 52: 3255-3261; Perex-Soler, et al., Cancer Res. 1990, 50: 4260-4266; and, Khokhar, et al., J. Med. Chem. 1991, 34: 325-329, all of which are incorporated herein in their entireties by reference.

Similarly, micelles have also been used to deliver medications to patients, (Broden et al., Acta Pharm Suec. 19: 267-284 (1982)) and micelles have been used as drug carriers and for targeted drug delivery, (D. D. Lasic, Nature 335: 279-280 (1992); and, Supersaxo et al., Pharm Res. 8: 1280-1291 (1991)), including cancer medications, (Fung et al., Biomater. Artif. Cells. Artif. Organs 16: 439 et seq. (1988); and Yokoyama et al., Cancer Res. 51: 3229-3236 (1991)), all of which are incorporated herein in their entireties by reference.

The liposomes and/or micelles containing the compound of the invention can be administered to a cancer patient, typically intravenously. The liposomes and/or micelles are carried by the circulatory system to the cancer cells where the membrane of the vesicle fuses to the membrane of the cancer cell thereby releasing the compound of the invention to the cancer cell, or where the liposomes and/or micelles to be taken up by the cancer cells, the compound of the invention diffuses from the liposomes and/or micelles to be taken up by the cancer cells.

Any lipid mixture of lipids which forms liposomes and/or micelles is suitable for use in the present invention. Phosphatidylcholines, including, for example, L-α-dimyristoylphosphatidylcholine (DPMC), 1-α-dipalmitoylphosphatidylcholine (DPPC) and L-α-distearoylphosphatidylcholine (DSPC) are suitable. Also, phosphatidylglycerols, including, for example, L-α-dimyristoylphosphatidylglycerol (DMPG) are suitable. The DMPC and DMPG are both fluid phase at 37, for example, L-α-dimyristoylphosphatidylglycerol (DMPG) are suitable. The DMPC and DMPG are both fluid phase at 37° C., while DSPC is solid phase at 37° C. Since the presence of negatively charged lipid in the liposome membrane causes the liposomes to repel each other, small amounts, such as, for example about 10%, of an negatively charged lipid, such as distearolphosphotidylglycerol (DSPG), may be incorporated in to the DSPC liposomes. Other suitable phospholipids include: phosphatidyl-ethanolamides, phosphatidylinositols, and phosphatidic acids containing lauric, myristic, palmitic, paimitoleic, stearic, oleic, linoleic, arachidonic, behenic and lignoceric acid. Another suitable lipid includes cholesterol.

U.S. Pat. No. 6,096,336 provides further guidance for preparing liposomal compositions useful in this invention and is incorporated herein by reference.

The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

EXAMPLES

In the following descriptions, optical rotations were measured at 20-25° C. with an Atago Polax-2 L polarimeter. $^{1}H$ and $^{13}C$ spectra were recorded on a Varian Unity Inova NMR Spectrometer operating at 300 and 75 MHz, respectively. Chemical shifts are referenced to the solvent used (7.27 and 77.23 ppm for $CDCl_3$, 3.31 and 49.15 ppm for $CD_3OD$) unless otherwise stated. Electrospray-ionization mass spectra (ESIMS) were acquired using Thermo Finnigan LCQ Advantage mass spectrometer.

The chromatographic purity of the products was assessed using Waters Alliance 2695 separation modules with Waters 2996 PDA detector HPLC system using a gradient of water and acetonitrile, and TLC on silica gel 60 $F_{254}$ (APCO, China). TLC plates were visualized by using either the UV lamp or anisaldehyde stain (by volume: 93% ethanol, 3.5% sulfuric acid, 1% acetic acid and 2.5% anisaldehyde). Chromatographic separations were performed using silica gel (APCO, China; 300-400 μm mesh size).

All chemicals were obtained from commercial sources and used as received unless otherwise stated. All experiments were conducted under an atmosphere of dry argon. Only the 20(S)-camptothecin (CPT) derivative was used in all the experiments.

Unless otherwise stated all temperatures are in degrees Celsius. Also, in these examples and elsewhere, abbreviations have the following meanings:

μL=microliter
Boc=tert-butoxycarbonyl
d=doublet
dd=double doublet
g=gram
kg=kilogram
hr=hour
Hz=hertz
L=liter
M=molar
nM=nanomolar
m=multiplet
m/z=mass to charge ratio
EtOH=ethanol
$H_2SO_4$=sulfuric acid
$HNO_3$=nitric acid $Et_2O$=diethyl ether
EtOAc=ethyl acetate
MeOH=methanol
mg=milligram
MHz=mega Hertz
min=minute
mL=milliliter
mmol=millimole
mol=mole
N=normal
NaOEt=sodium ethoxide
NMR=nuclear magnetic resonance
q=quartet
s=singlet
t=triplet
$(NH_4)_2SO_4$=ammonium sulfate
$Et_2O$=diethyl ether
$Na_2SO_4$=sodium sulfate
HCl=hydrochloric acid
AcOH=acetic acid
DCM=dichloromethane
DMAP=4-dimethylaminopyridine
ESI MS=electrospray Ionization Mass Spectrometry
$NaHCO_3$=sodium bicarbonate
TFA=trifluoroacetic acid
Hobt=1-hydroxy benzotriazole
DCC=N,N'-dicyclohexylcarbodiimide
DIC=N,N'-diisopropylcarbodiimide
DMF=N,N-dimethylformamide
rt=room temperature
aq=aqueous
ppm=parts per million
μm=micrometer
Gy=gray Synthesis of Staring Materials A. 2,4,5,7-tetranitrofluorenone (1, TNF)

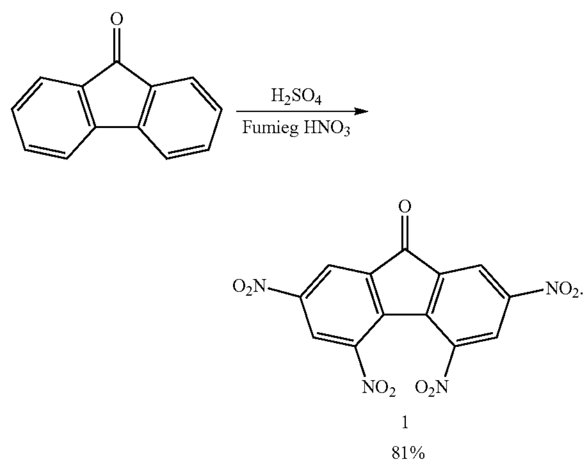

The synthesis of 2,4,5,7-tetranitrofluorenone (1, TNF) was adapted from Melvin, S et al., *Organic Synthesis,* 1962, 42, 95-6. Briefly, to a suspension of 9-fluorenone (62.5 g, 346.84 mmol) in conc. $H_2SO_4$ (300 mL) was added fuming nitric acid (236 mL, 5.205 mol) slowly. The reaction mixture was heated to gentle reflux (~140° C. bath temp) for 8 hr, then stirred at rt overnight. The reaction mixture was poured into water (3 L) and the light yellow precipitate was washed with water, dried at rt overnight, then at low vacuum at 80° C. for 2 days to afford 101.8 g of TNF 1 as yellow solid (81%). $^1H$ NMR (acetone-$d_6$): δ 9.05 (s, 2H, Ar), 8.87 (s, 2H, Ar); M.p. 253-255° C.

B. (±)-α-(isopropylideneaminooxy)propionic acid (2)

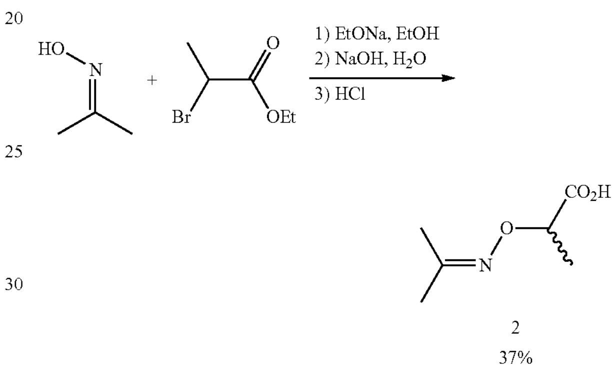

The synthesis of (±)-α-(isopropylideneaminooxy)propionic acid (2) was adapted from Melvin, S et al., *Organic Syntheses,* 1973, Coll. Vol. 5, 1029-37. Briefly, to a freshly prepared 1 M NaOEt solution (35 g in 1 L) was added acetone oxime (110 g, 1.505 mol) and cooled to 0° C. Ethyl α-bromopropionate (175 mL, 1.347 mol) was added at a rate that such that the temperature of the reaction mixture did not rise above 20° C. After 18 hr at rt, the mixture was filtered and the filtrate was concentrated to approximately 500 mL. Water (500 mL) was added and the mixture was extracted with 1:1 benzene:$Et_2O$ (3×150 mL). The combined extracts were washed with water (500 mL), dried over $Na_2SO_4$ and the solvent was removed and the oily residue was distilled to afford 197 g of ethyl α-(isopropylideneaminooxy)propionate as a clear oil (83%) $^1H$ NMR ($CDCl_3$): δ 4.5 (q, 1H, J=6.9 Hz, CH), 4.1 (m, 2H, J=7.2 Hz, O—$CH_2$-Me), 1.84 (s, 3 H, $CH_3$), 1.61 (s, 3 H, $CH_3$), 1.22 (d, 3 H, J=6.9 Hz, CH—$CH_3$), 1.17 (t, 3H, J=7.2 Hz, —$CH_3$); B.P. 62-64° C. (4 mm).

The ethyl α-(isopropylideneaminooxy)propionate was added to 5% NaOH solution (1.2 L) at 70° C. After 20 min, the solution was cooled to rt and acidified to pH 2.0 with 5N HCl solution. Then to the solution was added $(NH_4)_2SO_4$ (500 g) and the mixture was extracted with 1:1 benzene:$Et_2O$ (2×300 mL). The combined organic extracts were dried over $Na_2SO_4$ and concentrated to approximately 200 mL. Petroleum ether (500 mL) was added and the solution was cooled to −20° C. overnight. The recrystallized product was recovered by filtration. 80 g of product 2 was recovered as a white solid (37%).

$^1$H NMR ($CDCl_3$): δ 4.64 (q, 1H, J=6.9 Hz, CH), 1.93 (s, 3 H, $CH_3$), 1.90 (s, 3 H, $CH_3$), 1.50 (d, 3H, J=6.9 Hz, $CH_3$); M.p. 59-61° C.

C. (+)-α-(isopropylideneaminooxy)propionic acid (2a)

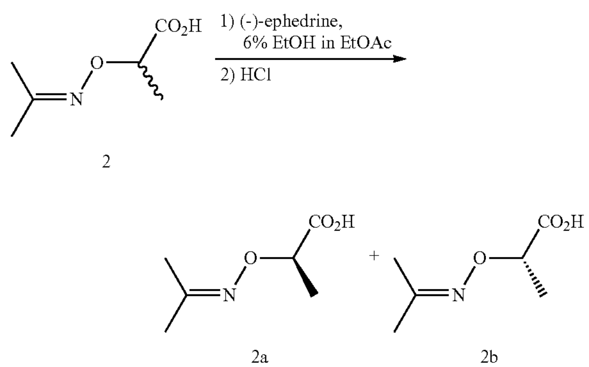

The synthesis of (+)-α-(isopropylideneaminooxy)propionic acid (2a) was adapted from Melvin, S et al., *Organic Syntheses,* 1973, Coll. Vol. 5, 1029-37. Briefly, (−)-ephedrine hydrochloride (40 g, 200 mmol) was dissolved in water (200 mL) and added 2N NaOH solution (120 mL). The mixture was extracted with EtOAc (3×100 mL), dried over $Na_2SO_4$ and filtered. EtOH (50 mL) was added and the mixture was diluted with EtOAc (450 mL). (±)-α-(isopropylideneaminooxy)propionic acid (29 g, 200 mmol) was added and the mixture was allowed to remain undisturbed at 4° C. for 16 hr. The crystalline (−)ephedrine-(+)-α-(isopropylideneaminooxy)propionic acid salt was recovered by filtration and the dried crystals were recrystallized in EtOAc (250 mL). The crystalline solid was dissolved in water (60 mL) and treated with 5N HCl solution (14 mL). The solution was extracted with 1:1 benzene:$Et_2O$ (3×50 mL). The combined extracts were dried over $Na_2SO_4$ and filtered. The solvent was removed and remaining residue was recrystallized in petroleum ether (75 mL) at −20° C. overnight. Recovered 7.6 g of (+)-α-(isopropylideneaminooxy)propionic acid 2a. $[\alpha]^{21.4}_D$=+ 33.3° (c=1.05).

D. (−)-α-(isopropylideneaminooxy)propionic acid (2b)

The synthesis of (−)-α-(isopropylideneaminooxy)propionic acid (2b) was adapted from Melvin, S et al., *Organic Syntheses,* 1973, Coll. Vol. 5, 1029-37. Briefly, the EtOAc filtrate from preparation of (+)-.α-(isopropylideneaminooxy) propionic acid was diluted with an equal volume of petroleum ether and cooled to 0° C. for 16 hr and filtered. The crystalline solid was dissolved in water (60 mL) and treated with 5N HCl solution (14 mL). The solution was extracted with 1:1 benzene:$Et_2O$ (3×50 mL). The combined extracts were dried over $Na_2SO_4$ and filtered. The solvent was removed and remaining residue was recrystallized in petroleum ether (75 mL) at −20° C. overnight. 5.2 g of (−)-α-(isopropylideneaminooxy)propionic acid 2b was recovered. $[\alpha]^{19.0}_D$=−33° (c=2.00).

E. (+)-α-(2.4.5.7-Tetranitro-9-fluorenylideneaminooxy)propionic acid (3a, (+)TAPA)

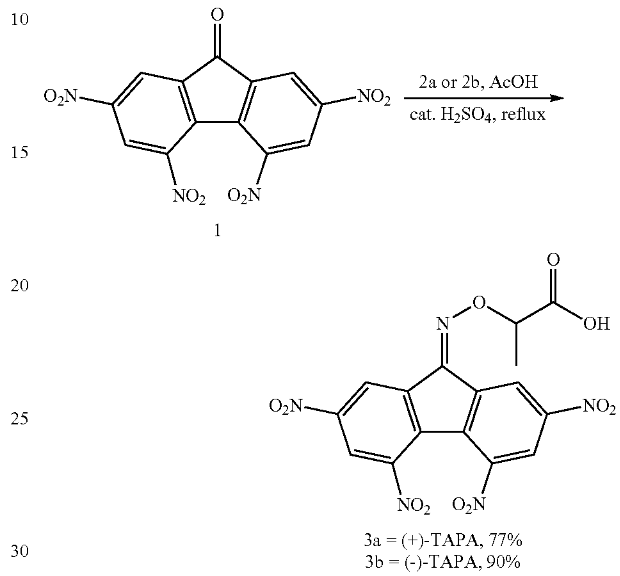

The synthesis of (+)-α-(2.4.5.7-Tetranitro-9-fluorenylideneaminooxy)propionic acid (3a, (+)TAPA) was adapted from Melvin, S et al., *Organic Syntheses,* 1973, Coll. Vol. 5, 1029-37. Briefly, (+)-α-(isopropylideneaminooxy)propionic acid (12.3 g, 84.73 mmol) and 2,4,5,7-tetranitrofluorenone (25.2 g, 70.61 mmol) were dissolved in glacial AcOH (565 mL) and concentrated $H_2SO_4$ (1.41 mL) was added. The mixture was refluxed at 130° C. for 2 hr. The reaction mixture was added to water (500 mL), cooled to 0° C. overnight and filtered. The solid was dried at rt overnight, followed by drying under high vacuum at 100° C. overnight to afford 15 g of (+)TAPA 3a as a yellow solid (77%). $^1$H NMR (acetone-$d_6$): δ 9.58 (s, 1H, Ar), 8.98 (s, 2H, Ar), 8.92 (s, 1H, Ar), 5.32 (q, 1H, J=6.9 Hz, CH), 1.93 (d, 3H, J=6.9 Hz, $CH_3$); M.p. 201-203° C. (dec); $[\alpha]^{21}_D$=−97°.

F. (−)-α-(2.4.5.7-Tetranitro-9-fluorenylideneaminooxy)propionic acid (3 b, (−)TAPA)

The synthesis of (−)TAPA was similar to the preparation of (+)TAPA. Briefly, (−)-α-(isopropylideneaminooxy)propionic acid (5 g, 34.44 mmol) and 2,4,5,7-tetranitrofluorenone (8.3 g, 22.96 mmol) were dissolved in glacial AcOH (184 mL) and concentrated $H_2SO_4$ (0.46 mL) was added. The mixture was refluxed at 130° C. for 2 hr. The reaction mixture was added to water (100 mL), cooled to 0° C. overnight and filtered. The solid was dried at rt overnight, followed by drying under high vacuum at 100° C. overnight to afford 8.23 g of (−)TAPA 3b as a yellow solid (80%). $^1$H NMR (acetone-d6): δ 9.58 (s, 1H, Ar), 8.98 (s, 2H, Ar), 8.92 (s, 1H, Ar), 5.32

(q, 111, J=6.9 Hz, CH), 1.93 (d, 3H, J=6.9 Hz, CH3); M.p. 201-203° C. (dec); $[\alpha]^{21}_{D}$=+97°, G. 2.4.5.7-Tetranitro-9-fluorenylideneaminooxy ethanoic acid (4, TNF-ethanoic acid)

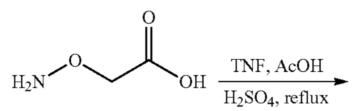

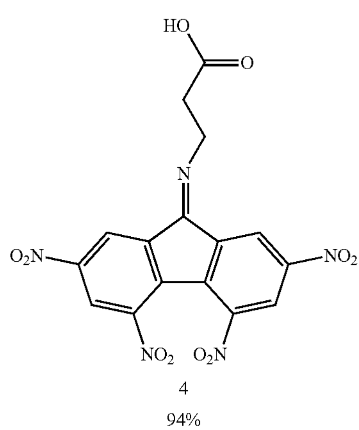
4
94%

To a solution of tetranitrofluorenone (40 g, 111.11 mmol) in glacial AcOH (370 mL) was added carboxymethoxylamine hemihydrochloride (24.3 g, 222.22 mmol) and conc. $H_2SO_4$ (2.22 mL). The mixture was refluxed for 3 hr (~150° C. bath temp) and while the solution was still hot, deionized water (100 mL) was added. The mixture was cooled to 0° C. overnight and the precipitate was recovered by filtration. The solid was washed with water and dried under high vacuum overnight, followed by drying at 100° C. under high vacuum for 3 days to afford 45.2 g of product 4 as a yellow solid (94%). $^{1}H$ NMR (acetone-d6): δ 9.59 (s, 1H, Ar), 9.02 (s, 1H, Ar), 8.95 (s, 1H, Ar), 8.93 (s, 1H, Ar), 5.38 (s, 2H, $CH_2$); $^{13}C$ NMR (acetone-d6): δ 127.01, 123.03, 122.03, 120.44, 73.57. M.p. 203-205° C., ESIMS: calcd for $C_{15}H_7N_5O_{11}$ [M−H]− 432.01, found 432, 865.2 (dimer).

H. 9-fluorenylideneaminooxy ethanoic acid (5, 9F-ethanoic acid)

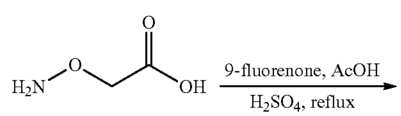

-continued

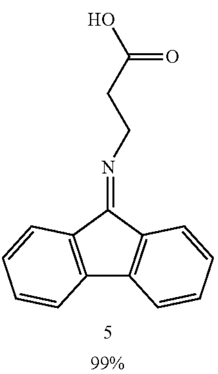
5
99%

To a solution of 9-fluorenone (2 g, 11.10 mmol) in glacial AcOH (56 mL) was added carboxymethoxylamine hemihydrochloride (2.43 g, 22.20 mmol) and conc. $H_2SO_4$ (221 μL). The mixture was refluxed for 3 hr (~150° C. bath temp) and while the solution was still hot, deionized water (50 mL) was added. The mixture was cooled to 0° C. overnight and the precipitate was recovered by filtration. The solid was washed with water and dried under high vacuum overnight, followed by drying at 100° C. under high vacuum overnight to afford 2.78 g of product 5 as a light yellow solid (99%). $^{1}H$ NMR (1:1 $CDCl_3$: acetone-$d_6$): δ 8.30 (dd, 1H, J=0.9, 7.5 Hz, Ar), 7.66-7.61 (m, 3H, Ar), 7.41-7.17 (m, 4H, Ar), 4.91 (s, 2H, $CH_2$); $^{13}C$ NMR (acetone-d6): δ 131.74, 130.62, 129.82, 128.58, 128.29, 121.72, 120.49, 120.38, 71.89; M.p. 231-233° C., ESIMS: calcd for $C_{15}H_{11}NO_3$ [M−H]− 252.07, found 252.3.

I. (±)-9-fluorenylideneaminooxy propionic acid (6, 9F-propionic acid)

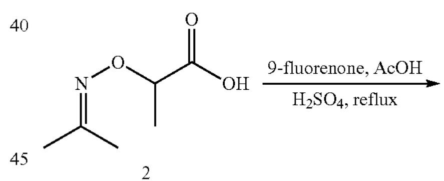

2

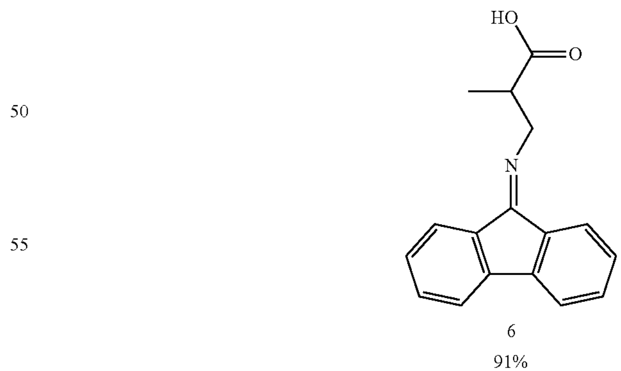
6
91%

To a solution of 9-fluorenone (2 g, 11.10 mmol) in glacial AcOH (89 mL) was added (±)-(isopropylideneaminooxy) propionic acid 2 (1.93 g, 13.32 mmol) and conc. $H_2SO_4$ (222 μL). The mixture was refluxed for 3 hr (~150° C. bath temp) and while the solution was still hot, deionized water (50 mL) was added. The mixture was cooled to 0° C. overnight and the precipitate was recovered by filtration. The solid was washed with water and dried under high vacuum overnight, followed by drying at 100° C. under high vacuum overnight to afford 2.7 g of product 6 as a light yellow solid (91%). $^{1}H$ NMR (acetone-d6): δ 8.40 (d, 1H, J=7.5 Hz, Ar), 7.84-7.77 (m, 2H, Ar), 7.71 (d, 1H, J=8.4 Hz, Ar), 7.54-7.29 (m, 4H, Ar), 5.03 (q, 1H, J=6.9 Hz, CH), 1.70 (d, 1H, J=6.9 Hz, $CH_3$); $^{13}C$ NMR (acetone-d6): δ 131.67, 130.55, 129.78, 128.58, 128.26, 121.68, 120.46, 120.36, 79.12, 16.97; M.p. 174-176° C., ESIMS: calcd for $C_{16}H_{13}NO_3$ $[M-H]^-$ 266.09, found 266.1.

Synthesis of Compounds of the Invention

The invention is further understood by reference to the following examples, which are intended to be purely exemplary of the invention.

Example 1

10-tert-butoxycarbonyloxycamptothecin (7, Boc-10H-CPT)

$(BOC)_2O$, DMF, pyridine 7
94%

$(BOC)_2O$ (12 g, 54.79 mmol) and 10-hydroxy-camptothecin (10 g, 27.40 mmol) were dissolved in DMF (137 mL) and pyridine (46 mL) was added. The mixture was stirred at rt overnight. The reaction mixture was diluted with DCM (800 mL) and washed with water (3×300 mL), 1 N HCl (3×300 mL) and dried over $Na_2SO_4$. The solvent was evaporated to give 12 g of crude product 7 (94%). $^{1}H$ NMR ($CDCl_3$): δ 8.34 (s, 1 H, Ar), 8.25 (s, 1H, Ar), 8.21 (s, 1H, Ar), 7.75 (d, 1 H, J=2.4 Hz, Ar), 7.67 (s, 1 H), 7.66 (dd, J=8.0, 2.4 Hz, 1 H, Ar), 5.75 (d, J=16.5 Hz, 1H, —C—$CH_2$—O—C(O)—), 5.31 (d, J=16.5 Hz, 1 H, 5.30 (s, 2 H, —C—$CH_2$—N—), 1.91 (m, J=6 Hz, 2H, $CH_2$-Me), 1.62 (s, 9 H, t-Bu), 1.06 (t, J=6 Hz, 3H, $CH_3$).

20-O-(TNF-ethanoyl)-Boc-10H-CPT ester (8)

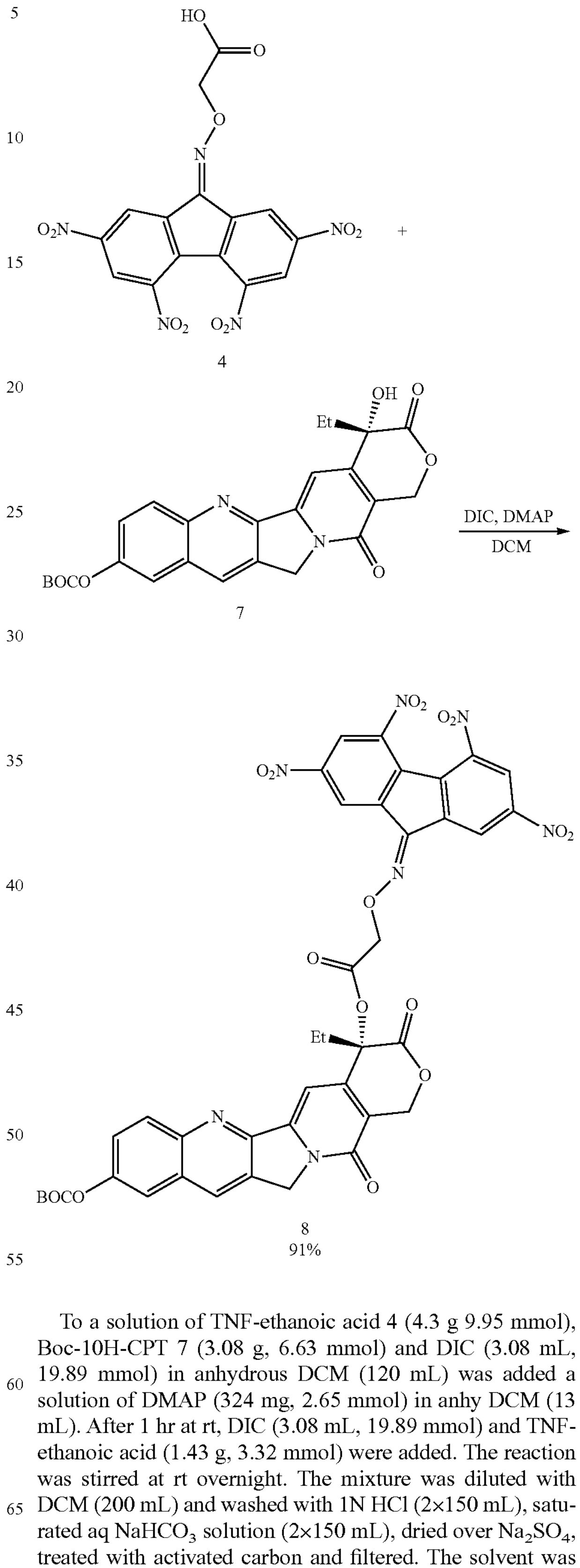

To a solution of TNF-ethanoic acid 4 (4.3 g 9.95 mmol), Boc-10H-CPT 7 (3.08 g, 6.63 mmol) and DIC (3.08 mL, 19.89 mmol) in anhydrous DCM (120 mL) was added a solution of DMAP (324 mg, 2.65 mmol) in anhy DCM (13 mL). After 1 hr at rt, DIC (3.08 mL, 19.89 mmol) and TNF-ethanoic acid (1.43 g, 3.32 mmol) were added. The reaction was stirred at rt overnight. The mixture was diluted with DCM (200 mL) and washed with 1N HCl (2×150 mL), saturated aq $NaHCO_3$ solution (2×150 mL), dried over $Na_2SO_4$, treated with activated carbon and filtered. The solvent was evaporated and the remaining residue was purified by silica gel column with 50-80% EtOAc:Hexanes to give 5.3 g of 20-O-(TNF-ethanoyl)-Boc-10H-CPT ester 8 as a yellow solid (91%). $^{1}$H NMR (acetone-$d_6$) δ 9.5 (s, 1H, tetranitrofluorenone), 8.94 (s, 1H, tetranitrofluorenone), 8.69 (s, 1H, tetranitrofluorenone), 8.60 (s, 1H, tetranitrofluorenone), 8.56 (s, 1H, Ar), 7.94 (d, 1H, J=9.0 Hz, Ar), 7.81 (s, 1H, Ar), 7.59 (dd, 1H, J=2.7, 9.0 Hz, Ar), 7.20 (s, 1H), 5.66-5.37 (m, 4H, —C—$CH_2$—O—C(O)— and —C—$CH_2$—N—), 5.30 (s, 2H, O—C(O)—$CH_2$—O—), 2.30 (m, 2H, J=7.2 Hz, $CH_2$-Me), 1.58 (s, 9H, t-Bu), 0.97 (t, 3H, J=7.2 Hz, $CH_3$); $^{13}$C NMR ($CDCl_3$): δ 167.12, 166.99, 157.30, 152.13, 150.23, 149.09, 148.54, 146.57, 146.42, 144.57, 140.65, 133.93, 131.30, 130.82, 129.34, 128.70, 127.30, 126.29, 122.68, 121.66, 121.14, 120.83, 118.68, 95.98, 84.90, 73.70, 67.70, 50.39, 32.35, 28.07, 7.95; M.p. 205-207° C. (dec), ESIMS: calcd for $C_{40}H_{29}N_7O_{17}$ $[M+H]^+$ 880.16, found 880.4.

By substituting other camptothecin analogs for Boc-10H-CPT 7 in step 1 of this example other compounds of this invention are prepared. Other camptothecin analogs include the following:

(20S)-9-nitro CPT;
(20S)-7-chloro-n-propyldimethylsilyl CPT;
(20S)-10-hydroxy-7-chloro-n-propyldimethylsilyl CPT;
(20S)-10-acetoxy-7-chloro-n-propyldimethylsilyl CPT;
(20S)-7-tert-butyldimethylsilyl CPT;
(20S)-10-hydroxy-7-tert-butyldimethylsilyl CPT;
(20S)-10-acetoxy-7-tert-butyldimethylsilyl CPT;
(20S)-9-hydroxy CPT;
(20S)-9-amino CPT;
(20S)-10-amino CPT;
(20S)-9-amino-10-hydroxy CPT;
(20S)-9-methylamino CPT;
(20S)-9-chloro CPT;
(20S)-9-fluoro CPT;
(20S)-9-piperidino CPT;
(20S)-9-morpholinomethyl CPT;
(20S)-9,10-dichloro CPT;
(20S)-10-bromo CPT;
(20S)-10-chloro CPT;
(20S)-10-methyl CPT;
(20S)-10-fluoro CPT;
(20S)-10-nitro CPT;
(20S)-10,11-methylenedioxy CPT;
(20S)-10-formyl CPT;
(20S)-10-nonylcarbonyloxy CPT;
(20S)-10-undecylcarbonyloxy CPT;
(20S)-10-heptadecylcarbonyloxy CPT;
(20S)-10-nonadecylcarbonyloxy CPT;
(20S)-9-nitro-10,11-methylenedioxy CPT;
(20S)-9-(4-methylpiperazinylmethyl)-10-hydroxy (CPT);
(20S)-9-[4-(1-piperidino)-1-piperidinomethyl]-10-hydroxy CPT;
(20S)-9-methyl-10,11-methylenedioxy CPT;
(20S)-9-chloro-10,11-methylenedioxy CPT;
(20S)-9-cyano-10,11-methylenedioxy CPT;
(20S)-9-acetoxy-10,11-methylenedioxy CPT;
(20S)-9-acetylamino-10,11-methylenedioxy CPT;
(20S)-9-aminomethyl-10-hydroxy CPT;
(20S)-9-ethoxymethyl-10-hydroxy CPT;
(20S)-9-methylaminomethyl-10-hydroxy CPT;
(20S)-9-n-propylaminomethyl-10-hydroxy CPT;
(20S)-9-dimethylaminomethyl-10-hydroxy CPT;
(20S)-9-cyclohexylaminomethyl-10-hydroxy CPT;
(20S)-9-(2-hydroxyethyl)aminomethyl-10-hydroxy CPT;
(20S)-9-(trimethylammonio)methyl-10-hydroxy CPT, methanesulfonate;
(20S)-9-morpholinomethyl-10-hydroxy CPT;
(20S)-5-(2-hydroxyethoxy) CPT
(20S)-9-cyanomethyl-10-hydroxy CPT;
(20S)-CPT-7-aldehyde;
(20S)-10-methoxy CPT-7-aldehyde;
(20S)-7-acetoxymethyl CPT;
(20S)-7-acetoxymethyl-10-methyl CPT;
(20S)-7-cyano-10-methoxy CPT;
(20S)-7-cyano CPT;
(20S)-7-formylethenyl CPT;
(20S)-7-ethoxycarbonylethenyl CPT;
(20S)-7-cyanoethenyl CPT;
(20S)-7-(2,2-dicyanoethenyl) CPT;
(20S)-7-(2-cyano-2-ethoxycarbonyl)ethenyl CPT;
(20S)-7-ethoxycarbonylethyl CPT;
(20S)-7-ethyl CPT;
(20S)-7-n-propyl CPT;
(20S)-7-acetoxymethyl CPT;
(20S)-7-n-propylcarbonyloxymethyl CPT;
(20S)-7-ethoxycarbonyl CPT;
(20S)-7-ethyl-10-hydroxy CPT;
(20S)-7-ethyl-10-acetyloxy CPT;
(20S)-7-methyl-10-aminocarbonyloxy CPT;
(20S)-7-n-propyl-10-piperidinocazbonyloxy CPT;
(20S)-7-ethyl-10-(2-dimethylamino)ethyl CPT; and
(20S)-7-ethyl-10-carbamoyloxy derivatives of CPT such as (20S)-7-ethyl-10-[4(1-piperidino)-piperidino]carbonyloxy CPT;
(20S)-7-ethyl-10-(1-piperazine)carbonyloxy CPT;
(20S)-7-ethyl-10-(4-i-propylaminocarbonylmethylpiperazine)carbonyloxy CPT;
(20S)-7-ethyl-10-[4(1-pyrrolidinyl)piperazine]carbonyloxy CPT;
(20S)-7-ethyl-10-[(4-(dimethylamino)-1-piperidino]carbonyloxy CPT;
(20S)-7-ethyl-10-[4-(di-n-propylamino)-1-piperidinol]carbonyloxy CPT;
(20S)-7-ethyl-10-[(4-(di-n-butylamino)-1-piperidino]carbonyloxy CPT;
(20S)-7-ethyl-10-[4-(1-pyrrolidino)-1-piperidino)]carbonyloxy CPT;
(20S)-7-ethyl-10-[4-(1-piperidino)-1-piperidino]carbonyloxy CPT;
(20S)-7-ethyl-10-[N-methyl-N-2-(dimethylamino)ethylamino]carbonyloxy CPT
(20S)-7-(tert-butyldimethylsilyl) CPT
(20S)-7-(tert-butoxyiminomethyl) CPT (Gimatecan)
(20S)-7-butyl-10,11-methylenedioxy CPT
(20S)-7-bromomethyl-10-hydroxy CPT
(20S)-7-butyl-10-amino CPT
(20S)-7-(tert-butyldimethylsilyl)-10-hydroxy CPT
(20S)-7-[(2-trimethylsilyl)ethyl)] CPT (Karentican)
(20S)-7-[(4-fluorophenoxy)acetyloxymethyl] CPT
(20S)-7-[(4-methoxyphenoxy)acetyloxymethyl] CPT
(20S)-7-[(4-cyano-3-fluorophenoxy)acetyloxymethyl] CPT
(20S)-7-[(3,4,5-trimethoxyphenyl)acetyloxymethyl] CPT
(20S)-10-[(4-cyano-3-fluorophenoxy)acetyloxy] CPT
(20S)-10-[(3,4,5-trimethoxyphenyl)acetyloxy] CPT
(20S)-7-(4-methylpiperazinomethylene)-10,11-ethylenedioxy CPT (Exatecan)
(20S)-7-(2-(N-isopropylamino)ethyl) CPT (Belotecan)
(20S)-[5(RS)-(2-hydroxyethoxy)] CPT
(20S)-7-ethyl-9-allyl-10-hydroxy CPT (29)
(20S)-7-ethyl-9-allyl-10-methoxy CPT (29)
(20S)-7-ethyl-9-propyl-10-hydroxy CPT (29)
(20S)-7-ethyl-9-propyl-10-methoxy CPT (29)
(20S)-7,9-diethyl-10-hydroxy CPT (29)

(20S)-7,9-diethyl-10-methoxy CPT (29)
(20S)-10-(substituted quaternary ammonium salts) CPT
(20S)-7-(tris(hydroxymethyl)methylamino)methyl CPT
(20S)-7-(bis(hydroxymethyl)methylamino)methyl CPT
(20S)-7-(2-hydroxyethylamino)methyl CPT
(20S)-7-(tris(hydroxymethyl)methylamino)methyl-10,11-methylenedioxy CPT
(20S)-7-(bis(hydroxymethyl)methylamino)methyl-10,11-methylenedioxy CPT
(20S)-7-(2-hydroxyethylamino)methyl-10,11-methylenedioxy CPT
(20S)-7-(tris(hydroxymethyl)methylamino)methyl-10-[4-(1-piperidino)-1-piperidino]carbonyloxy) CPT
(20S)-7-(bis(hydroxymethyl)methylamino)methyl-10-[4-(1-piperidino)-1-piperidino]carbonyloxy) CPT
(20S)-7-(2-hydroxyethylamino)methyl-10-[4-(1-piperidino)-1-piperidino]carbonyloxy) CPT
(20S)-7-(tris(hydroxymethyl)methylamino)methyl-9-dimethylaminomethyl-10-hydroxy CPT
(20S)-7-(bis(hydroxymethyl)methylamino)methyl-9-dimethylaminomethyl-10-hydroxy CPT
(20S)-7-(2-hydroxyethylamino)methyl-9-dimethylaminomethyl-10-hydroxy CPT
(20S)-7-(tris(hydroxymethyl)methylamino)methyl-9-amino CPT
(20S)-7-(bis(hydroxymethyl)methylamino)methyl-9-amino CPT
(20S)-7-(2-hydroxyethylamino)methyl-9-amino CPT
(20S)-7-(tris(hydroxymethyl)methylamino)methyl-9-nitro CPT
(20S)-7-(bis(hydroxymethyl)methylamino)methyl-9-nitro CPT
(20S)-7-(2-hydroxyethylamino)methyl-9-nitro CPT
(20S)-7-(tris(hydroxymethyl)methylamino)methyl-10-hydroxy CPT
(20S)-7-(bis(hydroxymethyl)methylamino)methyl-10-hydroxy CPT
(20S)-7-(2-hydroxyethylamino)methyl-10-hydroxy CPT; and the like.

Example 2

20-O-[(+)TAPA]-Boc-10H-CPT ester (9)

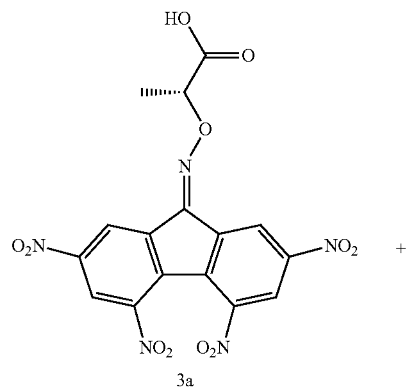

3a

-continued

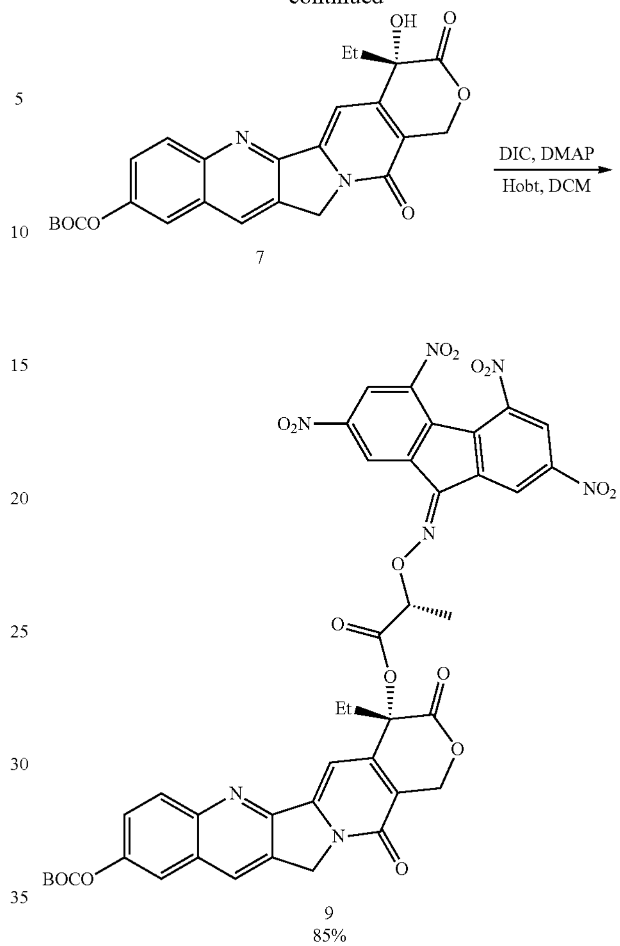

7

9
85%

To a solution of (+)TAPA 3a (360 mg, 0.81 mmol), Boc-10H-CPT 7 (250 mg, 0.54 mmol), Hobt (80 mg, 0.59 mmol) and DIC (250 μL, 1.61 mmol) in anhy DCM (10 mL) was added a solution of DMAP (26 mg, 0.22 mmol) in ashy DCM (1 mL). After 1 hr at rt, DIC (250 μL, 1.61 mmol) and (+)TAPA 3a (120 mg, 0.27 mmol) were added. The reaction was stirred at rt overnight. The mixture was diluted with DCM (50 mL) and washed with 1N HCl (2×25 mL), saturated aq $NaHCO_3$ solution (2×25 mL), dried over $Na_2SO_4$, treated with activated carbon and filtered. The solvent was evaporated and the remaining residue was purified by silica gel column with 50-80% EtOAc:Hexanes to give 400 mg of 20-O-[(+)TAPA]-Boc-10H-CPT ester 9 as yellow solid (85%). $^1$H NMR ($CDCl_3$) δ 9.40 (s, 1H, Ar), 8.85 (s, 1H, Ar), 8.54 (s, 1H, Ar), 8.33 (s, 2H, Ar), 7.83-7.58 (m, 3H), 7.17 (s, 1H), 5.68 (d, 1H, J=17.4 Hz, —C—$CH_2$—O—C(O)—), 5.52-5.42 (m, 2H, —C—$CH_2$—O—C(O)— and O—C(O)—CH(Me)-O—), 5.28 (s, 2H, —C—$CH_2$—N—), 2.55-2.20 (dm, 2H, $CH_2$-Me), 1.87 (d, 3H, J=7.2 Hz, $CH_3$), 1.63 (s, 9H, t-Bu), 0.97 (t, 3H, J=7.2 Hz, $CH_3$); $^{13}$C NMR (acetone-d6): δ 169.05, 150.30, 149.05, 146.40, 146.22, 144.54, 131.18, 130.63, 129.36, 127.26, 126.40, 122.55, 121.32, 120.54, 118.77, 95.92, 81.03, 67.81, 50.36, 32.48, 28.09, 17.28, 7.95; M.p. 210-215° C. (dec); ESIMS: calcd for $C_{41}H_{31}N_2O_{17}$ $[M+H]^+$ 894.18, found 894.3.

Compound 10

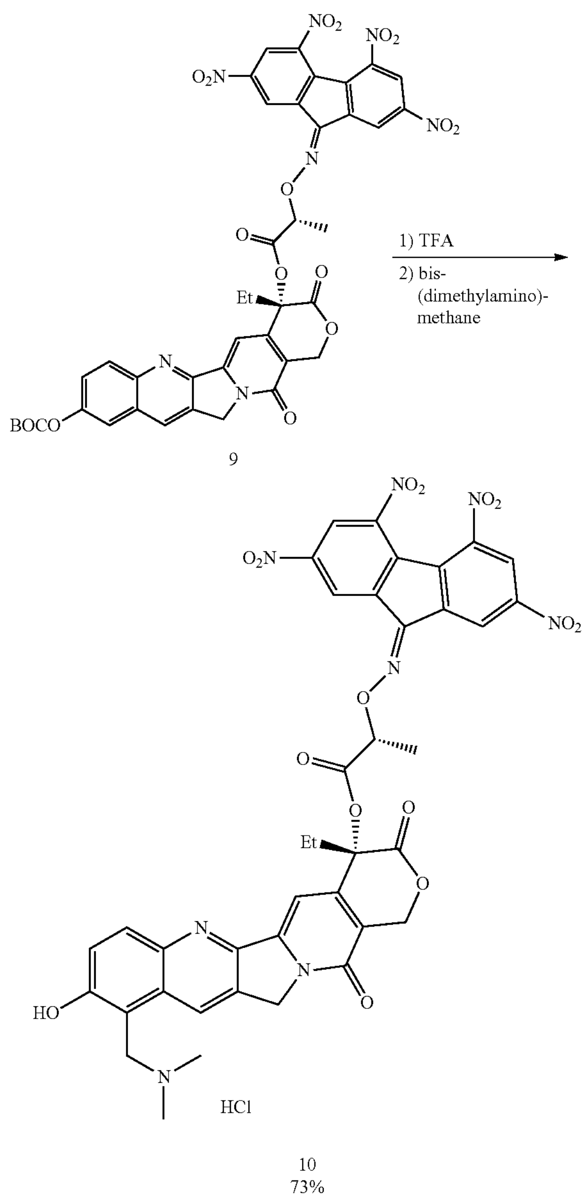

The 20-O-[(+)TAPA]-Boc-10H-CPT ester 7 (4 g, 4.47 mmol) was dissolved in TFA (90 mL). After stirring at rt for 1 hr, bis-(dimethylamine)-methane (30 mL) was added slowly. The mixture was stirred at rt for 45 min and the crude product was precipitated by addition to water. Filtered and the precipitate was dissolved in DCM (300 mL), washed with saturated $NaHCO_3$ solution (3×200 mL, the solution turned red), dried over $Na_2SO_4$, filtered and the solvent was removed. The dark red solid was dissolved in MeOH (100 mL) and added 25 mL of 2M HCl in $Et_2O$. Filtered and the yellow solid was dried under vacuum to afford 2.88 g of 10 as hydrochloride salt (73%). $^1H$ NMR (1:1 $CDCl_3$:$CD_3OD$): δ9.22 (s, 1H, Ar), 8.62 (s, 2H, Ar), 8.31 (s, 1H, Ar), 8.21 (s, 1H, Ar), 7.76 (d, 1H, J=9.3 Hz, Ar), 7.37 (d, 1H, J=9.3 Hz, Ar), 7.29 (s, 1H), 5.46-5.19 (m, 3H), 5.13 (s, 2H, —C—$CH_2$—N—), 4.60 (m, 2H), 2.77 (s, 3H, —N—$CH_3$), 2.72 (s, 3H, —N—$CH_3$), 2.05 (dm, 2H, J=7.5 Hz, —$CH_2$-Me), 1.65 (d, 3H, J=7.2 Hz, $CH_3$), 0.80 (t, 3H, J=7.5 Hz, $CH_3$); M.p. 210-213° C. (dec); ESIMS: calcd for $C_{39}H_{30}N_8O_{15}$ $[M+H]^+$ 851.18, found 851.4.

By substituting other camptothecin analogs for Boc-10H-CPT 7 in step 1 of this example other compounds of this invention are prepared. Other camptothecin analogs include the following:

(20S)-9-nitro CPT;
(20S)-7-chloro-n-propyldimethylsilyl CPT;
(20S)-10-hydroxy-7-chloro-n-propyldimethylsilyl CPT;
(20S)-10-acetoxy-7-chloro-n-propyldimethylsilyl CPT;
(20S)-7-tert-butyldimethylsilyl CPT;
(20S)-10-hydroxy-7-tert-butyldimethylsilyl CPT;
(20S)-10-acetoxy-7-tert-butyldimethylsilyl CPT;
(20S)-9-hydroxy CPT;
(20S)-9-amino CPT;
(20S)-10-amino CPT;
(20S)-9-amino-10-hydroxy CPT;
(20S)-9-methylamino CPT;
(20S)-9-chloro CPT;
(20S)-9-fluoro CPT;
(20S)-9-piperidino CPT;
(20S)-9-morpholinomethyl CPT;
(20S)-9,10-dichloro CPT;
(20S)-10-bromo CPT;
(20S)-10-Chloro CPT;
(20S)-10-methyl CPT;
(20S)-10-fluoro CPT;
(20S)-10-nitro CPT;
(20S)-10,11-methylenedioxy CPT;
(20S)-10-formyl CPT;
(20S)-10-nonylcarbonyloxy CPT;
(20S)-10-undecylcarbonyloxy CPT;
(20S)-10-heptadecylcarbonyloxy CPT;
(20S)-10-nonadecylcarbonyloxy CPT;
(20S)-9-nitro-10,11-methylenedioxy CPT;
(20S)-9-(4-methylpiperazinylmethyl)-10-hydroxy (CPT);
(20S)-9-[4-(1-piperidino)-1-piperidinomethyl]-10-hydroxy CPT;
(20S)-9-methyl-10,11-methylenedioxy CPT;
(20S)-9-chloro-10,11-methylenedioxy CPT;
(20S)-9-cyano-10,11-methylenedioxy CPT;
(20S)-9-acetoxy-10,11-methylenedioxy CPT;
(20S)-9-acetylamino-10,11-methylenedioxy CPT;
(20S)-9-aminomethyl-10-hydroxy CPT;
(20S)-9-ethoxymethyl-10-hydroxy CPT;
(20S)-9-methylaminomethyl-10-hydroxy CPT;
(20S)-9-n-propylaminomethyl-10-hydroxy CPT;
(20S)-9-dimethylaminomethyl-10-hydroxy CPT;
(20S)-9-cyclohexylaminomethyl-10-hydroxy CPT;
(20S)-9-(2-hydroxyethyl)aminomethyl-10-hydroxy CPT;
(20S)-9-(trimethylammonio)methyl-10-hydroxy CPT, methanesulfonate;
(20S)-9-morpholinomethyl-10-hydroxy CPT;
(20S)-5-(2-hydroxyethoxy) CPT
(20S)-9-cyanomethyl-10-hydroxy CPT;
(20S)-CPT-7-aldehyde;
(20S)-10-methoxy CPT-7-aldehyde;
(20S)-7-acetoxymethyl CPT;
(20S)-7-acetoxymethyl-10-methyl CPT;
(20S)-7-cyano-10-methoxy CPT;
(20S)-7-cyano CPT;
(20S)-7-formylethenyl CPT;

(20S)-7-ethoxycarbonylethenyl CPT;
(20S)-7-cyanoethenyl CPT;
(20S)-7-(2,2-dicyanoethenyl) CPT;
(20S)-7-(2-cyano-2-ethoxycarbonyl)ethenyl CPT;
(20S)-7-ethoxycarbonylethyl CPT;
(20S)-7-ethyl CPT;
(20S)-7-n-propyl CPT;
(20S)-7-acetoxymethyl CPT;
(20S)-7-n-propylcarbonyloxymethyl CPT;
(20S)-7-ethoxycarbonyl CPT;
(20S)-7-ethyl-10-hydroxy CPT;
(20S)-7-ethyl-10-acetyloxy CPT;
(20S)-7-methyl-10-aminocarbonyloxy CPT;
(20S)-7-n-propyl-10-piperidinocazbonyloxy CPT;
(20S)-7-ethyl-10-(2-dimethylamino)ethyl CPT; and
(20S)-7-ethyl-10-carbamoyloxy, derivatives of CPT such as
(20S)-7-ethyl-10-[4(1-piperidino)-piperidino]carbonyloxy CPT;
(20S)-7-ethyl-10-(1-piperazine)carbonyloxy CPT;
(20S)-7-ethyl-10-(4-i-propylaminocarbonyl methylpiperazine)carbonyloxy CPT;
(20S)-7-ethyl-10-[4(1-pyrrolidinyl)piperazine]carbonyloxy CPT;
(20S)-7-ethyl-10-[(4-(dimethylamino)-1-piperidino]carbonyloxy CPT;
(20S)-7-ethyl-10-[4-(di-n-propylamino)-1-piperidinol]carbonyloxy CPT;
(20S)-7-ethyl-10-[(4-(di-n-butylamino)-1-piperidino]carbonyloxy CPT;
(20S)-7-ethyl-10-[4-(1-pyrrolidino)-1-piperidino)]carbonyloxy CPT;
(20S)-7-ethyl-10-[4-(1-piperidino)-1-piperidino]carbonyloxy CPT;
(20S)-7-ethyl-10-[N-methyl-N-2-(dimethylamino)ethylamino]carbonyloxy CPT
(20S)-7-(tert-butyldimethylsilyl) CPT
(20S)-7-(tert-butoxyiminomethyl) CPT (Gimatecan)
(20S)-7-butyl-10,11-methylenedioxy CPT
(20S)-7-bromomethyl-10-hydroxy CPT
(20S)-7-butyl-10-amino CPT
(20S)-7-(tert-butyldimethylsilyl)-10-hydroxy CPT
(20S)-7-[(2-trimethylsilyl)ethyl)] CPT (Karentican)
(20S)-7-[(4-fluorophenoxy)acetyloxymethyl] CPT
(20S)-7-[(4-methoxyphenoxy)acetyloxymethyl] CPT
(20S)-7-[(4-cyano-3-fluorophenoxy)acetyloxymethyl] CPT
(20S)-7-[(3,4,5-trimethoxyphenyl)acetyloxymethyl] CPT
(20S)-10-[(4-cyano-3-fluorophenoxy)acetyloxy] CPT
(20S)-10-[(3,4,5-trimethoxyphenyl)acetyloxy] CPT
(20S)-7-(4-methylpiperazinomethylene)-10,11-ethylenedioxy CPT (Exatecan)
(20S)-7-[2-(N-isopropylamino)ethyl] CPT (Belotecan)
(20S)-[5(RS)-(2-hydroxyethoxy)] CPT
(20S)-7-ethyl-9-allyl-10-hydroxy CPT (29)
(20S)-7-ethyl-9-allyl-10-methoxy CPT (29)
(20S)-7-ethyl-9-propyl-10-hydroxy CPT (29)
(20S)-7-ethyl-9-propyl-10-methoxy CPT (29)
(20S)-7,9-diethyl-10-hydroxy CPT (29)
(20S)-7,9-diethyl-10-methoxy CPT (29)
(20S)-10-(substituted quaternary ammonium salts) CPT
(20S)-7-(tris(hydroxymethyl)methylamino)methyl CPT
(20S)-7-(bis(hydroxymethyl)methylamino)methyl CPT
(20S)-7-(2-hydroxyethylamino)methyl CPT
(20S)-7-(tris(hydroxymethyl)methylamino)methyl-10,11-methylenedioxy CPT
(20S)-7-(bis(hydroxymethyl)methylamino)methyl-10,11-methylenedioxy CPT
(20S)-7-(2-hydroxyethylamino)methyl-10,11-methylenedioxy CPT
(20S)-7-(tris(hydroxymethyl)methylamino)methyl-10-[4-(1-piperidino)-1-piperidino]carbonyloxy) CPT
(20S)-7-(bis(hydroxymethyl)methylamino)methyl-10-[4-(1-piperidino)-1-piperidino]carbonyloxy) CPT
(20S)-7-(2-hydroxyethylamino)methyl-10-[4-(1-piperidino)-1-piperidino]carbonyloxy) CPT
(20S)-7-(tris(hydroxymethyl)methylamino)methyl-9-dimethylaminomethyl-10-hydroxy CPT
(20S)-7-(bis(hydroxymethyl)methylamino)methyl-9-dimethylaminomethyl-10-hydroxy CPT
(20S)-7-(2-hydroxyethylamino)methyl-9-dimethylaminomethyl-10-hydroxy CPT
(20S)-7-(tris(hydroxymethyl)methylamino)methyl-9-amino CPT
(20S)-7-(bis(hydroxymethyl)methylamino)methyl-9-amino CPT
(20S)-7-(2-hydroxyethylamino)methyl-9-amino CPT
(20S)-7-(tris(hydroxymethyl)methylamino)methyl-9-nitro CPT
(20S)-7-(bis(hydroxymethyl)methylamino)methyl-9-nitro CPT
(20S)-7-(2-hydroxyethylamino)methyl-9-nitro CPT
(20S)-7-(tris(hydroxymethyl)methylamino)methyl-10-hydroxy CPT
(20S)-7-(bis(hydroxymethyl)methylamino)methyl-10-hydroxy CPT
(20S)-7-(2-hydroxyethylamino)methyl-10-hydroxy CPT; and the like.

Example 3

20-O-[(−)TAPA]-Boc-10H-CPT ester (11)

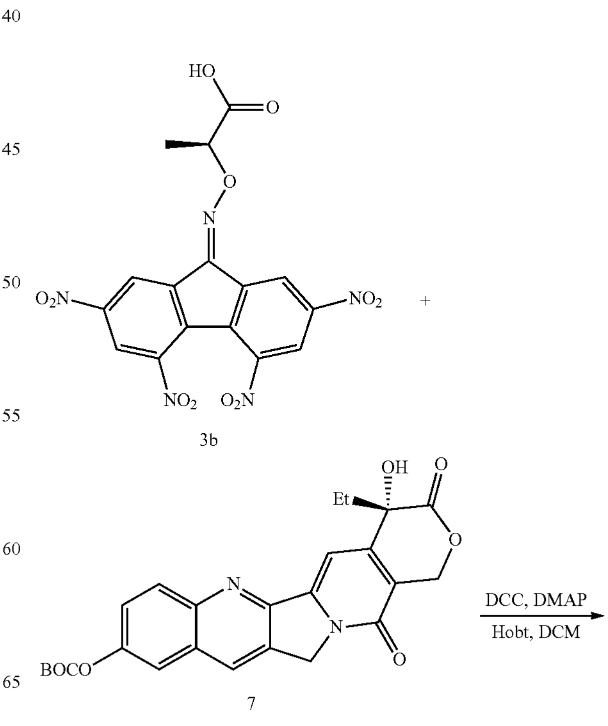

-continued

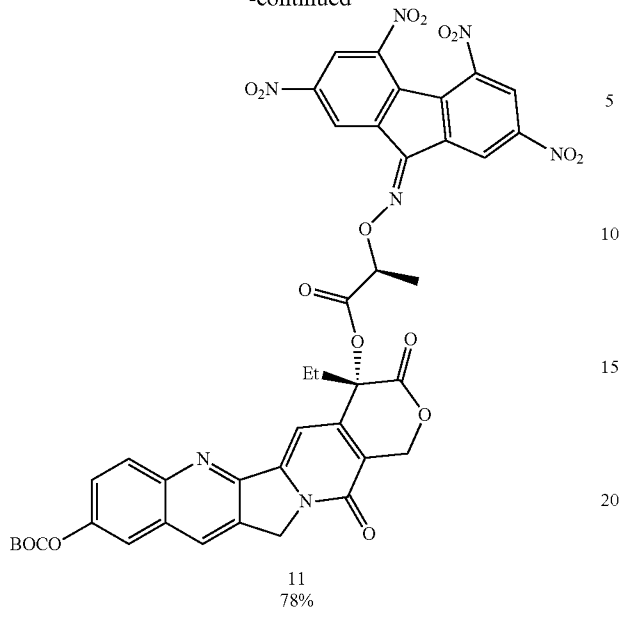

11
78%

-continued

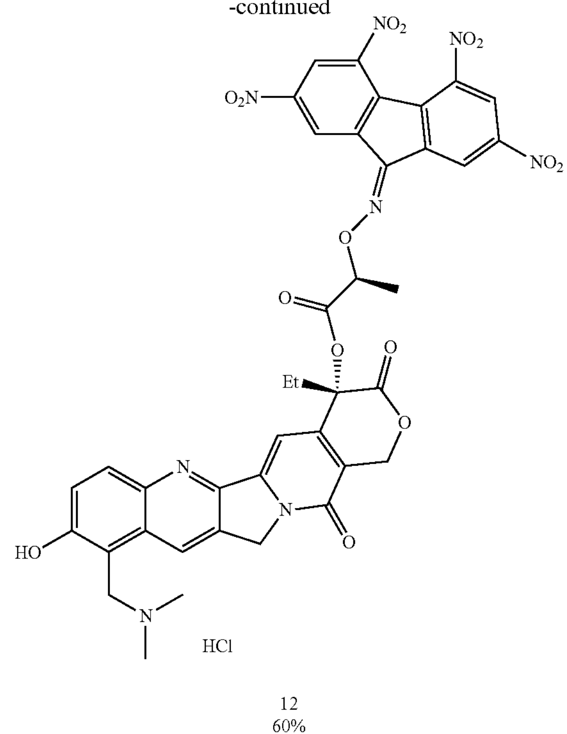

12
60%

To a solution of (−)TAPA 3b (1.44 g, 3.23 mmol), Boc-10H-CPT 7 (1 g, 2.15 mmol), Hobt (320 mg, 2.37 mmol) and DCC (1.33 g, 6.45 mmol) in anhy DCM (40 mL) was added a solution of DMAP (105 mg, 0.86 mmol) in anhy DCM (3 mL). After 1 hr at rt, DCC (1.33 g, 6.45 mmol) and (−)TAPA 3b (400 mg, 0.84 mmol) were added. The reaction was stirred at rt overnight. The mixture was filtered, diluted with DCM (100 mL) and washed with 1N HCl (2×100 mL), saturated aq $NaHCO_3$ solution (2×100 mL), dried over $Na_2SO_4$, treated with activated carbon and filtered. The solvent was evaporated and the remaining residue was purified by silica gel column with 50-80% EtOAc:Hexanes to give 1.47 g of 20-O—[(−)TAPA]-Boc-10H-CPT ester 11 as a yellow solid (78%). $^1$H NMR ($CDCl_3$) δ 9.52 (s, 1H, Ar), 8.99 (s, 1H, Ar), 8.48 (s, 1H, Ar), 8.33 (s, 2H, Ar), 7.83-7.58 (m, 3H), 7.09 (s, 1H), 5.68 (d, 1H, J=17.4 Hz, —C—$CH_2$—O—C(O)—), 5.52-5.42 (m, 2H, —C—$CH_2$—O—C(O)— and O—C(O)—CH(Me)-O—), 5.28 (s, 2H, —C—$CH_2$—N—), 2.55-2.20 (dm, 2H, $CH_2$-Me), 1.96 (d, 3H, J=7.2 Hz, $CH_3$), 1.63 (s, 9H, t-Bu), 0.97 (t, 3H, J=7.2 Hz, $CH_3$); M.p. 210-215° C. (dec); ESIMS: calcd for $C_{41}H_{31}N_7O_{17}[M+H]^+$ 894.18, found 894.3.

Compound 12

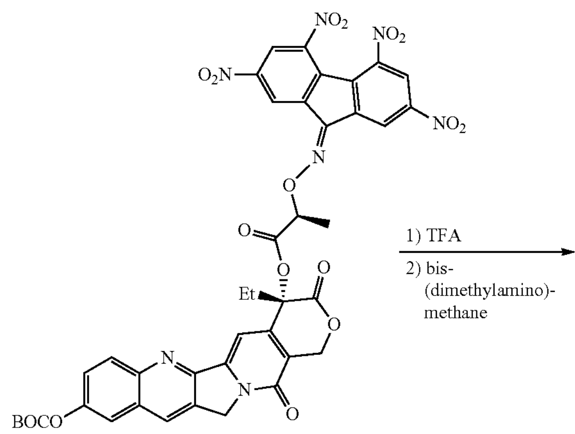

11

The 20-O-[(−)TAPA]-Boc-10H-CPT ester 8 (1.3 g, 1.48 mmol) was dissolved in TFA (15 mL). After stirring at rt for 1 hr, bis-(dimethylamine)-methane (7.5 mL) was added slowly. The mixture was stirred at rt for 45 min and the crude product was precipitated by addition to water. Filtered and the precipitate was dissolved in DCM (75 mL), washed with saturated $NaHCO_3$ solution (2×50 mL, the solution turned red), dried over $Na_2SO_4$, filtered and the solvent was removed. The dark red solid was dissolved in MeOH (20 mL) and added 10 mL of 2M HCl in $Et_2O$. The solvent was evaporated and the residue was purified by silica gel column with 5-20% MeOH:DCM to afford 786 mg of 12 as hydrochloride salt (60%). $^1$H NMR ($CD_3OD$): δ 9.55 (s, 1H, Ar), 9.07 (s, 1H, Ar), 8.77 (s, 1H, Ar), 8.26 (s, 1H, Ar), 8.05 (s, 1H, Ar), 7.67 (d, 1H, J=9.0 Hz, Ar), 7.57-7.52 (m, 2H, Ar), 7.21 (s, 1H), 5.70-5.50 (m, 3H), 5.31 (s, 2H, —C—$CH_2$—N—), 4.60 (m, 2H), 3.07 (s, 6H, —N—$CH_3$), 2.38 (dm, 2H, J=7.2 Hz, —$CH_2$-Me), 1.93 (d, 3H, J=6.6 Hz, $CH_3$), 0.98 (t, 3H, J=7.2 Hz, $CH_3$); ESIMS: calcd for $C_{39}H_{30}N_8O_{15}$ $[M+H]^+$ 851.18, found 851.4.

By substituting other camptothecin analogs for Boc-10H-CPT 7 in step 1 of this example other compounds of this invention are prepared. Other camptothecin analogs include the following:

(20S)-9-nitro CPT;
(20S)-7-chloro-n-propyldimethylsilyl CPT;
(20S)-10-hydroxy-7-chloro-n-propyldimethylsilyl CPT;
(20S)-10-acetoxy-7-chloro-n-propyldimethylsilyl CPT;
(20S)-7-tert-butyldimethylsilyl CPT;
(20S)-10-hydroxy-7-tert-butyldimethylsilyl CPT;
(20S)-10-acetoxy-7-tert-butyldimethylsilyl CPT;
(20S)-9-hydroxy CPT;
(20S)-9-amino CPT;
(20S)-10-amino CPT;
(20S)-9-amino-10-hydroxy CPT;
(20S)-9-methylamino CPT;
(20S)-9-chloro CPT;

(20S)-9-fluoro CPT;
(20S)-9-piperidino CPT;
(20S)-9-morpholinomethyl CPT;
(20S)-9,10-dichloro CPT;
(20S)-10-bromo CPT;
(20S)-10-chloro CPT;
(20S)-10-methyl CPT;
(20S)-10-fluoro CPT;
(20S)-10-nitro CPT;
(20S)-10,11-methylenedioxy CPT;
(20S)-10-formyl CPT;
(20S)-10-nonylcarbonyloxy CPT;
(20S)-10-undecylcarbonyloxy CPT;
(20S)-10-heptadecylcarbonyloxy CPT;
(20S)-10-nonadecylcarbonyloxy CPT;
(20S)-9-nitro-10,11-methylenedioxy CPT;
(20S)-9-(4-methylpiperazinylmethyl)-10-hydroxy (CPT);
(20S)-9-[4-(1-piperidino)-1-piperidinomethyl]-10-hydroxy CPT;
(20S)-9-methyl-10,11-methylenedioxy CPT;
(20S)-9-chloro-10,11-methylenedioxy CPT;
(20S)-9-cyano-10,11-methylenedioxy CPT;
(20S)-9-acetoxy-10,11-methylenedioxy CPT;
(20S)-9-acetylamino-10,11-methylenedioxy CPT;
(20S)-9-aminomethyl-10-hydroxy CPT;
(20S)-9-ethoxymethyl-10-hydroxy CPT;
(20S)-9-methylaminomethyl-10-hydroxy CPT;
(20S)-9-n-propylaminomethyl-10-hydroxy CPT;
(20S)-9-dimethylaminomethyl-10-hydroxy CPT;
(20S)-9-cyclohexylaminomethyl-10-hydroxy CPT;
(20S)-9-(2-hydroxyethylaminomethyl-10-hydroxy CPT;
(20S)-9-(trimethylammonio)methyl-10-hydroxy CPT, methanesulfonate;
(20S)-9-morpholinomethyl-10-hydroxy CPT;
(20S)-5-(2-hydroxyethoxy) CPT
(20S)-9-cyanomethyl-10-hydroxy CPT;
(20S)-CPT-7-aldehyde;
(20S)-10-methoxy CPT-7-aldehyde;
(20S)-7-acetoxymethyl CPT;
(20S)-7-acetoxymethyl-10-methyl CPT;
(20S)-7-cyano-10-methoxy CPT;
(20S)-7-cyano CPT;
(20S)-7-formylethenyl CPT;
(20S)-7-ethoxycarbonylethenyl CPT;
(20S)-7-cyanoethenyl CPT;
(20S)-7-(2,2-dicyanoethenyl) CPT;
(20S)-7-(2-cyano-2-ethoxycarbonyl)ethenyl CPT;
(20S)-7-ethoxycarbonylethyl CPT;
(20S)-7-ethyl CPT;
(20S)-7-n-propyl CPT;
(20S)-7-acetoxymethyl CPT;
(20S)-7-n-propylcarbonyloxymethyl CPT;
(20S)-7-ethoxycarbonyl CPT;
(20S)-7-ethyl-10-hydroxy CPT;
(20S)-7-ethyl-10-acetyloxy CPT;
(20S)-7-methyl-10-aminocarbonyloxy CPT;
(20S)-7-n-propyl-10-piperidinocazbonyloxy CPT;
(20S)-7-ethyl-10-(2-dimethylamino)ethyl CPT; and
(20S)-7-ethyl-10-carbamoyloxy derivatives of CPT such as
(20S)-7-ethyl-10-[4(1-piperidino)-piperidino]carbonyloxy CPT;
(20S)-7-ethyl-10-(1-piperazine)carbonyloxy CPT;
(20S)-7-ethyl-10-(4-i-propylaminocarbonylmethylpiperazine)carbonyloxy CPT;
(20S)-7-ethyl-10-[4(1-pyrrolidinyl)piperazine]carbonyloxy CPT;
(20S)-7-ethyl-10-[(4-(dimethylamino)-1-piperidino]carbonyloxy CPT;
(20S)-7-ethyl-10-[4-(di-n-propylamino)-1-piperidinol]carbonyloxy CPT;
(20S)-7-ethyl-10-[(4-(di-n-butylamino)-1-piperidino]carbonyloxy CPT;
(20S)-7-ethyl-10-[4-(1-pyrrolidino)-1-piperidino)]carbonyloxy CPT;
(20S)-7-ethyl-10-[4-(1-piperidino)-1-piperidino]carbonyloxy CPT;
(20S)-7-ethyl-10-[N-methyl-N-2-(dimethylamino)ethylamino]carbonyloxy CPT
(20S)-7-(tert-butyldimethylsilyl) CPT
(20S)-7-(tert-butoxyiminomethyl) CPT (Gimatecan)
(20S)-7-butyl-10,11-methylenedioxy CPT
(20S)-7-bromomethyl-10-hydroxy CPT
(20S)-7-butyl-10-amino CPT
(20S)-7-(tert-butyldimethylsilyl)-10-hydroxy CPT
(20S)-7-[(2-trimethylsilyl)ethyl)] CPT (Karenitican)
(20S)-7-[(4-fluorophenoxy)acetyloxymethyl] CPT
(20S)-7-[(4-methoxyphenoxy)acetyloxymethyl] CPT
(20S)-7-[(4-cyano-3-fluorophenoxy)acetyloxymethyl] CPT
(20S)-7-[(3,4,5-trimethoxyphenyl)acetyloxymethyl] CPT
(20S)-10-[(4-cyano-3-fluorophenoxy)acetyloxy] CPT
(20S)-10-[(3,4,5-trimethoxyphenyl)acetyloxy] CPT
(20S)-7-(4-methylpiperazinomethylene)-10,11-ethylenedioxy CPT (Exatecan)
(20S)-7-[2-(N-isopropylamino)ethyl] CPT (Belotecan)
(20S)-[5(RS)-(2-hydroxyethoxy)] CPT
(20S)-7-ethyl-9-allyl-10-hydroxy CPT (29)
(20S)-7-ethyl-9-allyl-10-methoxy CPT (29)
(20S)-7-ethyl-9-propyl-10-hydroxy CPT (29)
(20S)-7-ethyl-9-propyl-10-methoxy CPT (29)
(20S)-7,9-diethyl-10-hydroxy CPT (29)
(20S)-7,9-diethyl-10-methoxy CPT (29)
(20S)-10-(substituted quaternary ammonium salts) CPT
(20S)-7-(tris(hydroxymethyl)methylamino)methyl CPT
(20S)-7-(bis(hydroxymethyl)methylamino)methyl CPT
(20S)-7-(2-hydroxyethylamino)methyl CPT
(20S)-7-(tris(hydroxymethyl)methylamino)methyl-10,11-methylenedioxy CPT
(20S)-7-(bis(hydroxymethyl)methylamino)methyl-10,11-methylenedioxy CPT
(20S)-7-(2-hydroxyethylamino)methyl-10,11-methylenedioxy CPT
(20S)-7-(tris(hydroxymethyl)methylamino)methyl-10-[4-(1-piperidino)-1-piperidino]carbonyloxy) CPT
(20S)-7-(bis(hydroxymethyl)methylamino)methyl-10-[4-(1-piperidino)-1-piperidino]carbonyloxy) CPT
(20S)-7-(2-hydroxyethylamino)methyl-10-[4-(1-piperidino)-1-piperidino]carbonyloxy) CPT
(20S)-7-(tris(hydroxymethyl)methylamino)methyl-9-dimethylaminomethyl-10-hydroxy CPT
(20S)-7-(bis(hydroxymethyl)methylamino)methyl-9-dimethylaminomethyl-10-hydroxy CPT
(20S)-7-(2-hydroxyethylamino)methyl-9-dimethylaminomethyl-10-hydroxy CPT
(20S)-7-(tris(hydroxymethyl)methylamino)methyl-9-amino CPT
(20S)-7-(bis(hydroxymethyl)methylamino)methyl-9-amino CPT
(20S)-7-(2-hydroxyethylamino)methyl-9-amino CPT
(20S)-7-(tris(hydroxymethyl)methylamino)methyl-9-nitro CPT
(20S)-7-(bis(hydroxymethyl)methylamino)methyl-9-nitro CPT
(20S)-7-(2-hydroxyethylamino)methyl-9-nitro CPT (20S)-7-(tris(hydroxymethyl)methylamino)methyl-10-hydroxy CPT (20S)-7-(bis(hydroxymethyl)methylamino)methyl-10-hydroxy CPT (20S)-7-(2-hydroxyethylamino)methyl-10-hydroxy CPT; and the like.

Example 4

Compound 13

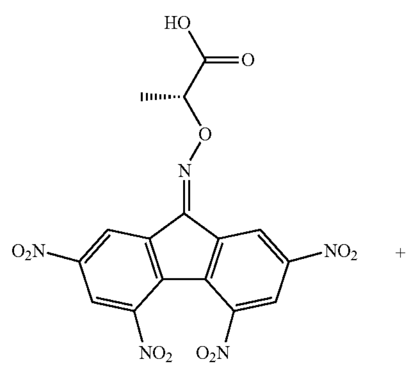

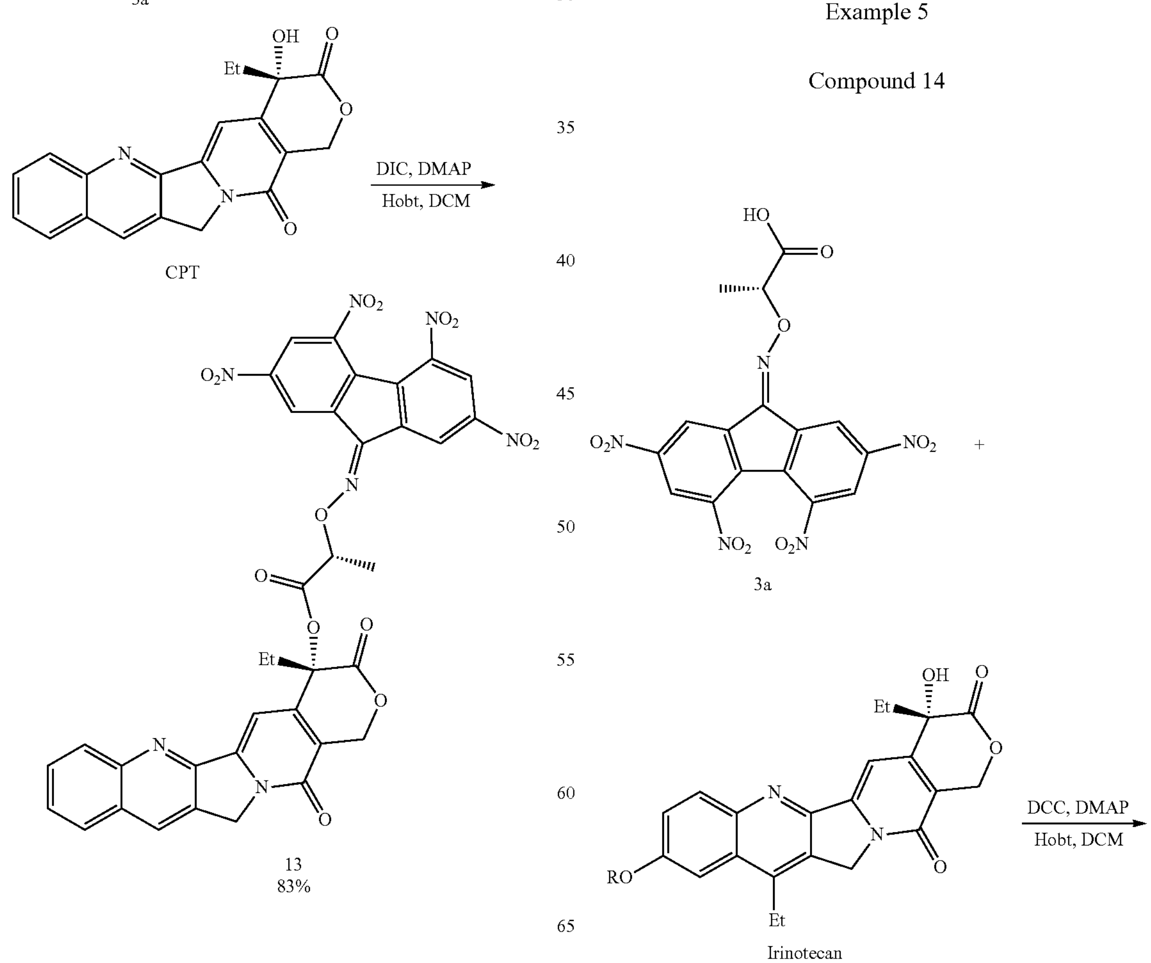

To a solution of (+)TAPA 3a (1.9 g 4.31 mmol), camptothecin (1.0 g, 2.87 mmol), Hobt (426 mg, 3.16 mmol) and DIC (0.89 mL, 5.74 mmol) in anhy DCM (52 mL) was added a solution of DMAP (140 mg, 1.15 mmol) in anhy DCM (5 mL). After 1 hr at rt, DIC (0.89 mL, 5.74 mmol) and (+)-TAPA 3a (0.67 g, 1.43 mmol) were added. The reaction was stirred at rt overnight. The mixture was diluted with DCM (300 mL) and washed with 1N HCl (2×150 mL), saturated aq $NaHCO_3$ solution (2×150 mL), dried over $Na_2SO_4$, treated with activated carbon and filtered. The solvent was evaporated and the remaining residue was purified by silica gel column with 50-80% EtOAc:Hexanes to give 1.85 g of 13 as a yellow solid (83%). $^1$H ($CDCl_3$): δ 9.44 (s, 1H, tetranitrofluorenone), 8.80 (s, 1H, tetranitrofluorenone), 8.52 (s, 1H, tetranitrofluorenone), 8.33 (s, 2H, Ar), 7.91 (d, 1H, J=7.7 Hz, Ar), 7.8-7.65 (m, 2H, Ar), 7.43 (m, 1H, Ar), 7.17 (s, 1H), 5.72 (d, 1H, J=17.7 Hz, —C—$CH_2$—O—C(O)—), 5.55-5.44 (m, 2H, —C—$CH_2$—O—C(O)— and O—C(O)—CH(Me)-O—), 5.28 (s, 2H, —C—$CH_2$—N—), 2.35 (dm, 2H, J=7.2 Hz, $CH_2$-Me), 1.83 (d, 3H, J=7.2 Hz, —CH($CH_3$)), 0.97 (t, 3H, J=7.2 Hz, $CH_3$); $^{13}$C NMR ($CDCl_3$): δ 168.98, 166.94, 157.36, 152.05, 148.97, 148.39, 148.14, 147.47, 146.43, 146.34, 144.80, 140.75, 133.99, 133.58, 132.19, 131.64, 131.19, 129.02, 128.80, 128.48, 128.16, 127.19, 122.43, 121.18, 121.12, 120.53, 96.15, 81.11, 67.67, 53.80, 50.43, 32.39, 17.24, 7.91; M.p. 210-213° C. (dec), ESIMS: calcd for $C_{36}H_{23}N_7O_{14}$ $[M+H]^+$ 778.13, found 778.0.

Example 5

Compound 14

-continued

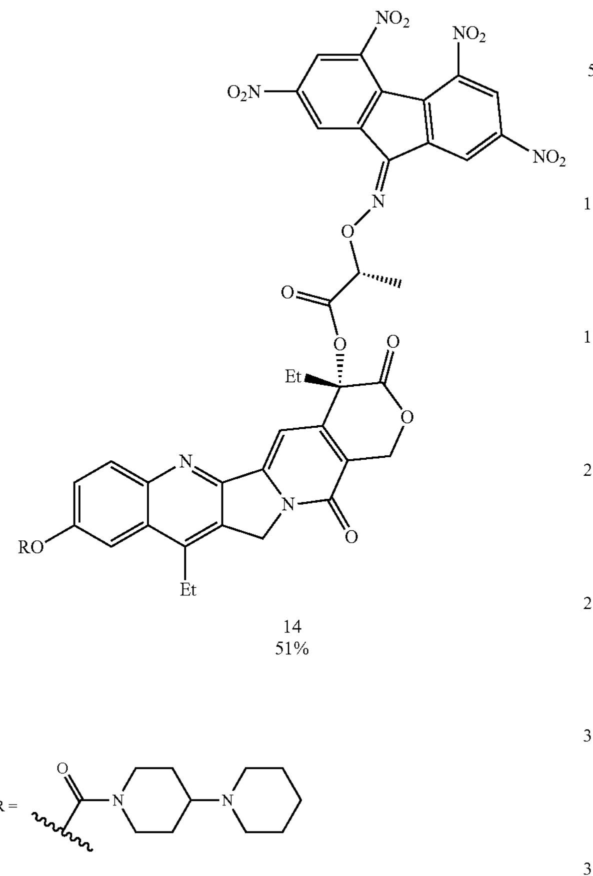

14
51%

To a solution of (+)TAPA 3a (1.43 g, 3.19 mmol), irinotecan (1.25 g, 2.13 mmol), Hobt (316 mg, 2.34 mmol) and DCC (1.33 g, 6.38 mmol) in anhy DCM (30 mL) was added a solution of DMAP (78 mg, 0.64 mmol) in anhy DCM (12 mL). After 1 hr at rt, DCC (1.33 g, 6.38 mmol) was added. The reaction was stirred at rt overnight. The mixture was filtered, diluted with DCM (25 mL) and washed with 1N HCl (2×25 mL), saturated aq $NaHCO_3$ solution (2×25 mL), dried over $Na_2SO_4$, treated with activated carbon and filtered. The solvent was evaporated and the remaining residue was purified by silica gel column with 5-10% MeOH:DCM and concentrated. Added 2N HCl in $Et_2O$ (10 mL) and the mixture was decanted into 1:1 EtOAc:$Et_2O$ (50 mL), filtered and dried to give 1.15 g of 14 as hydrochloride salt (51%). $^1H$ NMR ($CDCl_3$): δ 9.43 (s, 1H, tetranitrofluorenone), 8.79 (s, 1H, tetranitrofluorenone), 8.49 (s, 1H, tetranitrofluorenone), 8.36 (s, 2H, Ar), 7.81 (s, 1H, Ar), 7.66 (d, 1H, J=9.3 Hz, Ar), 7.49 (s, 1H, J=9.3 Hz, Ar), 7.08 (s, 1H), 5.71 (d, 1H, 17.4 Hz, —C—$CH_2$—O—C(O)—), 5.53-5.43 (m, 2H, —C—$CH_2$—O—C(O)— and O—C(O)—CH(Me)-O—), 5.24 (s, 2H, —C—$CH_2$—N—), 4.48 (d, 2H, J=12.3 Hz), 4.36 (d, 2H, J=12.3 Hz), 3.20-2.50 (m, 7H), 2.60 (dm, 2H, J=7.8 Hz, $CH_2$), 2.15-1.50 (m, 12H), 1.40 (t, 3H, J=7.5 Hz, $CH_3$), 0.95 (t, 3H, J=7.5 Hz, $CH_3$); M.p. 210-215 (dec); ESIMS: calcd for $C_{49}H_{45}N_9O_{16}$ $[M+H]^+$ 1016.30, found 1016.5.

Example 6

Compound 15

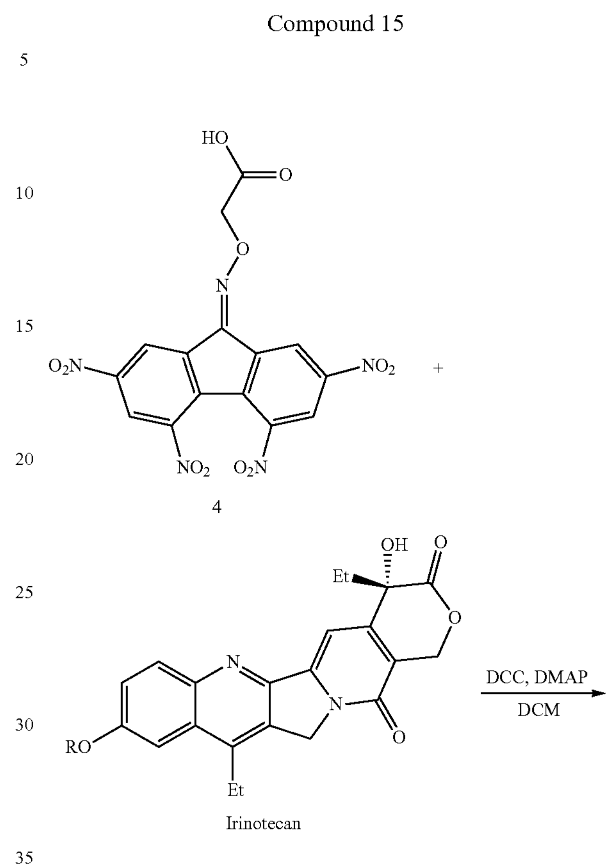

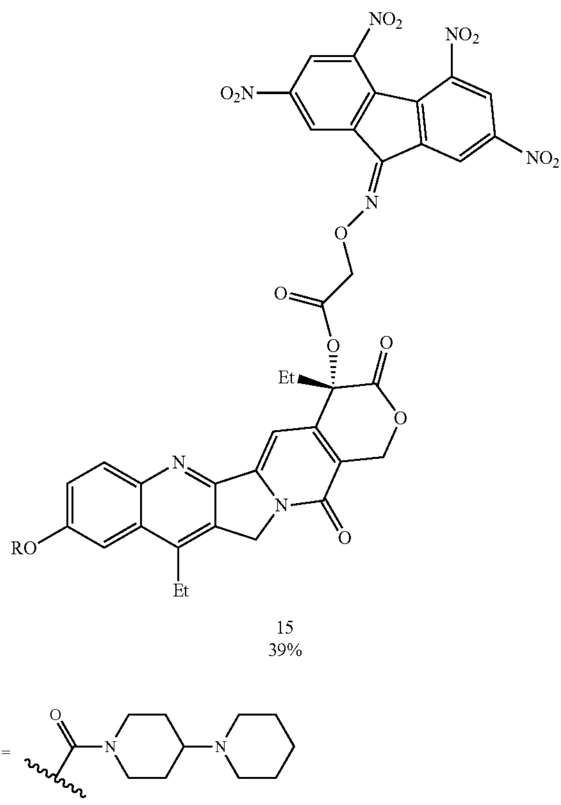

15
39%

To a solution of TNF-ethanoic acid 4 (1.43 g, 3.19 mmol), irinotecan (1.25 g, 2.13 mmol), Hobt (316 mg, 2.34 mmol) and DCC (1.33 g, 6.38 mmol) in anhy DCM (30 mL) was added a solution of DMAP (78 mg, 0.64 mmol) in anhy DCM (12 mL). After 1 hr at rt, DCC (1.33 g, 6.38 mmol) was added. The reaction was stirred at rt overnight. The mixture was filtered and diluted with DCM (25 mL) and washed with 1N HCl (2×25 mL), saturated aq $NaHCO_3$ solution (2×25 mL), dried over $Na_2SO_4$, treated with activated carbon and filtered. The solvent was evaporated and the remaining residue was purified by silica gel column with 5-10% MeOH:DCM and concentrated. Added 2N HCl in $Et_2O$ (10 mL) and the mixture was decanted into 1:1 EtOAc:$Et_2O$ (50 mL), filtered and dried to give 1.15 g of 15 as hydrochloride salt, yellow in color (51%). $^1$NMR ($CDCl_3$): δ 9.46 (s, 1H, tetranitrofluorenone), 8.89 (s, 1H, tetranitrofluorenone), 8.61 (s, 1H, tetranitrofluorenone), 8.53 (s, 1H, tetranitrofluorenone), 7.85-7.77 (m, 2H, Ar), 7.48 (d, 1H, Ar), 7.14 (s, 1H), 5.62-5.32 (m, 4H, —C—$CH_2$—O—C(O)— and O—C(O)—$CH_2$—O—N—), 5.23 (s, 2H, —C—$CH_2$—N—), 4.48 (d, 2H, J=12.3 Hz), 4.36 (d, 2H, J=12.3 Hz), 3.60-2.80 (m, 7H), 2.60-2.20 (m, 4H), 2.18-1.80 (m, 8H), 1.36 (t, 3H, J=7.5 Hz, $CH_3$), 0.98 (t, 3H, J=7.5 Hz, $CH_3$); M.p. 210-215 (dec); ESIMS: calcd for $C_{48}H_{43}N_9O_{16}$ [M+H]+ 1002.28, found 1002.5.

-continued

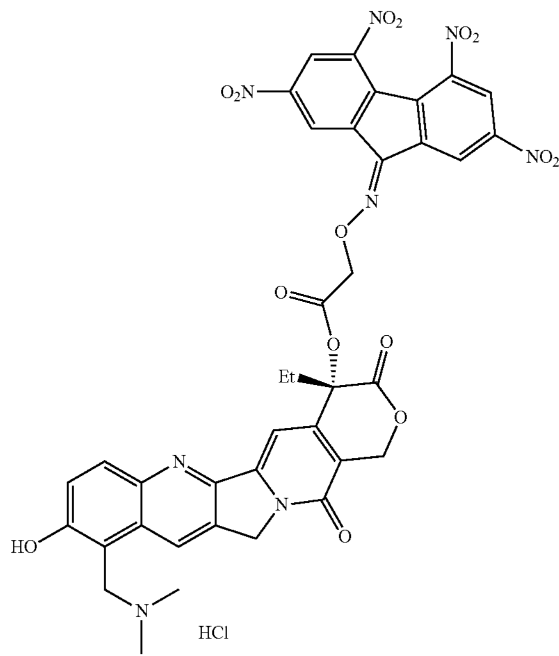

16
63%

Example 7

Compound 16

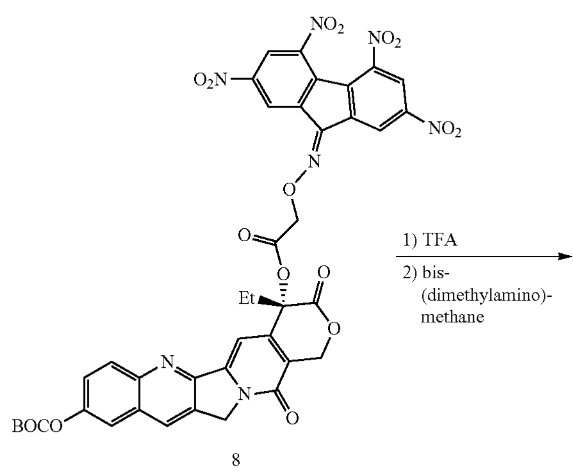

8

The 20-O-(TNF-ethanoyl)-Boc-10H-CPT ester 8 (5.3 g, 6.02 mmol) was dissolved in TFA (60 mL). After stirring at rt for 1 hr, bis-(dimethylamine)-methane (30 mL) was added slowly. The mixture was stirred at rt for 45 min and the crude product was precipitated by addition to water. Filtered and the precipitate was dissolved in DCM (300 mL), washed with saturated $NaHCO_3$ solution (3×200 mL, the solution turned red), dried over $Na_2SO_4$, filtered and the solvent was removed. The dark red solid was dissolved in MeOH (100 mL) and added 30 mL of 2M HCl in $Et_2O$. The solvent was evaporated and the residue was purified by silica gel column with 5-20% MeOH:DCM to afford 3.32 g of 16 as hydrochloride salt (63%). $^1$H NMR (1:1 $CDCl_3$:$CD_3OD$): δ 9.47 (s, 1H, tetranitrofluorenone), 8.94 (s, 2H, tetranitrofluorenone and Ar), 8.70 (s, 1H, tetranitrofluorenone), 8.63 (s, 1H, tetranitrofluorenone), 8.04 (d, 1H, J=9.3 Hz, Ar), 7.59 (d, 1H, J=9.3 Hz, Ar), 7.36 (s, 1H), 5.66 (d, 1H, J=17.1 Hz, —C—$CH_2$—O—C(O)—), 5.55-5.40 (m, 3H, —C—$CH_2$—O—C(O)— and O—C(O)—$CH_2$—O—N—), 5.37 (s, 2H, —C—$CH_2$—N—), 4.81 (s, 2H, —$CH_2$—N(Me)$_2$), 2.99 (s, 3H, N($CH_3$)$_2$), 2.95 (s, 3H, N($CH_3$)$_2$), 2.50 (dm, 2H, J=6.9 Hz, $CH_2$-Me), 1.03 (t, 3H, J=6.9 Hz, $CH_3$); M.p. 210-215° C. (dec); ESIMS: calcd for $C_{38}H_{28}N_8O_{15}$ [M+H]$^+$ 837.17, found 837.4.

Example 8

Compound 17

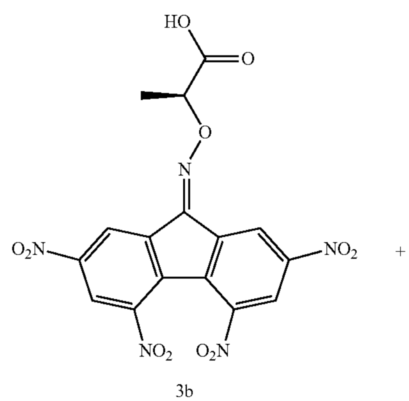

To a solution of (−)TAPA 3b (960 mg 2.15 mmol), camptothecin (0.5 g, 1.44 mmol), Hobt (213 mg, 1.44 mmol) and DCC (0.89 g, 4.3 mmol) in anhy DCM (25 mL) was added a solution of DMAP (70 mg, 0.57 mmol) in anhy DCM (3 mL). After 1 hr at rt, DCC (0.89 g, 4.3 mmol) and (−)TAPA 3b (320 mg, 0.72 mmol) were added. The reaction was stirred at rt overnight. The mixture was filtered, diluted with DCM (75 mL) and washed with 1N HCl (2×100 mL), saturated aq $NaHCO_3$ solution (2×100 mL), dried over $Na_2SO_4$, treated with activated carbon and filtered. The solvent was evaporated and the remaining residue was purified by silica gel column with 50-80% EtOAc:Hexanes to give 0.97 g of 17 as yellow solid (87%). $^1$H NMR ($CDCl_3$): δ 9.54 (s, 1H, tetranitrofluorenone), 9.01 (s, 1H, tetranitrofluorenone), 8.43 (s, 1H, tetranitrofluorenone), 8.33 (s, 2H, Ar), 7.92 (d, 1H, J=7.8 Hz, Ar), 7.80-7.63 (m, 3H, Ar), 7.08 (s, 1H), 5.72 (d, 1H, J=17.7 Hz, —C—$CH_2$—O—C(O)—), 5.56-5.44 (m, 2H, —C—$CH_2$—O—C(O)— and O—C(O)—CH(Me)-O—), 5.29 (s, 2H, —C—$CH_2$—N—), 2.35 (dm, 2H, J=7.2 Hz, $CH_2$-Me), 1.97 (d, 3H, J=6.9 Hz, —CH($CH_3$)), 0.99 (t, 3H, J=7.2 Hz, $CH_3$); ESIMS: calcd for $C_{36}H_{23}N_7O_{14}$ $[M+H]^+$ 778.13, found 778.0.

Example 9

Compound 18

-continued

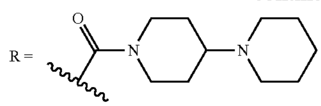

To a solution of (−)TAPA 3b (230 mg, 0.51 mmol), irinotecan (200 mg, 0.34 mmol), Hobt (51 mg, 0.38 mmol) and DIC (160 μL, 1.02 mmol) in anhy DCM (6 mL) was added a solution of DMAP (16 mg, 0.14 mmol) in anhy DCM (1 mL). After 1 hr at rt, DIC (160 μL, 1.02 mmol) and (−)TAPA (75 mg, 0.17 mmol) were added. The reaction was stirred at rt overnight. The mixture was diluted with DCM (50 mL) and washed with 1N HCl (2×25 mL), saturated aq $NaHCO_3$ solution (2×25 mL), dried over $Na_2SO_4$, treated with activated carbon and filtered. The solvent was evaporated and the remaining residue was purified by silica gel column with 5-10% MeOH:DCM and concentrated. Added 2N HCl in $Et_2O$ (5 mL) and the mixture was decanted into 1:1 EtOAc: $Et_2O$ (50 mL), filtered and dried to give 255 mg of 18 as hydrochloride salt (71%). $^1H$ NMR ($CDCl_3$): δ 9.52 (s, 1H, tetranitrofluorenone), 8.99 (s, 1H, tetranitrofluorenone), 8.36 (s, 1H, Ar), 8.20 (s, 1H, Ar), 8.00 (s, 1H, Ar), 7.81-7.45 (m, 3H, Ar), 7.01 (s, 1H), 5.71 (d, 1H, 17.4 Hz, —C—$CH_2$—O—C(O)—), 5.53-5.43 (m, 2H, —C—$CH_2$—O—C(O)— and O—C(O)—CH(Me)-O—), 5.24 (s, 2H, —C—$CH_2$—N—), 4.48 (d, 2H, J=12.3 Hz), 4.36 (d, 2H, J=12.3 Hz), 3.20-2.50 (m, 7H), 2.60 (dm, 2H, J=7.8 Hz, $CH_2$), 2.15-1.50 (m, 12H), 1.40 (t, 3H, J=7.5 Hz, $CH_3$), 0.95 (t, 3H, J=7.5 Hz, $CH_3$); ESIMS: calcd for $C_{49}H_{45}N_9O_{16}$ $[M+H]^+$ 1016.30, found 1016.5.

Example 10

Compound 19

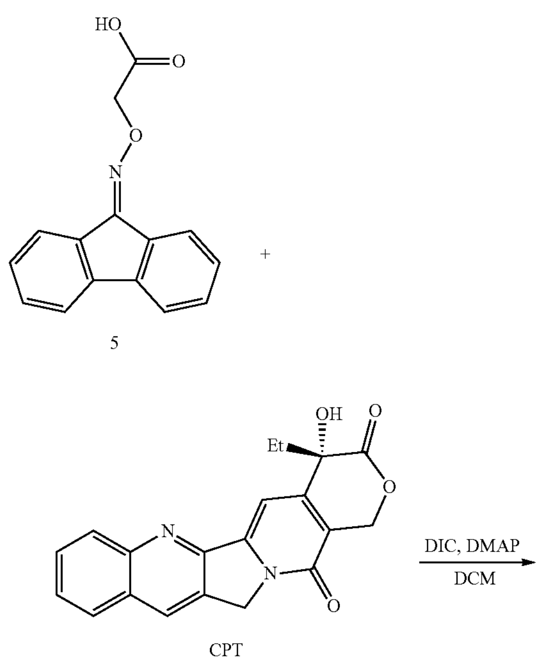

-continued

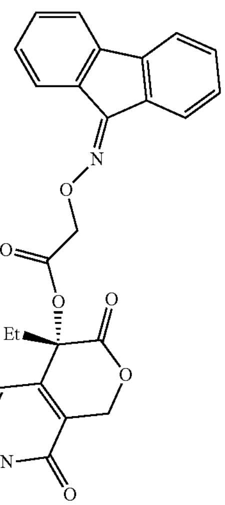

19
32%

To a solution of 9F-ethanoic acid 5 (146 mg 0.57 mmol), camptothecin (100 mg, 0.29 mmol) and DIC (133 μL, 0.86 mmol) in anhy DCM (6 mL) was added DMAP (14 mg, 0.11 mmol). After 22 hr at rt, DIC (133 μL, 0.86 mmol) and 9F-ethanoic acid 9 (70 mg, 0.29 mmol) were added. The reaction was stirred at rt overnight, diluted with DCM (50 mL) and washed with 1N HCl (2×25 mL), saturated aq $NaHCO_3$ solution (2×25 mL), dried over $Na_2SO_4$ and filtered. The solvent was evaporated and the remaining residue was purified by silica gel column with 30-100% EtOAc:Hexanes to give 53 mg of 19 as light yellow solid (32%). $^1H$ NMR (1:5 acetone-d6:$CDCl_3$): δ 8.32 (s, 1H, Ar), 8.23 (d, 1H, J=7.5 Hz, Ar), 8.16 (d, 1H, J=8.4 Hz, Ar), 7.92-7.60 (m, 4H, Ar), 7.47 (d, 1H, J=7.8 Hz, Ar), 7.38-7.20 (m, 4H, Ar, ═CH—), 7.08 (t, 1H, J=7.8 Hz, Ar), 6.65 (t, 1H, J=7.5 Hz, Ar), 5.61 (d, 1H, J=17.4 Hz, —C—$CH_2$—O—C(O)—), 5.31 (d, 1H, J=17.4 Hz, —C—$CH_2$—O—C(O)—), 5.18 (s, 2H, —C—$CH_2$—N—), 5.05 (dd, 2H, J=16.5 Hz, 24.9 Hz, O—C(O)—$CH_2$—O—), 2.09 (m, 2H, J=8.4 Hz, $CH_2$-Me), 0.88 (t, 3H, 0.1=8.4 Hz, $CH_3$); ESIMS: calcd for $C_{33}H_{25}N_3O_6$ $[M+H]^+$ 584.17, found 584.3, 1167.7 (dimer).

By substituting other camptothecin analogs CPT in this example other compounds of this invention are prepared. Other camptothecin analogs include the following:

(20S)-7-ethyl-10-[4-(1-piperidino)-1-piperidino]carbonyloxy)-CPT (AKA-irinotecan);
(20S)-9-nitro CPT;
(20S)-7-chloro-n-propyldimethylsilyl CPT;
(20S)-10-hydroxy-7-chloro-n-propyldimethylsilyl CPT;
(20S)-10-acetoxy-7-chloro-n-propyldimethylsilyl CPT;
(20S)-7-tert-butyldimethylsilyl CPT;
(20S)-10-hydroxy-7-tert-butyldimethylsilyl CPT;
(20S)-10-acetoxy-7-tert-butyldimethylsilyl CPT;
(20S)-9-hydroxy CPT;
(20S)-9-amino CPT;
(20S)-10-amino CPT;
(20S)-9-amino-10-hydroxy CPT;
(20S)-9-methylamino CPT;
(20S)-9-chloro CPT;
(20S)-9-fluoro CPT;
(20S)-9-piperidino CPT;
(20S)-9-dimethylaminomethyl-10-hydroxy CPT (3)-AKA topotecan);

(20S)-9-morpholinomethyl CPT;
(20S)-9,10-dichloro CPT;
(20S)-10-bromo CPT;
(20S)-10-chloro CPT;
(20S)-10-methyl CPT;
(20S)-10-fluoro CPT;
(20S)-10-nitro CPT;
(20S)-10,11-methylenedioxy CPT;
(20S)-10-formyl CPT;
(20S)-10-nonylcarbonyloxy CPT;
(20S)-10-undecylcarbonyloxy CPT;
(20S)-10-heptadecylcarbonyloxy CPT;
(20S)-10-nonadecylcarbonyloxy CPT;
(20S)-9-nitro-10,11-methylenedioxy CPT;
(20S)-9-(4-methylpiperazinylmethyl)-10-hydroxy (CPT);
(20S)-9-[4-(1-piperidino)-1-piperidinomethyl]-10-hydroxy CPT;
(20S)-9-methyl-10,11-methylenedioxy CPT;
(20S)-9-chloro-10,11-methylenedioxy CPT;
(20S)-9-cyano-10,11-methylenedioxy CPT;
(20S)-9-acetoxy-10,11-methylenedioxy CPT;
(20S)-9-acetylamino-10,11-methylenedioxy CPT;
(20S)-9-aminomethyl-10-hydroxy CPT;
(20S)-9-ethoxymethyl-10-hydroxy CPT;
(20S)-9-methylaminomethyl-10-hydroxy CPT;
(20S)-9-n-propylaminomethyl-10-hydroxy CPT;
(20S)-9-dimethylaminomethyl-10-hydroxy CPT;
(20S)-9-cyclohexylaminomethyl-10-hydroxy CPT;
(20S)-9-(2-hydroxyethyl)aminomethyl-10-hydroxy CPT;
(20S)-9-(trimethylammonio)methyl-10-hydroxy CPT, methanesulfonate;
(20S)-9-morpholinomethyl-10-hydroxy CPT;
(20S)-5-(2-hydroxyethoxy) CPT
(20S)-9-cyanomethyl-10-hydroxy CPT;
(20S)-CPT-7-aldehyde;
(20S)-10-methoxy CPT-7-aldehyde;
(20S)-7-acetoxymethyl CPT;
(20S)-7-acetoxymethyl-10-methyl CPT;
(20S)-7-cyano-10-methoxy CPT;
(20S)-7-cyano CPT;
(20S)-7-formylethenyl CPT;
(20S)-7-ethoxycarbonylethenyl CPT;
(20S)-7-cyanoethenyl CPT;
(20S)-7-(2,2-dicyanoethenyl) CPT;
(20S)-7-(2-cyano-2-ethoxycarbonyl)ethenyl CPT;
(20S)-7-ethoxycarbonyl ethyl CPT;
(20S)-7-ethyl CPT;
(20S)-7-n-propyl CPT;
(20S)-7-acetoxymethyl CPT;
(20S)-7-n-propylcarbonyloxymethyl CPT;
(20S)-7-ethoxycarbonyl CPT;
(20S)-7-ethyl-10-hydroxy CPT;
(20S)-7-ethyl-10-acetyloxy CPT;
(20S)-7-methyl-10-aminocarbonyloxy CPT;
(20S)-7-n-propyl-10-piperidinocazbonyloxy CPT;
(20S)-7-ethyl-10-(2-dimethylamino)ethyl CPT; and
(20S)-7-ethyl-10-carbamoyloxy derivatives of CPT such as
(20S)-7-ethyl-10-[4(1-piperidino)-piperidino]carbonyloxy CPT;
(20S)-7-ethyl-10-(1-piperazine)carbonyloxy CPT;
(20S)-7-ethyl-10-(4-i-propylaminocarbonylmethylpiperazine)carbonyloxy CPT;
(20S)-7-ethyl-10-[4(1-pyrrolidinyl)piperazine]carbonyloxy CPT;
(20S)-7-ethyl-10-[(4-(dimethylamino)-1-piperidino]carbonyloxy CPT;
(20S)-7-ethyl-10-[4-(di-n-propylamino)-1-piperidinol]carbonyloxy CPT;
(20S)-7-ethyl-10-[(4-(di-n-butylamino)-1-piperidino]carbonyloxy CPT;
(20S)-7-ethyl-10-[4-(1-pyrrolidino)-1-piperidino)]carbonyloxy CPT;
(20S)-7-ethyl-10-[4-(1-piperidino)-1-piperidino]carbonyloxy CPT;
(20S)-7-ethyl-10-[N-methyl-N-2-(dimethylamino)ethylamino]carbonyloxy CPT
(20S)-7-(tert-butyldimethylsilyl) CPT
(20S)-7-(tert-butoxyiminomethyl) CPT (Gimatecan)
(20S)-7-butyl-10,11-methylenedioxy CPT
(20S)-7-bromomethyl-10-hydroxy CPT
(20S)-7-butyl-10-amino CPT
(20S)-7-(tert-butyldimethylsilyl)-10-hydroxy CPT
(20S)-7-[(2-trimethylsilyl)ethyl)] CPT (Karentican)
(20S)-7-[(4-fluorophenoxy)acetyloxymethyl] CPT
(20S)-7-[(4-methoxyphenoxy)acetyloxymethyl] CPT
(20S)-7-[(4-cyano-3-fluorophenoxy)acetyloxymethyl] CPT
(20S)-7-[(3,4,5-trimethoxyphenyl)acetyloxymethyl] CPT
(20S)-10-[(4-cyano-3-fluorophenoxy)acetyloxy] CPT
(20S)-10-[(3,4,5-trimethoxyphenyl)acetyloxy] CPT
(20S)-7-(4-methylpiperazinomethylene)-10,11-ethylenedioxy CPT (Exatecan)
(20S)-7-[2-(N-isopropylamino)ethyl] CPT (Belotecan)
(20S)-[5(RS)-(2-hydroxyethoxy)] CPT
(20S)-7-ethyl-9-allyl-10-hydroxy CPT (29)
(20S)-7-ethyl-9-allyl-10-methoxy CPT (29)
(20S)-7-ethyl-9-propyl-10-hydroxy CPT (29)
(20S)-7-ethyl-9-propyl-10-methoxy CPT (29)
(20S)-7,9-diethyl-10-hydroxy CPT (29)
(20S)-7,9-diethyl-10-methoxy CPT (29)
(20S)-10-(substituted quaternary ammonium salts) CPT
(20S)-7-(tris(hydroxymethyl)methylamino)methyl CPT
(20S)-7-(bis(hydroxymethyl)methylamino)methyl CPT
(20S)-7-(2-hydroxyethylamino)methyl CPT
(20S)-7-(tris(hydroxymethyl)methylamino)methyl-10,11-methylenedioxy CPT
(20S)-7-(bis(hydroxymethyl)methylamino)methyl-10,11-methylenedioxy CPT
(20S)-7-(2-hydroxyethylamino)methyl-10,11-methylenedioxy CPT
(20S)-7-(tris(hydroxymethyl)methylamino)methyl-10-[4-(1-piperidino)-1-piperidino]carbonyloxy) CPT
(20S)-7-(bis(hydroxymethyl)methylamino)methyl-10-[4-(1-piperidino)-1-piperidino]carbonyloxy) CPT
(20S)-7-(2-hydroxyethylamino)methyl-10-[4-(1-piperidino)-1-piperidino]carbonyloxy) CPT
(20S)-7-(tris(hydroxymethyl)methylamino)methyl-9-dimethylaminomethyl-10-hydroxy CPT
(20S)-7-(bis(hydroxymethyl)methylamino)methyl-9-dimethylaminomethyl-10-hydroxy CPT
(20S)-7-(2-hydroxyethylamino)methyl-9-dimethylaminomethyl-10-hydroxy CPT
(20S)-7-(tris(hydroxymethyl)methylamino)methyl-9-amino CPT
(20S)-7-(bis(hydroxymethyl)methylamino)methyl-9-amino CPT
(20S)-7-(2-hydroxyethylamino)methyl-9-amino CPT
(20S)-7-(tris(hydroxymethyl)methylamino)methyl-9-nitro CPT
(20S)-7-(bis(hydroxymethyl)methylamino)methyl-9-nitro CPT
(20S)-7-(2-hydroxyethylamino)methyl-9-nitro CPT
(20S)-7-(tris(hydroxymethyl)methylamino)methyl-10-hydroxy CPT (20S)-7-(bis(hydroxymethyl)methylamino)methyl-10-hydroxy CPT (20S)-7-(2-hydroxyethylamino)methyl-10-hydroxy CPT; and the like.

Example 11

Compound 20

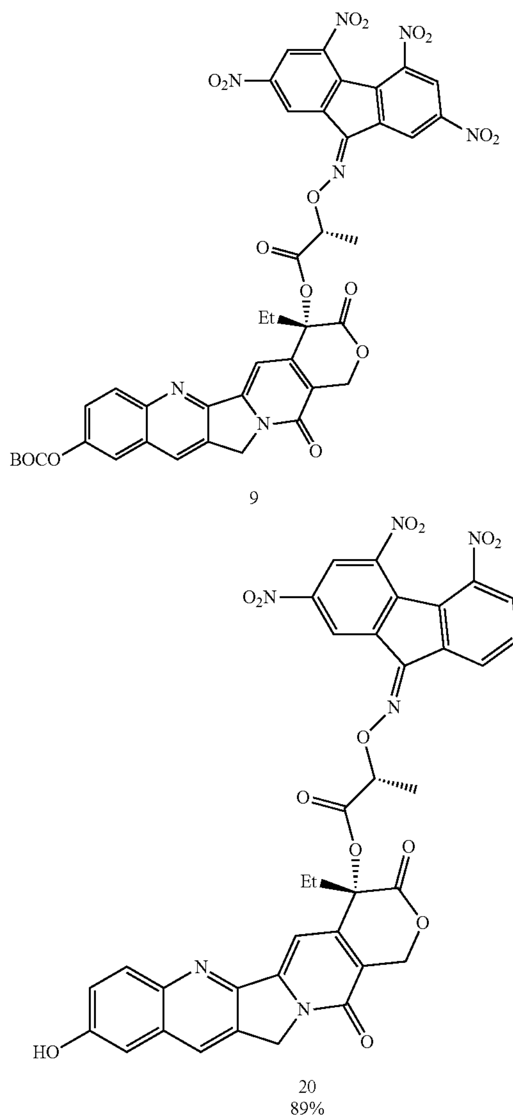

The 20-O-[(+)TAPA]-Boc-10H-CPT ester 9 (500 mg; 0.538 mmol) was dissolved in TFA (5.4 mL). After stirring at rt for 1 hr, the reaction mixture was added to water and the precipitate was filtered, dried and redissolved in DCM. The solution was dried over $Na_2SO_4$, filtered and the solvent was removed. The remaining residue was purified by silica gel column with 50-100% EtOAc:Hexanes to give 370 mg of 20 as yellow solid (89%). $^{1}$H NMR (1:1 Acetone-d6:$CDCl_3$) δ 9.37 (s, 1H, Ar), 8.72 (s, 1H, Ar), 8.41 (s, 1H, Ar), 8.23 (s, 1H, Ar), 8.05 (s, 1H, Ar), 7.45 (d, 1H, J=9.3 Hz, Ar), 7.32 (d, 1H, J=9.3 Hz, Ar), 7.16 (s, 1H, Ar), 6.99 (s, 1H, =CH—), 5.63 (d, 1H, J=17.4 Hz, —C—$CH_2$—O—C(O)—), 5.50-5.37 (m, 2H, —C—$CH_2$—O—C(O)— and O—C(O)—CH(Me)-O—), 5.15 (s, 2H, —C—$CH_2$—N—), 2.23 (dm, 2H, J=7.5 Hz, $CH_2$-Me), 1.74 (d, 3H, J=7.2 Hz, $CH_3$), 0.87 (t, 3H, J=7.5 Hz, $CH_3$); $^{13}$C NMR (2:1 $CDCl_3$:acetone-d6): δ 157.12, 148.98, 147.61, 146.28, 144.40, 134.01, 130.37, 129.85, 129.49, 129.27, 127.22, 123.63, 122.87, 122.59, 121.11, 120.45, 120.26, 109.29, 95.13, 80.81, 77.22, 67.63, 50.33, 32.21, 17.04, 7.73; M.p. 210-215° C. (dec); ESIMS: calcd for $C_{36}H_{23}N_7O_{15}$ $[M+H]^+$ 794.13, found 794.3.

Example 12

Compound 21

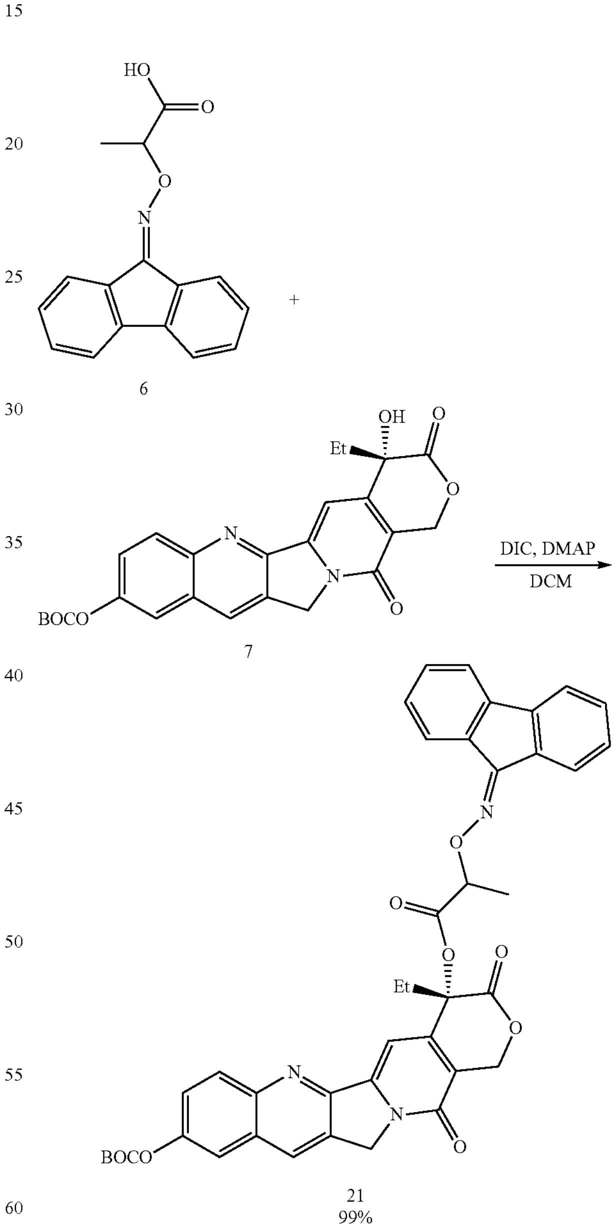

To a solution of 9F-propionic acid 6 (1.7 g 6.36 mmol), Boc-10H-CPT 7 (2 g, 4.3 mmol) and DIC (2 mL, 12.9 mmol) in anhy DCM (86 mL) was added DMAP (210 mg, 1.72 mmol). The reaction was stirred at rt for 1 hr, washed with saturated $NaHCO_3$ solution (1×50 mL), 1N HCl (2×50 mL), dried over $Na_2SO_4$ and the solvent was removed. The remaining residue was dissolved in 25 mL of DCM, precipitated with 200 mL of MeOH and filtered to give 3.05 g of 21 as a light yellow solid (99%). NMR ($CDCl_3$) δ 8.28 (m, 1H, Ar), 8.14 (d, 1H, J=9.3 Hz, Ar), 7.80-7.20 (m, 8H), 6.98 (t, 1H, J=7.2 Hz, Ar), 6.30 (t, 1H, J=7.5 Hz, Ar), 5.70 (d, 1H, J=17.4 Hz, —C—$CH_2$—O—C(O)—), 5.40 (d, 1H, J=17.4 Hz, —C—$CH_2$—O—C(O)—), 5.30-5.20 (m, 3H, —O—C(O)—CH(Me)-O—), and —C—$CH_2$—N—), 2.24 (dm, 2H, J=7.8 Hz, —$CH_2$-Me), 1.80 (d, 3H, J=7.2 Hz, —$CH_3$), 1.64 (s, 9H, 3 $CH_3$, t-Bu), 1.01 (t, 3H, J=7.8 Hz, —$CH_3$); ESIMS: calcd for $C_{41}H_{35}N_3O_9$ $[M+H]^+$ 714.24, found 714.4, 1427.4 (dimer).

Example 13

In vitro Chemoradiosensitization

Chemoradiosensitizing effects of compound 13 on human cancer cells were evaluated at a dose of 5 nM. DMS-114 small lung cancer cells were plated on petri dishes in triplicates were allowed to attach. The cells were subjected to 2 h drug exposures at 37° C. and then irradiated with X-rays at the doses indicated in Table 2. After irradiation, cells were rinsed with HBSS (Hank's balanced salt solution), and covered with fresh media. Cells were cultured for 8-9 days in a 37° C. incubator. The resulting cell colonies were stained and counted. Prior exposure to compound 13 significantly increased the radiosensitivity of the cancer cell (Table 2). Other compounds of this invention can similarly be evaluated in accordance with this method.

TABLE 2

In vitro chemoradiosensitization

| Radiation Dose (Gy) | Survival (%) Radiation alone | Survival (%) Radiation + compound 13 |
|---|---|---|
| 0 | 100 | 100 |
| 2 | 98 | 44 |
| 4 | 96 | 23 |
| 8 | 72 | 3 |

Example 14

In vivo Chemoradiosensitization

To determine whether the pronounced effects of compound 13 in tissue culture could be duplicated in solid tumors, in vivo chemoradiosensitization studies were performed on C3H/HeN mice bearing MTG-B mouse mammary adenocarcinoma tumors. Prior to treatment, the tumor grew exponentially following implantation into the flanks of the mice and reached a diameter of 8 mm (268.08 cu. mm) by day 7 to 10. The mice were injected i.p. with compound 13 at MTD using a single injection and then irradiated with a radiation dose of 22 Gy 24 h after the injection. Control groups of mice bearing 8 mm diameter tumors were treated with vehicle alone, or radiation alone, or drug alone. After treatment, tumor sizes were measured by caliper every day. Daily measurement of the tumor diameters (d1, d2) in two orthogonal directions were used to calculate the tumor volume (tumor volume=$\pi/6\{(d1+d2)/2\}^3$) using the approximation that the tumors were spherical (results shown in FIG. 1). The values of time (days) required to grow the tumor to twice their initial size after various treatments were calculated as tumor doubling time (TDT) (±SE) for evaluating the treatment effects. Survival times and curative effects after treatment were also be observed and recorded. Other compounds of this invention can similarly be evaluated in accordance with this method.

TABLE 3

In vivo Chemoradiosensitization

| regimen | TDT (days) | Survival (days) |
|---|---|---|
| control | 1 | 7 |
| Radiation alone | 2 | 15 |
| compound 13 alone | 12 | 24 |
| compound 13 plus radiation | 33 | 90 |

Example 15

Chemotherapeutic Activity of Compound 13

Chemotherapeutic effects of compound 13 on human prostate cancer cells (PC-3 and DU-145) were evaluated at dose concentrations between 0 and 10 nM. Cells plated on Petri dishes in triplicates were allowed to attach, then cells were subjected to 24 hr drug exposure at 37° C. The cells were then rinsed with HBSS ((Hank's balanced salt solution) and covered with fresh media. Cells were cultured for 8-9 days in a 37° C. incubator. The resulting cell colonies were stained and counted. Results are presented in Table 4.

TABLE 4

Chemotherapeutic Activity of compound 13

| Drug conc. (nM) | PC-3 Cells % Survival | DU-145 Cells % Survival |
|---|---|---|
| 0 | 100 | 100 |
| 1 | 98 | 82 |
| 5 | 52 | 43 |
| 10 | 10 | 5 |

Figure 2:
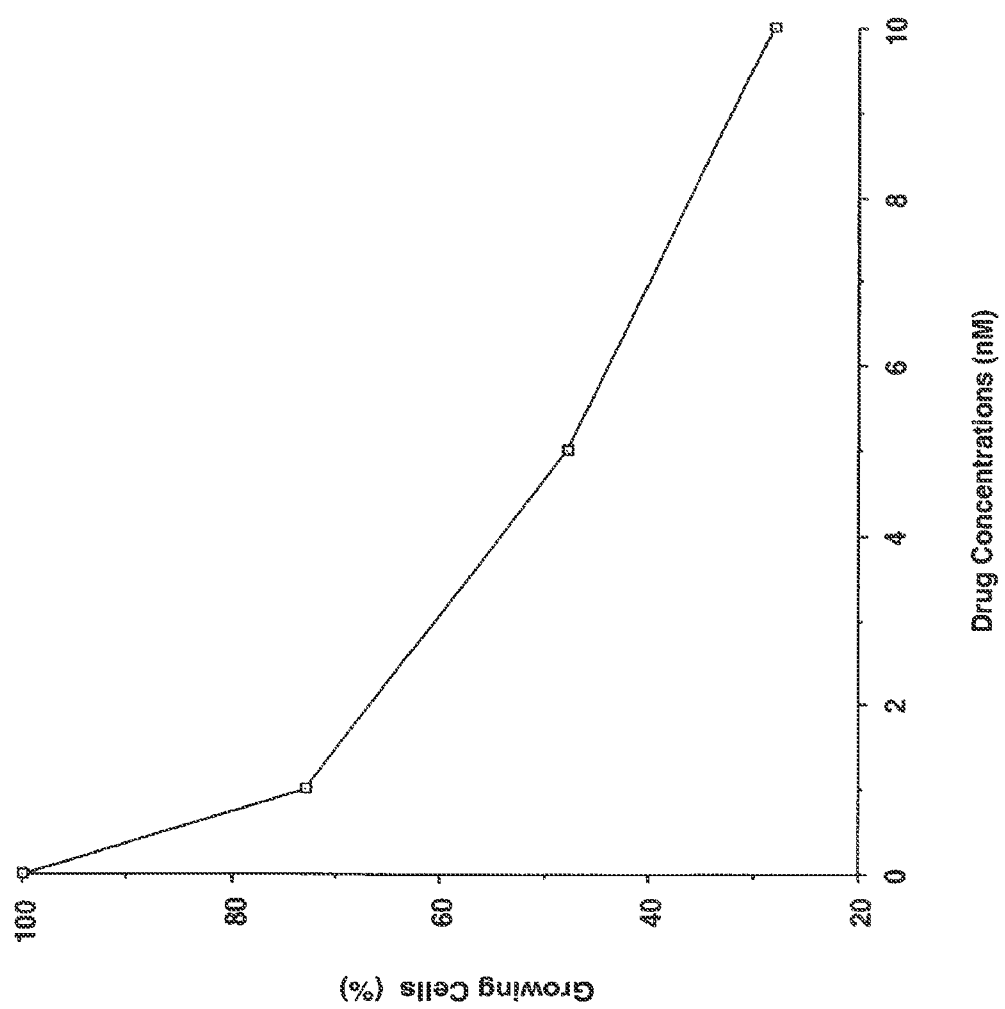
FIG. 2 is a graph depicting in vitro chemotherapeutic activity of compound 13 on MCF-7 human breast cancer cells, as described in Example 15.

Chemotherapeutic effects of compound 13 on human breast cancer cells (MCF7) were evaluated at dose concentrations between 0 and 10 nM. Cells plated on Petri dishes in triplicates were allowed to attach, then cells were subjected to 72 hr drug exposure at 37° C. The cells were then rinsed with HBSS ((Hank's balanced salt solution) and covered with fresh media. Cells were cultured for 8-9 days in a 37° C. incubator. The resulting cell colonies were stained and counted. Results are presented in FIG. 2. Other compounds of this invention can similarly be evaluated in accordance with this method.

Example 16

Decreased Toxicity of Compound 13

Drugs were dissolved in cremophor:alcohol (1:1) and diluted in saline to a 5% cremophor, 5% alcohol, 90% saline for i.p. injection.

Acute toxicities of a compound of this invention, compound 13, topotecan; CPT and cisplatin were evaluated on C3H/HeN mice (female, 6-8 week old, body weight 18-20 g).

Figure 3:
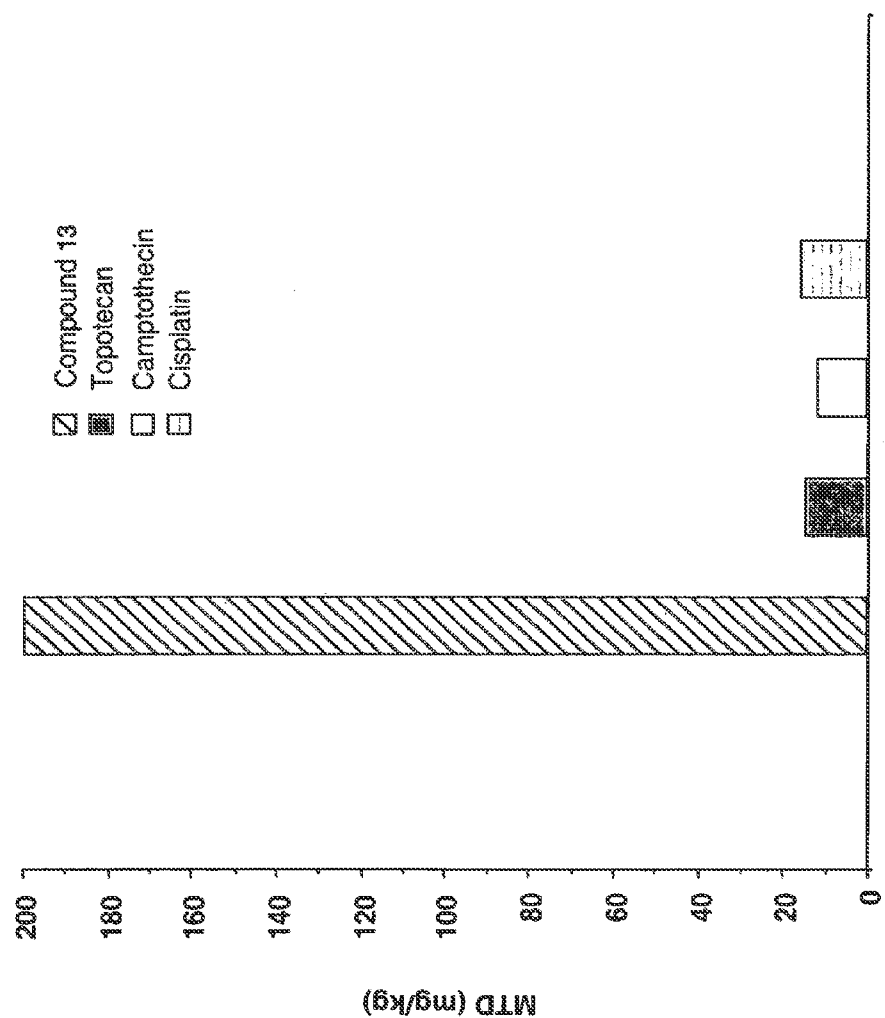
FIG. 3 is a graph depicting the maximum tolerated dose (MTD) of compound 13, topotecan, camptothecin and cisplatin, as described in Example 16.

The MTD40 (maximum tolerated dose at day 40) values were determined. In the consecutive type studies, 6 mice were dosed at moderate doses of 10, 70, or 106.98, or 141.47, or 187.1 mg/kg. If no severe and irreversible toxicity (euthanasia is required) occurred at these doses, additional 6 animals were initiated at a dose which is 1.3225-1.5283 times higher than the previous non-toxic doses. Sequential dosages (261.94, or 366.72, or 500 mg/kg) were increased until severe and irreversible toxicity (whereby euthanasia is required) occurs. If severe and irreversible toxicity was observed at these doses, the drug doses (50, or 30 mg/kg) were reduced. The result of this exercise was two dosages, one apparently nonlethal and the other lethal if severe and irreversible toxicity occurred and euthanasia was required. Six mice were dosed at each dosage. If no severe and irreversible toxicity occurred at the lower dosage and at least one with severe and irreversible toxicity at the higher dose, then the lower dose was considered to the MTD. These new camptothecin analogs were administered to C3H/HeN mice by i.p. injection. Drug toxicity was evaluated on mice, checked daily for 45 days. The toxicity parameters reported were the MTD40. The MTD is defined as the highest dose causing no severe irreversible toxicity in one treatment group, but at least one animal exhibiting severe and irreversible toxicity and being euthanized at next higher dose. Results are provided in FIG. 3. Other compounds of this invention can similarly be evaluated in accordance with this method.

Example 17

In vitro Chemoradiosensitization

Chemoradiosensitizing effects of compound 13, compound 10, and compound 20 on human cancer cells were evaluated at a dose of 5 nM. PC-3 human prostate cancer cells were plated on petri dishes in triplicates were allowed to attach. The cells were subjected to 2 h drug exposures at 37° C. and then irradiated with X-rays at the doses indicated in Table 5. After irradiation, cells were rinsed with HBSS (Hank's balanced salt solution), and covered with fresh media. Cells were cultured for 8-9 days in a 37° C. incubator. The resulting cell colonies were stained and counted. Prior exposure to compound 13, compound 10, and compound 20 significantly increased the radiosensitivity of the cancer cell (Table 5). Other compounds of this invention can similarly be evaluated in accordance with this method.

TABLE 5

In vitro chemoradiosensitization

| Radiation Dose (Gy) | Survival (%) Radiation alone | Radiation + compound 13 | Radiation alone | Radiation + compound 10 | Radiation alone | Radiation + compound 20 |
|---|---|---|---|---|---|---|
| 0 | 100 | 100 | 100 | 100 | 100 | 100 |
| 1 | 97 | 83 | 98 | 90 | 98 | 82 |
| 2 | 90 | 60 | 87 | 66 | 88 | 65 |
| 4 | 50 | 22 | 50 | 21 | 47 | 22 |

Example 18

Chemotherapeutic Activity of CPT Analogs

Cell Colony Formation Assay

Four hundred cells (HCT116: human colon cancer cell line) or five hundred cells (VM46: taxol-resistant, overexpressing multi-drug resistant gene, sub-line of HCT-116)(PC-3: human prostate cancer cell line) were plated in 60 mm Petri dishes containing 2.7 mL of medium (modified McCoy's 5a medium containing 10% fetal bovine serum and 100 units/ml penicillin and 100 μg/ml streptomycin). The cells were incubated in a $CO_2$ incubator at 37° C. for 5 hours for attachment to the bottom of Petri dishes. Drugs were made up fresh in medium at ten times the final concentration, and then 0.3 ml of this stock solution was added to the 2.7 mL of medium containing 5% bovine calf serum (BCS) in the dish. The cells were then incubated with drugs for 72 hours at 37° C. At the end of incubation the drug-containing media were decanted, the dishes were rinsed with 4 ml of Hank's Balance Salt Solution (HBSS), 5 ml of fresh medium containing 15% BCS was added, and the dishes were returned to the incubator for colony formation. The cell colonies stained with methylene blue (0.5% in ethanol) were counted using colony counter after incubation for 8 days for HCT116 cells and PC-3 cells and 9 days for VM46 cells, respectively. Cell survival was calculated and the values of 1050 (the drug concentration producing 50% inhibition of colony formation) were determined for each tested compound. Results are provided in Table 6. Other compounds of this invention can similarly be evaluated in accordance with this method.

TABLE 6

Chemotherapeutic Activity of CPT analogs

| Compound # | IC50 (nM) HCT116 | PC-3 | VM46 |
|---|---|---|---|
| 13 | 3.2 | 5.0 | 3.0 |
| 14 | no effect | — | no effect |
| 10 | 16.4 | — | 11 |
| 15 | no effect | — | no effect |
| 16 | 8.6 | — | 6.7 |
| 17 | 4.0 | 6.0 | 3.0 |
| 18 | no effect | — | no effect |
| 12 | 7.7 | — | 5.7 |
| 19 | 3.0 | — | 0.6 |
| 20 | 3.3 | 6.0 | 1.5 |
| 8 | 3.0 | — | 0.6 |
| 21 | 3.0 | — | 0.6 |
| Topotecan | 10.3 | no effect | 10.6 |

Several CPT analogs tested above showed in vitro chemotherapeutic activity against human colon cancer cell line (HCT116:), sub-line of HCT116 (VM46) and human prostate cancer cell line (PC-3). The three compounds that did not display any in vitro chemotherapeutic effect, namely compound 14, compound 15, and compound 18, are analogs of Irinotecan: a semisynthetic camptothecin derivative introduced in the 1980's. Irinotecan is a prodrug metabolized by carboxylesterases to an active metabolite 7-ethyl-10-hydroxy-camptothecin (SN38) which then exerts its cytotoxic effect (Ando Y. al. N Engl Med 2002; 346(18):1414-1415).

Accordingly, Irinotecan derivatives can be expected not to display any in vitro chemotherapeutic activity but display only in vivo activity after getting metabolized in the body, which is consistent with the lack of in vitro activity seen for the 3 Irinotecan analogs mentioned above.

What is claimed is:

1. A compound of the formula (II) or a pharmaceutically acceptable salt thereof, (II)

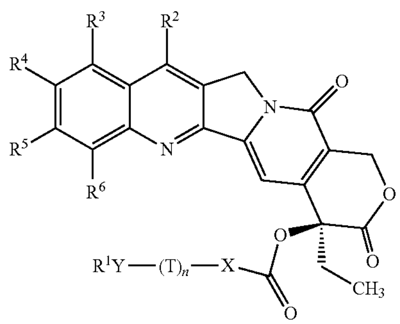

wherein

X is a S,—NH—, or a covalent bond;

Y is =NO—, —N(H)O—, =N—, —NR—, O, S, or a covalent bond;

T is independently CRR';

each of R and R' is independently selected from hydrogen, $C_{1-4}$alkyl, and substituted $C_{1-4}$alkyl;

n is an integer from 0 to 8;

$R^1$ is optionally substituted carbocyclic, optionally substituted heterocyclic, or optionally substituted fused 2-, 3- or 4-ring heterocyclic; wherein when X is —NH—and $R^1$is heterocyclic, the heterocyclic is substituted with at least one nitro;

provided that when X is a covalent bond, Y is =NO—, —N(H)O—, or=N—;

$R^2$ is hydrogen, halo. lower alkyl, lower alkoxy. hydroxy, $R^{Q}$Y-L-C(O)O—, cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkoxycarbonyloxy, sugar, phosphosugar, O-quinone, substituted lower alkyl aminomethyl, lower alkylcarbonylamino, lower alkylcarbonyloxy methyl, optionally substituted lower alkylcarbonyloxy methyl, substituted vinyl, 1-hydroxy-2-nitroethyl, alkoxycarbonylethyl, aminocarbonyl, alkylcarbonyl, al kylcarbonyloxymethyl, benzoylmethyl, benzylcarbonyloxymethyl, lower alkyliminomethyl or lower alkoxymethyl;

$R^3$ is hydrogen, halo, lower alkyl, lower alkoxy, hydroxy, $R^{Q}$Y-L-C(O)O—, cyano, nitro, amino, halogenated lower alkyl, halogenated lower alkoxy, hydroxycarbonyl, formyl, lower alkoxycarbonyl, $CH_2NR^7$ $R^8$ (where each of $R^7$ and $R^8$ is independently H, alkyl of 1-6 carbons, optionally substituted phenyl, hydroxy lower alkyl, amino lower alkyl, or mono- or dialkylamino lower alkyl, or $R^7$ and $R^8$ taken together with —N—represent a cyclic amino-), $CH_2R^9$ (where $R^9$ is lower alkoxy, CN, amino lower alkoxy, mono- or di-lower alkylamino lower alkoxy, lower alkylthio, amino lower alkylthio, or mono- or di-lower alkylamino lower alkylthio), $NR^{10}R^{11}$ (where each of $R^{10}$ and $R^{11}$ is independently hydrogen, lower alkyl, phenyl, hydroxy lower alkyl, or amino lower alkyl, or $R^{10}$ and $R^{11}$ taken together with —N—represent a cyclic amino), trialkylsilyl, dialkylamino alkyl, lower alkylcarbonyloxy, lower alkoxycarbonyloxy, sugar, phosphosugar, O-quinone, substituted lower alkyl aminomethyl, or lower alkylcarbonylamino or $R^3$ together with $R^4$ is furan, dihydrofuran or 1,4 -oxazine-2-one;

$R^4$ is hydrogen, halo, lower alkyl, lower alkoxy, hydroxy, $R^{Q}$Y-L-C(O)O—, cyano, nitro, amino, amino lower alkyl, halogenated lower alkyl, halogenated lower alkoxy, hydroxyearbonyl, formyl, lower alkoxycarbonyl, carbamoyloxy, lower alkylcarbonyloxy, lower alkoxycarbonyloxy, sugar, phosphosugar, O-quinone, substituted lower alkyl aminomethyl, or lower alkylcarbonylamino, or $R^4$ together with $R^3$ is furan, dihydrofuran or 1,4-oxazine-2-one, or $R^4$ together with $R^5$ is methylenedioxy;

$R^5$ is hydrogen, halo, lower alkyl, lower alkoxy, hydroxyl, $R^{Q}$Y-L-C(O)O—, cyano, nitro, amino, halogenated lower alkyl, halogenated lower alkoxy. hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino;

$R^6$ is hydrogen, halo, lower alkyl, lower alkoxy, hydroxy, $R^{Q}$Y-L-C(O)O—, cyano, nitro, amino, trialkylsilyl, halogenated lower alkyl, halogenated lower alkoxy, hydroxycarbonyl, formyl, lower alkoxycarbonyl, lower alkylcarbonyloxy, lower alkoxycarbonyloxy, sugar, phosphosugar, O-quinone, substituted lower alkyl aminomethyl, or lower alkylcarbonylamino;

L is a bond or linear alkylene (1-8) group, optionally substituted with lower alkyl or substituted lower alkyl, wherein one or two hylene (—$CH_2$—) units of the linear alkylene group is optionally replaced with O, S or NH; and $R^{Q}$ is optionally substituted carbocyclic, optionally substituted heterocyclic, or optionally substituted fused 2-, 3- or 4-ring heterocyclic.

2. The compound of claim 1, wherein one of the $R^2$, $R^4$, or $R^5$ is selected from the group consisting of (tris(hydroxymethyl)methylamino)methyl, (bis(hydroxymethyl)methylamino)methyl, and (2-hydroxyethylamino)methyl.

3. The compound of claim 2, wherein $R^2$ is selected from the group consisting of (tris(hydroxymethyl)methylamino) methyl, (bis(hydroxymethyl)methylamino)methyl, and (2-hydroxyethylamino)methyl.

4. The compound of claim 3, wherein $R^3$ is hydrogen, dimethylamino, amino, or nitro;

$R^4$ is hydrogen, hydroxy, or 4-(1-piperidino)-1-piperidinocarbonyloxy; or $R^4$ together with $R^5$ is methylenedioxy;

$R^5$ is hydrogen; or $R^5$ together with $R^4$ is methylenedioxy; and $R^6$ is hydrogen.

5. The compound of claim 4, wherein $R^3$ is hydrogen; and $R^4$ together with $R^5$ is methylenedioxy.

6. The compound of claim 4, wherein each of $R^3$, $R^4$, and $R^5$ is hydrogen.

7. The compound of claim 1, wherein $R^1$ is aromatic.

8. The compound of claim 7, wherein X is a covalent bond.

9. The compound of claim 8, wherein Y is =NO— or —N(H)O—.

10. The compound of claim 9, wherein n is 1 and each of R and R' is independently methyl or hydrogen.

11. The compound of claim 10, wherein $R^1$ is a substituted or unsubstituted carbocyclic.

12. The compound of claim 1, wherein the substituted or unsubstituted carbocyclic is 9-fluorenyl.

13. The compound of claim 12, wherein the 9-fluorenyl is substituted with at least one nitro group.

14. The compound of claim 13, wherein $R^1$ is

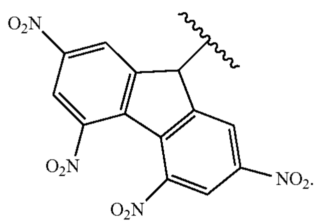 [SMILES: *C1c2cc([N+](=O)[O-])cc([N+](=O)[O-])c2-c2c1cc([N+](=O)[O-])cc2[N+](=O)[O-]]

15. A compound of claim 1, wherein $R^1$ or $R^Q$ is

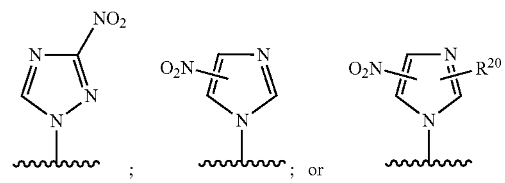

wherein $R^{20}$ is halo, alkyl, or substituted alkyl.

16. A compound of claim 1, wherein $R^1$ Y-$(T)_n$-X—C(O)O— is

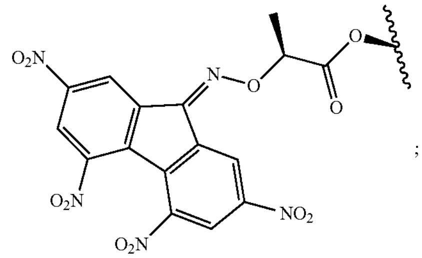

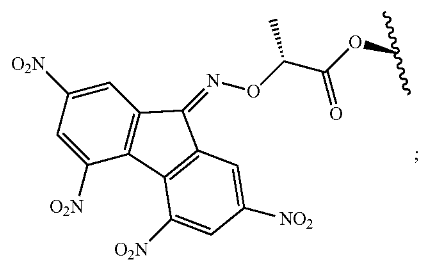

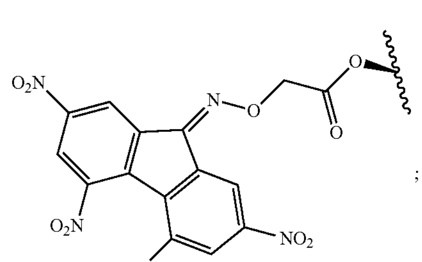

-continued

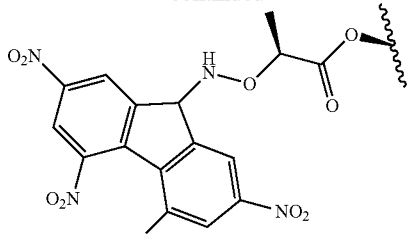

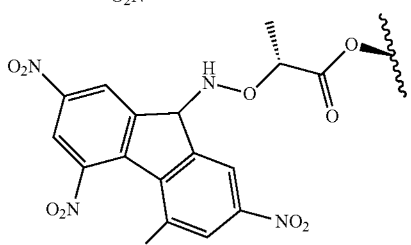

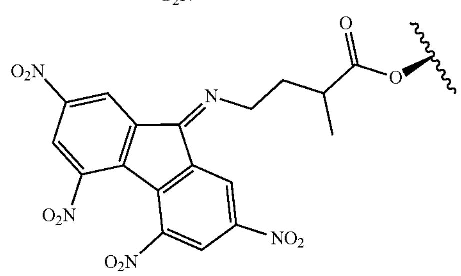

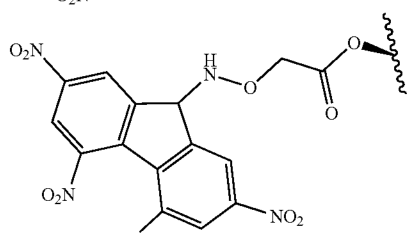

17. The compound of claim 1, wherein $R^2$ is hydrogen;

$R^3$ is $CH_2NR^7R^8$ is independently H, alkyl of 1-6 carbons, optionally substituted phenyl, hydroxy lower alkyl, amino lower alkyl, or mono-or dialkylamino lower alkyl, or $R^7$ and $R^8$ taken together with —N —represent a cyclic amino-), $NR^{10}R^{11}$ (where each of $R^{10}$ and $R^{11}$ is independently hydrogen, lower alkyl, phenyl, hydroxy lower alkyl, or amino lower alkyl, or $R^{10}$ and $R^{11}$taken together with —N—represent a cyclic amino), or dialkylamino alkyl;

$R^4$ is lower alkoxy, hydroxy, halogenated lower alkyl, halogenated lower alkoxy, hydroxycarbonyl, formyl, lower alkoxycarbonyl, carbamoyloxy, lower alkylcarbonyloxy, lower alkoxycarbonyloxy, sugar, phosphosugar, or $R^4$ together with $R^5$ is methylenedioxy;

$R^5$ is hydrogen or together with $R^4$ is methylenedioxy; and $R^6$ is hydrogen.

18. The compound of claim 17, wherein $R^3$ is $CH_2NR^7R^8$ (where each of $R^7$ and $R^8$ is lower alkyl), $R^4$ is hydroxy, alkoxy, lower alkoxycarbonyloxy or alkylcarbonyloxy, and $R^5$ is hydrogen.

19. The compound of claim 1, wherein $R^2$ is hydrogen, lower alkyl or halogenated lower alkyl;

$R^3$ is hydrogen or lower alkyl;

$R^4$ is lower alkoxy, hydroxy, halogenated lower alkoxy, hydroxycarbonyl, carbamoyloxy, lower alkylcarbonyloxy, lower alkoxycarbonyloxy, sugar, phosphosugar, or $R^4$ together with $R^5$ is methylenedioxy;

$R^5$ is hydrogen or together with $R^4$ is methylenedioxy; and $R^6$ is hydrogen.

20. The compound of claim 19, wherein $R^3$ is hydrogen, $R^4$ is carbamoyloxy, and $R^5$ is hydrogen.

21. The compound of claim 19, wherein $R^2$ is lower alkyl and $R^4$ is 4-(1-peridino)-1-piperidinocarbonyloxy.

22. The compound of claim 19. wherein $R^2$ is hydrogen, and $R^4$ is 4-(1-piperidino)-1-piperidinocarbonyloxy.

23. The compound of claim 19, wherein $R^2$ is hydrogen, $R^3$ is hydrogen and $R^4$ is tert-butyloxycarbonyloxy.

24. The compound of claim 1, wherein $R^2$ is lower alkyl;

$R^3$ is hydrogen;

$R^4$ is hydroxy, lower alkoxy, halogenated lower alkoxy, hydroxycarbonyl, formyl, lower alkoxycarbonyl, lower alkylcarbonyloxy, lower alkoxycarbonyloxy, sugar, or phosphosugar;

$R^5$ is hydrogen; and $R^6$ is hydrogen.

25. The compound of claim 24, wherein $R^2$ is ethyl and $R^4$ is hydroxy.

26. The compound of claim 1, wherein each of $R^2$, $R^4$, $R^5$ and $R^6$ is hydrogen and $R^3$ is amino or nitro.

27. The compound of claim 1, wherein $R^2$ is tri-lower alkylsilyl;

$R^3$ is hydrogen;

$R^4$ is hydroxy, lower alkoxy, halogenated lower alkoxy, hydroxycarbonyl, formyl, lower alkoxycarbonyl, carbamoyloxy, lower alkylcarbonyloxy, lower alkoxycarbonyloxy, sugar, or phosphosugar;

$R^5$ is hydrogen; and $R^6$ is hydrogen.

28. The compound of claim 27, wherein $R^2$ is t-butyldimethylsilyl and $R^4$ is hydroxy.

29. A composition comprising a compound according to claim 1, together with a pharmaceutically acceptable excipient.

30. The compound of claim 1, provided that when X is a covalent bond, $R^1$ is not fluorenyl or fluorenyl substituted with at least one nitro group.

* * * * *